US009321664B2

(12) United States Patent
Li et al.

(10) Patent No.: US 9,321,664 B2
(45) Date of Patent: Apr. 26, 2016

(54) STABLE PERCARBOXYLIC ACID COMPOSITIONS AND USES THEREOF

(71) Applicant: Ecolab USA Inc., St. Paul, MN (US)

(72) Inventors: Junzhong Li, Apple Valley, MN (US); David McSherry, St. Paul, MN (US); Allison Brewster, St. Paul, MN (US); Richard Staub, Lakeview, MN (US); Renato De Paula, Sugar Land, TX (US); John Wilhelm Bolduc, Eagan, MN (US); Robert J. Ryther, Saint Paul, MN (US); Victor V. Keasler, Richmond, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 13/844,515

(22) Filed: Mar. 15, 2013

(65) Prior Publication Data

US 2014/0097144 A1 Apr. 10, 2014

Related U.S. Application Data

(60) Provisional application No. 61/710,631, filed on Oct. 5, 2012, provisional application No. 61/762,777, filed on Feb. 8, 2013.

(51) Int. Cl.
| | | |
|---|---|---|
| *C07C 227/40* | (2006.01) |
| *C02F 1/68* | (2006.01) |
| *C11D 7/32* | (2006.01) |
| *C11D 7/36* | (2006.01) |
| *C11D 3/39* | (2006.01) |
| *A01N 25/22* | (2006.01) |
| *C02F 1/72* | (2006.01) |
| *C02F 103/10* | (2006.01) |
| *C02F 103/00* | (2006.01) |
| *C02F 103/02* | (2006.01) |
| *C02F 103/42* | (2006.01) |

(52) U.S. Cl.
CPC .............. *C02F 1/682* (2013.01); *A01N 25/22* (2013.01); *C02F 1/722* (2013.01); *C11D 3/394* (2013.01); *C11D 7/3281* (2013.01); *C11D 7/36* (2013.01); *C02F 2103/007* (2013.01); *C02F 2103/023* (2013.01); *C02F 2103/10* (2013.01); *C02F 2103/42* (2013.01); *C02F 2303/02* (2013.01); *C02F 2303/04* (2013.01)

(58) Field of Classification Search
None
See application file for complete search history.

(56) References Cited

U.S. PATENT DOCUMENTS

| | | |
|---|---|---|
| 2,609,391 A | 9/1952 | Greenspan et al. |
| 2,955,905 A | 10/1960 | Davies et al. |
| 3,053,633 A | 9/1962 | Dunlop et al. |
| 3,130,169 A | 4/1964 | Blumbergs et al. |
| 3,156,654 A | 11/1964 | Konecny et al. |
| 3,256,198 A | 6/1966 | Matzner |
| 3,272,750 A | 9/1966 | Chase |
| 3,432,546 A | 3/1969 | Oringer et al. |
| 3,847,830 A | 11/1974 | Williams et al. |
| 3,925,234 A | 12/1975 | Hachmann et al. |
| 3,956,159 A | 5/1976 | Jones |
| 3,969,258 A | 7/1976 | Carandang et al. |
| 4,003,841 A | 1/1977 | Hachmann et al. |
| 4,013,575 A | 3/1977 | Castrantas et al. |
| 4,051,058 A | 9/1977 | Bowing et al. |
| 4,051,059 A | 9/1977 | Bowing et al. |
| 4,100,095 A | 7/1978 | Hutchins et al. |
| 4,126,573 A | 11/1978 | Johnston |
| 4,129,517 A | 12/1978 | Eggensperger et al. |
| 4,144,179 A | 3/1979 | Chatterji |
| 4,170,453 A | 10/1979 | Kitko |
| 4,233,235 A | 11/1980 | Camden et al. |
| 4,297,298 A | 10/1981 | Crommelynck et al. |
| 4,367,156 A | 1/1983 | Diehl |
| 4,370,251 A | 1/1983 | Liao et al. |
| 4,374,035 A | 2/1983 | Bossu |
| 4,391,723 A | 7/1983 | Bacon et al. |
| 4,391,724 A | 7/1983 | Bacon |
| 4,412,934 A | 11/1983 | Chung et al. |
| 4,473,507 A | 9/1984 | Bossu |
| 4,483,778 A | 11/1984 | Thompson et al. |
| 4,486,327 A | 12/1984 | Murphy et al. |
| 4,529,534 A | 7/1985 | Richardson |
| 4,587,264 A | 5/1986 | Jourdan-Laforte et al. |
| 4,588,506 A | 5/1986 | Raymond et al. |
| 4,617,090 A | 10/1986 | Chum et al. |
| 4,655,781 A | 4/1987 | Hsieh et al. |

(Continued)

FOREIGN PATENT DOCUMENTS

| | | |
|---|---|---|
| CA | 2084172 | 6/1993 |
| CA | 2152908 | 7/1994 |

(Continued)

OTHER PUBLICATIONS

International Search Report and Written Opinion for PCT/US2013/030904, mailed Jul. 5, 2013, 14 pages.
Database CAPLUS Chemical Abstracts Service, Accession No. 1960:97225, abstract of DE 1024514, Feb. 20, 1958 "Oxidation of organic compounds with hydrogen peroxide in the liquid base".
Office Action for U.S. Appl. No. 13/785,405, mailed Oct. 22, 2013, 12 pages.
Request for Continued Examination for U.S. Appl. No. 12/066,686, filed Sep. 18, 2013, 10 pages.
*A.O.A.C. Use Dilution Methods*, Official Methods of Analysis of the Association of Official Analytical Chemists, paragraph 955.14 and applicable sections, 15th Edition, 1990 (EPA Guideline 91-2.
Brooks, Robert E., et al., "Alkaline hydrogen peroxide bleaching of cellulose", Kluwer Academic Publishers, Cellulose 7: 263-286, 2000 (24 pages).
Carboni-Oerlemans, Chiara, et al., "Hydrolase-catalysed synthesis of peroxycarboxylic acids: Biocatalytic promiscuity for practical applications", Elsevier, Journal of Biotechnology, 126 (2006) 140-151 (12 pages).
Chen, J., "Enhanced Alkaline Peroxide Bleaching of Softwood Kraft Pulps Using a New Activator," Journal of Pulp and Paper Science: vol. 27, No. 12, Dec. 2001 (4 pages).
Dannacher, Josef J., "Catalytic bleach: Most valuable applications for smart oxidation chemistry", Journal of Molecular Catalysis A: Chemical 251 (2006) 159-176.

(Continued)

*Primary Examiner* — Karl J Puttlitz

(74) *Attorney, Agent, or Firm* — Morrison & Foerster, LLP

(57) ABSTRACT

The present invention relates generally to stable percarboxylic acid compositions comprising, inter alia, at least two stabilizing agents, and various uses for water treatments, including water treatments in connection with oil- and gas-field operations. The present invention also relates to slick water compositions and gel based compositions that comprise stable percarboxylic acid compositions and the use thereof in oil- and gas-field operations.

21 Claims, 4 Drawing Sheets

(56) References Cited

U.S. PATENT DOCUMENTS

| | | | |
|---|---|---|---|
| 4,681,592 A | 7/1987 | Hardy et al. |
| 4,778,618 A | 10/1988 | Fong et al. |
| 4,783,278 A | 11/1988 | Sanderson et al. |
| 4,853,143 A | 8/1989 | Hardy et al. |
| 4,879,057 A | 11/1989 | Dankowski et al. |
| 4,917,815 A | 4/1990 | Beilfuss et al. |
| 4,957,647 A | 9/1990 | Zielske |
| 4,964,870 A | 10/1990 | Fong et al. |
| 5,019,292 A | 5/1991 | Baeck et al. |
| 5,030,240 A | 7/1991 | Wiersema et al. |
| 5,073,285 A | 12/1991 | Liberati et al. |
| 5,098,598 A | 3/1992 | Sankey et al. |
| 5,143,641 A | 9/1992 | Nunn |
| 5,196,133 A | 3/1993 | Leslie et al. |
| 5,200,189 A | 4/1993 | Oakes et al. |
| 5,250,212 A | 10/1993 | de Buzzaccarini et al. |
| 5,250,707 A | 10/1993 | Inaba et al. |
| 5,266,587 A | 11/1993 | Sankey et al. |
| 5,296,239 A | 3/1994 | Colery et al. |
| 5,310,774 A | 5/1994 | Farrar |
| 5,314,687 A | 5/1994 | Oakes et al. |
| 5,349,083 A * | 9/1994 | Brougham et al. ............... 562/6 |
| 5,382,571 A | 1/1995 | Granger et al. |
| 5,431,849 A | 7/1995 | Damhus et al. |
| 5,435,808 A | 7/1995 | Holzhauer et al. |
| 5,447,648 A | 9/1995 | Steindorf |
| 5,453,214 A | 9/1995 | van den Berg et al. |
| 5,463,112 A | 10/1995 | Sankey et al. |
| 5,464,563 A | 11/1995 | Moore et al. |
| 5,466,825 A | 11/1995 | Carr et al. |
| 5,472,619 A | 12/1995 | Holzhauer et al. |
| 5,486,212 A | 1/1996 | Mitchell et al. |
| 5,503,765 A | 4/1996 | Schepers et al. |
| 5,505,740 A | 4/1996 | Kong et al. |
| 5,545,374 A | 8/1996 | French et al. |
| 5,565,231 A | 10/1996 | Malone et al. |
| 5,576,282 A | 11/1996 | Miracle et al. |
| 5,589,507 A | 12/1996 | Hall, II et al. |
| 5,595,967 A | 1/1997 | Miracle et al. |
| 5,599,781 A | 2/1997 | Haeggberg et al. |
| 5,624,634 A | 4/1997 | Brougham et al. |
| 5,632,676 A | 5/1997 | Kurschner et al. |
| 5,635,195 A | 6/1997 | Hall, II et al. |
| 5,637,755 A | 6/1997 | Nagumo et al. |
| 5,647,997 A | 7/1997 | Holzhauer et al. |
| 5,681,805 A | 10/1997 | Scheuing et al. |
| 5,716,923 A | 2/1998 | MacBeath |
| 5,718,910 A | 2/1998 | Oakes et al. |
| 5,767,308 A | 6/1998 | Thiele et al. |
| 5,780,064 A | 7/1998 | Meisters et al. |
| 5,785,867 A | 7/1998 | LaZonby et al. |
| 5,827,447 A | 10/1998 | Tamura et al. |
| 5,827,808 A | 10/1998 | Appleby et al. |
| 5,840,343 A | 11/1998 | Hall, II et al. |
| 5,880,083 A | 3/1999 | Beaujean et al. |
| 5,914,303 A | 6/1999 | Sankey et al. |
| 5,929,012 A | 7/1999 | Del Duca et al. |
| 5,965,033 A | 10/1999 | Huss et al. |
| 5,965,785 A | 10/1999 | Braden et al. |
| 5,977,403 A | 11/1999 | Byers |
| 5,998,350 A | 12/1999 | Burns et al. |
| 6,010,729 A | 1/2000 | Gutzmann et al. |
| 6,022,381 A | 2/2000 | Dias et al. |
| 6,049,002 A | 4/2000 | Mattila et al. |
| 6,103,286 A | 8/2000 | Gutzmann et al. |
| 6,110,883 A | 8/2000 | Petri et al. |
| 6,156,156 A | 12/2000 | Rousu et al. |
| 6,165,483 A | 12/2000 | Hei et al. |
| 6,177,393 B1 | 1/2001 | McGregor et al. |
| 6,183,763 B1 | 2/2001 | Beerse et al. |
| 6,207,632 B1 | 3/2001 | Brooker et al. |
| 6,211,237 B1 | 4/2001 | Huss et al. |
| 6,221,341 B1 | 4/2001 | Montgomery |
| 6,238,685 B1 | 5/2001 | Hei et al. |
| 6,284,793 B1 | 9/2001 | Fuchs et al. |
| 6,294,186 B1 | 9/2001 | Beerse et al. |
| 6,326,032 B1 | 12/2001 | Richter et al. |
| 6,399,564 B1 | 6/2002 | Speed et al. |
| 6,407,052 B2 | 6/2002 | Gassenmeier et al. |
| 6,417,151 B1 | 7/2002 | Grothus et al. |
| 6,432,661 B1 | 8/2002 | Heitfeld et al. |
| 6,436,885 B2 | 8/2002 | Biedermann et al. |
| 6,545,047 B2 | 4/2003 | Gutzmann et al. |
| 6,566,318 B2 | 5/2003 | Perkins et al. |
| 6,569,286 B1 | 5/2003 | Withenshaw et al. |
| 6,589,565 B1 | 7/2003 | Richter et al. |
| 6,599,871 B2 | 7/2003 | Smith |
| 6,602,845 B2 | 8/2003 | Connor et al. |
| 6,627,657 B1 * | 9/2003 | Hilgren et al. ............... 514/553 |
| 6,635,286 B2 | 10/2003 | Hei et al. |
| 6,649,140 B2 | 11/2003 | Paparatto et al. |
| 6,686,324 B2 | 2/2004 | Ramirez et al. |
| 6,689,732 B1 | 2/2004 | Guedira et al. |
| 6,696,093 B2 | 2/2004 | Ney et al. |
| 6,770,774 B2 | 8/2004 | Van De Bovenkamp-Bouwman et al. |
| 6,806,246 B2 | 10/2004 | Preissner et al. |
| 6,866,749 B2 | 3/2005 | Delmas et al. |
| 6,878,680 B2 | 4/2005 | Kitko et al. |
| 6,919,304 B2 | 7/2005 | Dykstra et al. |
| 7,012,154 B2 | 3/2006 | Vineyard et al. |
| 7,060,136 B1 | 6/2006 | Zeiher et al. |
| 7,078,373 B2 | 7/2006 | Burrows et al. |
| 7,148,351 B2 | 12/2006 | Morris et al. |
| 7,169,236 B2 | 1/2007 | Zeiher et al. |
| 7,189,385 B2 | 3/2007 | Montgomery |
| 7,217,295 B2 | 5/2007 | Samain et al. |
| 7,243,664 B2 | 7/2007 | Berger et al. |
| 7,431,775 B2 | 10/2008 | Wang et al. |
| 7,448,255 B2 | 11/2008 | Hoots et al. |
| 7,498,051 B2 | 3/2009 | Man et al. |
| 7,541,324 B2 | 6/2009 | Reinhardt et al. |
| 7,569,232 B2 | 8/2009 | Man et al. |
| 7,569,528 B2 | 8/2009 | Lant et al. |
| 7,598,218 B2 | 10/2009 | Stolte et al. |
| 7,601,789 B2 | 10/2009 | Morris et al. |
| 7,618,545 B2 | 11/2009 | Wakao et al. |
| 7,686,892 B2 | 3/2010 | Smets et al. |
| 7,723,083 B2 | 5/2010 | DiCosimo et al. |
| 7,771,737 B2 | 8/2010 | Man et al. |
| 7,863,234 B2 | 1/2011 | Maki et al. |
| 7,875,720 B2 | 1/2011 | Morris et al. |
| 7,887,641 B2 | 2/2011 | Man et al. |
| 7,910,371 B2 | 3/2011 | Johnson |
| 7,915,445 B2 | 3/2011 | Maatta et al. |
| 7,919,122 B2 | 4/2011 | Okano et al. |
| 7,922,828 B2 | 4/2011 | Smith et al. |
| 7,949,432 B2 | 5/2011 | Rice |
| 7,981,679 B2 | 7/2011 | Rice |
| 7,985,318 B2 | 7/2011 | Shevchenko et al. |
| 8,017,409 B2 | 9/2011 | Tokhtuev et al. |
| 8,030,351 B2 | 10/2011 | Gutzmann et al. |
| 8,071,528 B2 | 12/2011 | Smith et al. |
| 8,080,404 B1 | 12/2011 | Turetsky et al. |
| 8,084,756 B2 | 12/2011 | Tokhtuev et al. |
| 8,110,603 B2 | 2/2012 | Kawabata et al. |
| 8,119,412 B2 | 2/2012 | Kraus |
| 8,153,573 B2 | 4/2012 | Miralles et al. |
| 8,178,336 B2 | 5/2012 | Derkx et al. |
| 8,226,939 B2 | 7/2012 | Herdt et al. |
| 8,231,917 B2 | 7/2012 | Herdt et al. |
| 8,236,573 B2 | 8/2012 | Tokhtuev et al. |
| 8,241,624 B2 | 8/2012 | Herdt et al. |
| 8,309,507 B2 | 11/2012 | Fernandez Prieto et al. |
| 2002/0055043 A1 | 5/2002 | Morikawa et al. |
| 2002/0064565 A1 | 5/2002 | Karagoezian |
| 2002/0157189 A1 | 10/2002 | Wang et al. |
| 2002/0188026 A1 | 12/2002 | Singh et al. |
| 2003/0100469 A1 | 5/2003 | Connor et al. |
| 2003/0235623 A1 | 12/2003 | Van Oosterom |
| 2004/0002616 A1 | 1/2004 | Preto et al. |
| 2004/0033269 A1 | 2/2004 | Hei et al. |
| 2004/0035537 A1 | 2/2004 | Delmas et al. |
| 2005/0000908 A1 | 1/2005 | Karlsson et al. |

(56) References Cited

U.S. PATENT DOCUMENTS

| | | | |
|---|---|---|---|
| 2005/0008526 A1 | 1/2005 | Bianchetti et al. |
| 2005/0226800 A1 | 10/2005 | Wang et al. |
| 2005/0281773 A1 | 12/2005 | Wieland et al. |
| 2006/0040847 A1 | 2/2006 | Weibel |
| 2006/0088498 A1 | 4/2006 | Martin et al. |
| 2006/0173209 A1 | 8/2006 | Vineyard et al. |
| 2006/0199742 A1 | 9/2006 | Arisz et al. |
| 2006/0254001 A1 | 11/2006 | Hoeffkes et al. |
| 2006/0257964 A1 | 11/2006 | Larose |
| 2006/0276366 A1 | 12/2006 | Deljosevic et al. |
| 2007/0042924 A1 | 2/2007 | DiCosimo et al. |
| 2007/0087954 A1 | 4/2007 | Wang et al. |
| 2007/0113875 A1 | 5/2007 | Wang et al. |
| 2007/0163779 A1 | 7/2007 | Rae et al. |
| 2007/0173430 A1 | 7/2007 | Souter et al. |
| 2007/0281002 A1 | 12/2007 | Morales et al. |
| 2008/0095861 A1 | 4/2008 | Walker |
| 2008/0176784 A1 | 7/2008 | Clowes et al. |
| 2008/0312107 A1 | 12/2008 | Harris et al. |
| 2009/0011971 A1 | 1/2009 | Evers |
| 2009/0018049 A1 | 1/2009 | Stolte et al. |
| 2009/0047176 A1 | 2/2009 | Cregger et al. |
| 2009/0061017 A1 | 3/2009 | Pedersen et al. |
| 2009/0088347 A1 | 4/2009 | Mukhopadhyay et al. |
| 2009/0148686 A1 | 6/2009 | Urankar et al. |
| 2009/0175956 A1 | 7/2009 | Buschmann et al. |
| 2009/0221704 A1 | 9/2009 | Aksela et al. |
| 2009/0249557 A1 | 10/2009 | Maki et al. |
| 2009/0269324 A1 | 10/2009 | Herdt et al. |
| 2009/0294382 A1 | 12/2009 | Fukuyo et al. |
| 2010/0021557 A1 | 1/2010 | Li et al. |
| 2010/0021558 A1 | 1/2010 | Dada et al. |
| 2010/0048730 A1 | 2/2010 | Li et al. |
| 2010/0084603 A1 | 4/2010 | Narayan et al. |
| 2010/0108566 A1 | 5/2010 | Scattergood et al. |
| 2010/0140186 A1 | 6/2010 | Huang et al. |
| 2010/0160449 A1* | 6/2010 | Rovison et al. ............... 514/714 |
| 2010/0222242 A1 | 9/2010 | Huang et al. |
| 2010/0227000 A1 | 9/2010 | Ames et al. |
| 2010/0286017 A1 | 11/2010 | Righetto |
| 2010/0308260 A1 | 12/2010 | Maki et al. |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |
| 2011/0217761 A1 | 9/2011 | Hilgren et al. |
| 2011/0240510 A1 | 10/2011 | De Poortere et al. |
| 2011/0257060 A1 | 10/2011 | Dykstra |
| 2012/0012307 A1 | 1/2012 | Nevin |
| 2012/0024525 A1 | 2/2012 | Svarczkopf et al. |
| 2012/0052134 A1 | 3/2012 | Li et al. |
| 2012/0070339 A1 | 3/2012 | Lawal |
| 2012/0085236 A1 | 4/2012 | McCorriston et al. |
| 2012/0085931 A1 | 4/2012 | Burns et al. |
| 2012/0097614 A1 | 4/2012 | Silva et al. |
| 2012/0149121 A1 | 6/2012 | Tokhtuev et al. |
| 2012/0172441 A1 | 7/2012 | Li et al. |
| 2012/0225943 A1 | 9/2012 | Gohl et al. |
| 2012/0321510 A1 | 12/2012 | Herdt et al. |
| 2013/0018097 A1 | 1/2013 | Bolduc et al. |

FOREIGN PATENT DOCUMENTS

| | | |
|---|---|---|
| CN | 100486668 | 3/2006 |
| CN | 102066240 | 5/2011 |
| CN | 102256484 | 11/2011 |
| DE | 1024514 | 2/1958 |
| DE | 19754290 | 6/1999 |
| EP | 0 075 419 | 3/1983 |
| EP | 0 061 393 | 10/1984 |
| EP | 0 068 547 | 9/1985 |
| EP | 0 231 632 | 8/1987 |
| EP | 0 233 730 | 8/1987 |
| EP | 0 267 047 | 5/1988 |
| EP | 0 280 697 | 9/1988 |
| EP | 0 384 911 | 8/1990 |
| EP | 0 395 902 | 11/1990 |
| EP | 0 396 341 | 11/1990 |
| EP | 0 442 549 | 8/1991 |
| EP | 0 626 371 | 4/1994 |
| EP | 0 741 776 | 11/1996 |
| EP | 0 751 210 | 1/1997 |
| EP | 0 845 526 | 6/1998 |
| EP | 0 906 950 | 4/1999 |
| EP | 0 751 933 | 6/1999 |
| EP | 1 001 012 | 5/2000 |
| EP | 1 010 749 | 6/2000 |
| EP | 1 247 802 | 12/2004 |
| EP | 1 931 628 | 6/2008 |
| EP | 2 271 410 | 1/2011 |
| EP | 2 329 893 | 6/2011 |
| EP | 2 522 714 | 11/2012 |
| EP | 2 522 715 | 11/2012 |
| GB | 1198734 | 7/1970 |
| GB | 1 584 170 | 2/1981 |
| JP | 62155203 | 7/1987 |
| JP | 5186989 | 7/1993 |
| JP | 6305920 | 11/1994 |
| JP | 2006045146 | 2/2006 |
| JP | 2006045147 | 2/2006 |
| WO | WO-90/07501 | 7/1990 |
| WO | 91/07375 | * 5/1991 |
| WO | WO-91/07375 | 5/1991 |
| WO | WO-91/13058 | 9/1991 |
| WO | WO-91/15474 | 10/1991 |
| WO | WO-94/03395 | 2/1994 |
| WO | WO-94/10284 | 5/1994 |
| WO | WO-94/13776 | 6/1994 |
| WO | WO-94/18299 | 8/1994 |
| WO | WO-94/24869 | 11/1994 |
| WO | WO-94/29509 | 12/1994 |
| WO | WO-95/02030 | 1/1995 |
| WO | WO-95/21122 | 10/1995 |
| WO | WO-95/21290 | 10/1995 |
| WO | WO-95/28471 | 10/1995 |
| WO | WO-95/28472 | 10/1995 |
| WO | WO-95/33816 | 12/1995 |
| WO | WO-96/14384 | 5/1996 |
| WO | WO-96/16148 | 5/1996 |
| WO | WO-97/43393 | 11/1997 |
| WO | WO-98/03513 | 1/1998 |
| WO | WO-98/11189 | 3/1998 |
| WO | WO-98/11777 | 3/1998 |
| WO | WO-98/18893 | 5/1998 |
| WO | WO-99/31215 | 6/1999 |
| WO | WO-99/32598 | 7/1999 |
| WO | WO-00/42145 | 7/2000 |
| WO | WO-00/70951 | 11/2000 |
| WO | WO-00/76963 | 12/2000 |
| WO | WO-00/78911 | 12/2000 |
| WO | WO-01/00765 | 1/2001 |
| WO | WO-01/19414 | 3/2001 |
| WO | WO-01/44176 | 6/2001 |
| WO | WO-01/70030 | 9/2001 |
| WO | WO-03/005818 | 1/2003 |
| WO | WO-03/050343 | 6/2003 |
| WO | WO-03/006581 | 10/2003 |
| WO | WO-2004/044266 | 5/2004 |
| WO | WO-2005/109981 | 5/2005 |
| WO | WO-2006/016145 | 2/2006 |
| WO | WO-2006/094232 | 9/2006 |
| WO | WO-2006/131503 | 12/2006 |
| WO | WO-2007/013324 | 2/2007 |
| WO | WO-2008/005058 | 1/2008 |
| WO | WO-2009/023492 | 2/2009 |
| WO | WO-2009/040769 | 4/2009 |
| WO | WO-2009/071664 | 6/2009 |
| WO | WO-2009/141548 | 11/2009 |
| WO | WO-2010/050634 | 5/2010 |
| WO | WO-2010/080274 | 7/2010 |
| WO | WO-2010/090125 | 8/2010 |
| WO | WO-2011/083295 | 7/2011 |

(56) References Cited

FOREIGN PATENT DOCUMENTS

| WO | WO-2011/089313 | 7/2011 |
| --- | --- | --- |
| WO | WO-2011/159859 | 12/2011 |
| WO | WO-2012/090124 | 7/2012 |

OTHER PUBLICATIONS

ECOLA8 USA, Inc. et al., PCT/IB2011/055830 filed Dec. 20, 2011, "Notification of Transmittal of The International Search Report and The Written Opinion of the International Searching Authority, or the Declaration" mailed Aug. 24, 2012, 8 pages.

ECOLA8 USA, Inc. et al., PCT/IB2011/055832 filed Dec. 20, 2011, "Notification of Transmittal of The International Search Report and The Written Opinion of the International Searching Authority, or the Declaration" mailed Aug. 14, 2012, 14 pages.

Effkemann, Stefan, et al., "Peroxide analysis in laundry detergents using liquid chromotography", Elsevier, Analytica Chimica Acta, 363 (1998) 97-103 (7 pages).

*Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2.

Katz, Jonathan, "Report: Fracking to Grow U.S. Water-Treatment Market Nine-Fold by 2020", http://www.industryweek.com/global-economy/report-fracking-grow-us-frack-water-treatment-market-nine-fold-2020, [retrieved from the internet on Jun. 6, 2012], pp. 1-2.

Lee, Jung Jin, et al., "Hydrolytic stability of a series of lactam-based cationic bleach activators and their impact on cellulose peroxide bleaching", Springer Science+Business Medica B.V., Cellulose (2010) 17:671-678 (8 pages).

Leistner (1995) In Gould GW (Ed.) *New Methods of Food Preservation*, Springer, pp. 1-21.

Leistner, "Basic aspects of food preservation by hurdle technology", *International Journal of Food Microbiology*, (2000) 55:181-186.

Leveneur, Sebastien, "Synthesis of peroxypropionic acid from propionic acid and hydrogen peroxide over heterogeneous catalysts", Elsevier, Chemical Engineering Journal, 147 (2009) 323-329 (7 pages).

Maeda, Hatsuo, et al., "Assessment of Acyl Groups and Reaction Conditions in the Competition between 6 Perhydrolysis and Hydrolysis of Acyl Resorufins for Developing an Indicator Reaction for Fluorometric Analysis of Hydrogen Peroxide", Pharmaceutical Society of Japan, Cehm. Pharm. Bull. 50(2) 169-174,2002 (6 pages).

Malow and Wehrstedt, "Prediction of the self-accelerating decomposition temperature (SADT) for liquid organic peroxides from differential scanning calorimetry (DSC) measurements", *J. Hazard Mater.* (2005) 120(1-3):21-4.

Muurinene, Esa, "Organosolv Pulping—A review and distillation study related to peroxyacid pulping", Department of Process Engineering, University of Oulu, May 16, 2000, Oulu, Finland (314 pages).

Ogata et al., "Radical scavenging activities of niacin-related compounds", *Biosci. Biotechnol. Biochem.*, 2002, 66(3), 641-645.

Ogata, Y., et al., "The Formation of Peracids by the Perhydrolysis With Alkaline Hydrogen Peroxide", Tetrochem, vol. 23, pp. 3327-3332, Pergamom Press, 1967 (7 pages).

"Recommendations on the Transport of Dangerous Goods, Model Regulations" (Rev.17) ST/SG/AC.10/1/Rev.17 (2011).

"Recommendations on the Transport of Dangerous Goods, Manual of Tests and Criteria", 5th revised edition (2009), UN , sect. 28.4.4, p. 314.

Rusch gen. Klaas, Mark, et al., "Lipase-catalyzed preparation of peroxy acids and their use for expoxidation", Elsevier, Journal of Molecular Catalysis A: Chemical117 (1997) 311-319 (9 pages).

Rusch gen. Klaas, Market al., "Biocatalylic peroxy acid formation for disinfection", Journal of Molecular Catalysis B: Enzymatic 19-20 (2002) 499-505.

Rusch gen. Klaas, Market al., "Lipase-catalyzed conversions of trimethylsilyl ethers: deprotection, acetylation, epoxidation and one-pot-multi-step reactions", Journal of Molecular Catalysis B: Enzymatic 7 (1999) 283-289.

Suchy, Miro, et al., "Improving Alkaline Peroxide Delignification Using a Vandium Activator", Papricay and Department of Chemistry, McGill University, Montreal, Quebec (15 pages).

U.S. Appl. No. 13/645,671 (2012).

Tsunokawa, Youko et al., "A Versatile Method for Preparation of 0-Aikylperoxycarbonic Acids: Epoxidation with Alkyloxycarbonylimidazoles and Hydrogen Peroxide", Tetrahedron Letters, vol. 23, No. 20, (1982), pp. 2113-2116.

Yin, De Lu (Tyler), et al., "Switching Catalysis from Hydrolysis to Perhydrolysis in Pseudomonas fluorescens Esterase", Biochemistry, (2010) 49:1931-1942.

Office Action for U.S. Appl. No. 13/785,405, mailed Feb. 20, 2014, 9 pages.

Chung et al., "Coordinative binding of divalent cations with ligands related to bacterial spores," Biophys J (1971) 11:470-482.

International Search Report and Written Opinion for PCT/US2013/063512, mailed Dec. 26, 2013, 10 pages.

Nowack, "Environmental chemistry of phosphonates," Water Res (2003) 37(11):2533-2546.

Popov et al., "Critical evaluation of stability constants of phosphonic acids," Pure Appl Chem (2001) 73(10):1641-1677.

Rizkalla et al., "Metal chelates of phosphonate-containing ligands-V Stability of some 1-hydroxyethane-1,1-diphosphonic acid metal chelates," Talanta (1980) 27(9):715-719.

Swern (ed.), Organic Peroxides, Wiley-Interscience, New York (1970) pp. 360-369.

Final Office Action for U.S. Appl. No. 14/339,556, issued Mar. 4, 2015, 11 pages.

Notification of the First Office Action (including translation) for CN 201380051957.2, mailed Nov. 24, 2015, 32 pages.

Supplementary European Search Report for EP 13844411.2, mailed Jan. 19, 2016, 7 pages.

Supplementary European Search Report for EP 15184379.4, mailed Jan. 19, 2016, 7 pages.

\* cited by examiner

Kinetic Viscosity Profile of POAA with Various Level of $H_2O_2$ in A Gel Fluid

STABLE PERCARBOXYLIC ACID COMPOSITIONS AND USES THEREOF

CROSS REFERENCES TO RELATED APPLICATIONS

This application claims the priority benefit of U.S. provisional application Ser. No. 61/710,631, filed Oct. 5, 2012, and entitled "Stable Peroxycarboxylic Acid Compositions and Uses Thereof;" and U.S. provisional application Ser. No. 61/762,777, filed Feb. 8, 2013, and entitled "Stable Peroxycarboxylic Acid Compositions and Uses Thereof." The present application also relates to U.S. provisional application Ser. No. 61/617,814, filed Mar. 31, 2012, and entitled "Use of Peracetic Acid/Hydrogen Peroxide and Catalase for Treatment of Drilling Fluids, FRAC Fluids, Flowback Water and Disposal Water;" U.S. application Ser. No. 13/331,104, filed Dec. 20, 2011, and entitled "Generation of Peroxycarboxylic Acids at Alkaline pH, and Their Use as Textile Bleaching and Antimicrobial Agents;" U.S. application Ser. No. 13/331,304, filed Dec. 20, 2011, and entitled "In Situ Generation of Peroxycarboxylic Acids at Alkaline pH, and Methods of Use Thereof;" and U.S. application Ser. No. 13/331,486, filed Dec. 20, 2011, and entitled "In Situ Generation of Peroxycarboxylic Acids at Alkaline pH, and Methods of Use Thereof." The contents of the above-referenced applications are incorporated by reference in their entireties.

TECHNICAL FIELD

The present invention relates generally to stable percarboxylic acid compositions comprising, inter alia, at least two stabilizing agents, and various uses for water treatments, including water treatments in connection with oil- and gas-field operations. The present invention also relates to slick water compositions and gel based compositions that comprise stable percarboxylic acid compositions and the use thereof in oil- and gas-field operations.

BACKGROUND OF THE INVENTION

Peroxycarboxylic acids are increasingly used as biocides in various fields owing to their broad biocidal efficacy and excellent environmental profiles. The most commonly used peroxycarboxylic acid is peracetic acid. Peracetic acid is a colorless, freely water soluble liquid which has great biocidal efficacy toward various microorganisms, such as bacteria, virus, yeast, fungi and spores. When decomposed, peracetic acid results in acetic acid (vinegar), water and oxygen. Pure peroxycarboxylic acids, such as peracetic acid, however, are unstable and explosive, and thus commercially available peroxycarboxylic acids are usually sold in an equilibrium solution. In addition to the peroxycarboxylic acid, an equilibrium solution also contains the corresponding carboxylic acid, hydrogen peroxide and water. Compared to the peroxycarboxylic acid, hydrogen peroxide only has negligible biocidal efficacy, but may pose environmental issues in some applications if it exceeds the specific release limitation. Furthermore, it has been disclosed that the presence of hydrogen peroxide has negative impacts on the efficacy of peroxycarboxylic acid toward some microorganisms.

In applications such as water treatment for use in fracturing drilling of oil and gas wells, the hydrogen peroxide that is in the peroxycarboxylic acid compositions may interact with other components used in the applications, such as gelling agents, friction reducers, corrosion inhibitors and scale inhibitors, etc. The presence of hydrogen peroxide in these solutions may cause the performance failure. Thus, there is a need to develop a peroxycarboxylic acid composition which has as high as possible peroxycarboxylic acid to hydrogen peroxide ratio for applications as a biocide in general, and in particular for water treatment in oil and gas drilling.

Commercially available peroxycarboxylic acid compositions generally have significantly less, or roughly equal, weight amounts of peroxycarboxylic acid than hydrogen peroxide. It is known that among other factors, the ratio of hydrogen peroxide to peroxycarboxylic acid plays a significant role in the stability of the peroxycarboxylic acid compositions. The higher the ratio of hydrogen peroxide to peroxycarboxylic acid, the more stable of the composition. Some commonly available peroxycarboxylic acid compositions have a ratio of about 1.5 to 1 hydrogen peroxide to peroxycarboxylic acid. While compositions with higher ratio of peroxycarboxylic acid to hydrogen peroxide are commercially available, these compositions are in small packaging sizes limited by self accelerating decomposition temperature (SADT) transportation limitations and require controlled temperature storage due to the limited stability of the compositions.

Various stabilizers are used in peroxycarboxylic acid compositions to stabilize the compositions. For example, pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts, are used. When used individually at the right level, these stabilizers can significantly improve the stability of the peroxycarboxylic acid compositions, and for the conventional peroxycarboxylic acid compositions, the stability profile achieved with these stabilizers allows for the commercial use of these compositions. For peroxycarboxylic acid compositions with high ratios of peroxycarboxylic acid to hydrogen peroxide, the extra stability challenge cannot be met by these stabilizers used in the traditional matter.

BRIEF SUMMARY OF THE INVENTION

The present invention relates to stable percarboxylic acid compositions and uses thereof. In some embodiments, the present invention relates to a stable peracid composition with high ratio of peracid to hydrogen peroxide. Optionally, the level of hydrogen peroxide is further reduced by adding a catalase or peroxidase either in use solution, or in the diluted concentrate prior to use. The compositions disclosed are particularly useful in treating the water for use in fracturing drilling of oil and gas well.

In one aspect, the present invention is directed to a composition, which composition comprises:
1) a $C_1$-$C_{22}$ carboxylic acid;
2) a $C_1$-$C_{22}$ percarboxylic acid;
3) hydrogen peroxide;
4) a first stabilizing agent, which is a picolinic acid or a compound having the following Formula (IA):

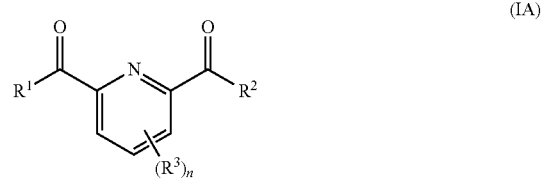

wherein
R¹ is OH or —NR$^{1a}$R$^{1b}$, wherein R$^{1a}$ and R$^{1b}$ are independently hydrogen or ($C_1$-$C_6$)alkyl;
R² is OH or —NR$^{2a}$R$^{2b}$, wherein R$^{2a}$ and R$^{2b}$ are independently hydrogen or ($C_1$-$C_6$)alkyl;
each R³ is independently ($C_1$-$C_6$)alkyl, ($C_2$-$C_6$)alkenyl or ($C_2$-$C_6$)alkynyl; and
n is a number from zero to 3;
or a salt thereof;
or a compound having the following Formula (IB):

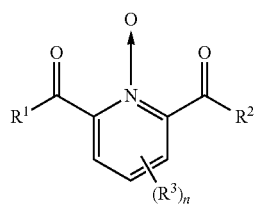

(IB)

wherein
R¹ is OH or —NR$^{1a}$R$^{1b}$, wherein R$^{1a}$ and R$^{1b}$ are independently hydrogen or ($C_1$-$C_6$)alkyl;
R² is OH or —NR$^{2a}$R$^{2b}$, wherein R$^{2a}$ and R$^{2b}$ are independently hydrogen or ($C_1$-$C_6$)alkyl;
each R³ is independently ($C_1$-$C_6$)alkyl, ($C_2$-$C_6$)alkenyl or ($C_2$-$C_6$)alkynyl; and
n is a number from zero to 3;
or a salt thereof;
5) a second stabilizing agent, which is a compound having the following Formula (IIA):

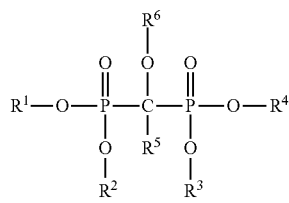

(IIA)

wherein
R¹, R², R³, and R⁴ are independently hydrogen, ($C_1$-$C_6$) alkyl, ($C_2$-$C_6$)alkenyl or ($C_2$-$C_6$)alkynyl, or $C_{6-20}$ aryl;
R⁵ is ($C_1$-$C_6$)alkyl, ($C_2$-$C_6$)alkenyl or ($C_2$-$C_6$)alkynyl; and
R⁶ is hydrogen, ($C_1$-$C_6$)alkyl, ($C_2$-$C_6$)alkenyl or ($C_2$-$C_6$) alkynyl;
or a salt thereof;
or a compound having the following Formula (IIB):

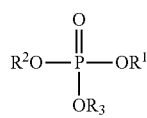

(IIB)

wherein
R¹, R², and R³ are independently hydrogen, ($C_1$-$C_6$) alkyl, ($C_2$-$C_6$)alkenyl or ($C_2$-$C_6$)alkynyl, or $C_{6-20}$ aryl;
or a salt thereof; and
wherein said hydrogen peroxide has a concentration of at least about 0.1 wt-%, the $C_1$-$C_{22}$ percarboxylic acid has a concentration of at least about 2 times of the concentration of said hydrogen peroxide, and said composition has a pH at about 4 or less.

In another aspect, the present invention is directed to a method for storing a percarboxylic acid containing composition, which method comprises storing the above composition, wherein said composition retains at least about 80% of the $C_1$-$C_{22}$ percarboxylic acid activity after storage of about 30 days at about 50° C.

In still another aspect, the present invention is directed to a method for transporting a percarboxylic acid containing composition, which method comprises transporting the above composition, preferably in bulk, wherein the SADT of said composition is elevated to at least 45° C. during transportation.

In yet another aspect, the present invention is directed to a method for treating water, which method comprises providing the above composition to a water source in need of treatment to form a treated water source, wherein said treated water source comprises from about 1 ppm to about 1,000 ppm of said $C_1$-$C_{22}$ percarboxylic acid.

In yet another aspect, the present invention is directed to a method for treating a target, which method comprises a step of contacting a target with the above composition in a diluted level to form a treated target composition, wherein said treated target composition comprises from about 1 ppm to about 10,000 ppm of said $C_1$-$C_{22}$ percarboxylic acid, and said contacting step lasts for sufficient time to stabilize or reduce microbial population in and/or on said target or said treated target composition.

In yet another aspect, the present invention is directed to a method for reducing the level of hydrogen sulfide ($H_2S$), hydrosulfuric acid or a salt thereof in a water source, which method comprises a step of contacting a water source with the above composition in a diluted level to form a treated water source, wherein said treated water source comprises from about 1 ppm to about 10,000 ppm of said $C_1$-$C_{22}$ percarboxylic acid, and said contacting step lasts for sufficient time to stabilize or reduce the level of $H_2S$, hydrosulfuric acid or a salt thereof in said treated water source.

The present invention also relates to slick water compositions useful in oil and/or gas drilling that comprise stable percarboxylic acid compositions and uses thereof. In one aspect, the present invention is directed to a composition, which composition comprises:
1) a $C_1$-$C_{22}$ carboxylic acid;
2) a $C_1$-$C_{22}$ percarboxylic acid;
3) hydrogen peroxide;
4) a first stabilizing agent, which is a picolinic acid or a compound having the following Formula (IA):

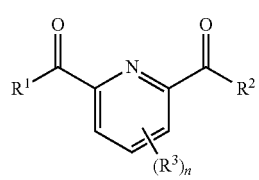

(IA)

wherein
R¹ is OH or —NR¹ᵃR¹ᵇ, wherein R¹ᵃ and R¹ᵇ are independently hydrogen or $(C_1-C_6)$alkyl;
R² is OH or —NR²ᵃR²ᵇ, wherein R²ᵃ and R²ᵇ are independently hydrogen or $(C_1-C_6)$alkyl;
each R³ is independently $(C_1-C_6)$alkyl, $(C_2-C_6)$alkenyl or $(C_2-C_6)$alkynyl; and
n is a number from zero to 3;
or a salt thereof;
or a compound having the following Formula (IB):

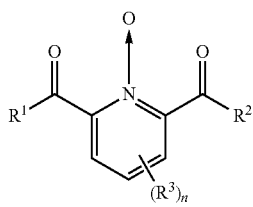

wherein
R¹ is OH or —NR¹ᵃR¹ᵇ, wherein R¹ᵃ and R¹ᵇ are independently hydrogen or $(C_1-C_6)$alkyl;
R² is OH or —NR²ᵃR²ᵇ, wherein R²ᵃ and R²ᵇ are independently hydrogen or $(C_1-C_6)$alkyl;
each R³ is independently $(C_1-C_6)$alkyl, $(C_2-C_6)$alkenyl or $(C_2-C_6)$alkynyl; and
n is a number from zero to 3;
or a salt thereof;
5) a second stabilizing agent, which is a compound having the following Formula (IIA):

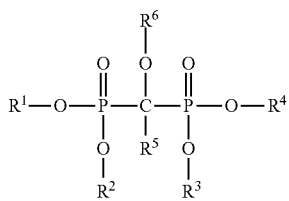

wherein
R¹, R², R³, and R⁴ are independently hydrogen, $(C_1-C_6)$alkyl, $(C_2-C_6)$alkenyl or $(C_2-C_6)$alkynyl, or $C_{6-20}$ aryl;
R⁵ is $(C_1-C_6)$alkyl, $(C_2-C_6)$alkenyl or $(C_2-C_6)$alkynyl; and
R⁶ is hydrogen, $(C_1-C_6)$alkyl, $(C_2-C_6)$alkenyl or $(C_2-C_6)$alkynyl;
or a salt thereof;
or a compound having the following Formula (IIB):

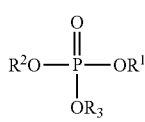

wherein
R¹, R², and R³ are independently hydrogen, $(C_1-C_6)$alkyl, $(C_2-C_6)$alkenyl or $(C_2-C_6)$alkynyl, or $C_{6-20}$ aryl;
or a salt thereof;

6) a friction reducer; and
wherein said hydrogen peroxide has a concentration of about 1 ppm to about 20 ppm, and the $C_1-C_{22}$ percarboxylic acid has a concentration of at least about 2 times of the concentration of said hydrogen peroxide.

In another aspect, the present invention is directed to a method for slick water fracturing, which method comprises directing the above composition into a subterranean environment.

The present invention further relates to gel based compositions useful in oil and/or gas drilling that comprise stable percarboxylic acid compositions and uses thereof. In one aspect, the present invention is directed to a composition, which composition comprises:

1) a $C_1-C_{22}$ carboxylic acid;
2) a $C_1-C_{22}$ percarboxylic acid;
3) hydrogen peroxide;
4) a first stabilizing agent, which is a picolinic acid or a compound having the following Formula (IA):

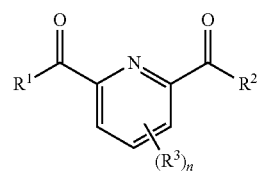

wherein
R¹ is OH or —NR¹ᵃR¹ᵇ, wherein R¹ᵃ and R¹ᵇ are independently hydrogen or $(C_1-C_6)$alkyl;
R² is OH or —NR²ᵃR²ᵇ, wherein R²ᵃ and R²ᵇ are independently hydrogen or $(C_1-C_6)$alkyl;
each R³ is independently $(C_1-C_6)$alkyl, $(C_2-C_6)$alkenyl or $(C_2-C_6)$alkynyl; and
n is a number from zero to 3;
or a salt thereof;
or a compound having the following Formula (IB):

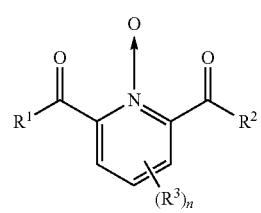

wherein
R¹ is OH or —NR¹ᵃR¹ᵇ, wherein R¹ᵃ and R¹ᵇ are independently hydrogen or $(C_1-C_6)$alkyl;
R² is OH or —NR²ᵃR²ᵇ, wherein R²ᵃ and R²ᵇ are independently hydrogen or $(C_1-C_6)$alkyl;
each R³ is independently $(C_1-C_6)$alkyl, $(C_2-C_6)$alkenyl or $(C_2-C_6)$alkynyl; and
n is a number from zero to 3;
or a salt thereof;

5) a second stabilizing agent, which is a compound having the following Formula (IIA):

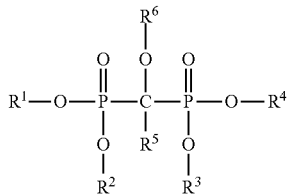

(IIA)

wherein
$R^1$, $R^2$, $R^3$, and $R^4$ are independently hydrogen, $(C_1-C_6)$ alkyl, $(C_2-C_6)$alkenyl or $(C_2-C_6)$alkynyl, or $C_{6-20}$ aryl;
$R^5$ is $(C_1-C_6)$alkyl, $(C_2-C_6)$alkenyl or $(C_2-C_6)$alkynyl; and
$R^6$ is hydrogen, $(C_1-C_6)$alkyl, $(C_2-C_6)$alkenyl or $(C_2-C_6)$ alkynyl;
or a salt thereof;
or a compound having the following Formula (IIB):

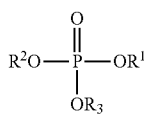

(IIB)

wherein
$R^1$, $R^2$, and $R^3$ are independently hydrogen, $(C_1-C_6)$alkyl, $(C_2-C_6)$alkenyl or $(C_2-C_6)$alkynyl, or $C_{6-20}$ aryl;
or a salt thereof;
6) a viscosity enhancer; and
wherein said hydrogen peroxide has a concentration of about 1 ppm to about 15 ppm, and said $C_1-C_{22}$ percarboxylic acid has a concentration of at least about 2 times of the concentration of said hydrogen peroxide.

In another aspect, the present invention is directed to a method for high-viscosity fracturing, which method comprises directing the above composition into a subterranean environment.

DETAILED DESCRIPTION OF THE INVENTION

Figure 1:
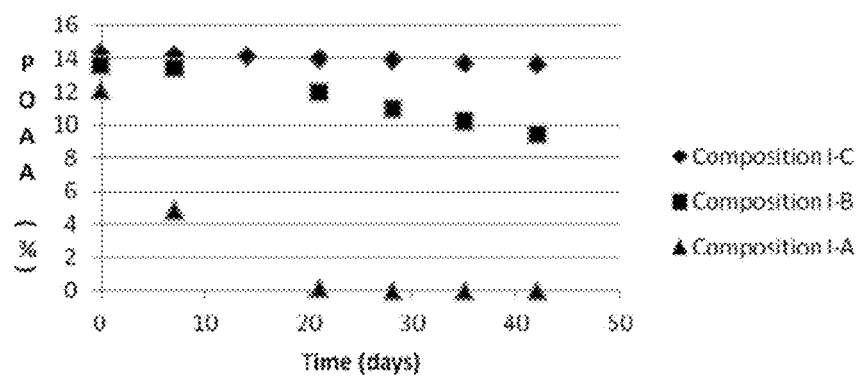
FIG. 1 illustrates stability of peracetic acid compositions with various stabilizers.

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

The embodiments of this invention are not limited to particular peroxycarboxylic acid compositions and methods for using the same, which can vary and are understood by skilled artisans. It is further to be understood that all terminology used herein is for the purpose of describing particular embodiments only, and is not intended to be limiting in any manner or scope. For example, all units, prefixes, and symbols may be denoted in its SI accepted form. Numeric ranges recited within the specification are inclusive of the numbers defining the range and include each integer within the defined range.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "free," "no," "substantially no" or "substantially free" refers to a composition, mixture, or ingredient that does not contain a particular compound or to which a particular compound or a particular compound-containing compound has not been added. In some embodiments, the reduction and/or elimination of hydrogen peroxide according to embodiments provide hydrogen peroxide-free or substantially-free compositions. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "water" for treatment according to the invention includes a variety of sources, such as freshwater, pond water, sea water, salt water or brine source, brackish water, recycled water, or the like. Waters are also understood to optionally include both fresh and recycled water sources (e.g. "produced waters"), as well as any combination of waters for treatment according to the invention. In some embodiments, produced water (or reuse water) refers to a mixture of water that comprises both water recycled from previous or concurrent oil- and gas-field operations, e.g., fracking, and water that has not been used in oil- and gas-field operations, e.g., fresh water, pond water, sea water, etc.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

B. STABLE PERCARBOXYLIC ACID COMPOSITIONS AND USES THEREOF

The present invention relates to stable percarboxylic acid compositions and uses thereof. In one aspect, the present invention is directed to a composition, which composition comprises:

a $C_1$-$C_{22}$ carboxylic acid;

a $C_1$-$C_{22}$ percarboxylic acid;

hydrogen peroxide;

a first stabilizing agent, which is a picolinic acid or a compound having the following Formula (IA):

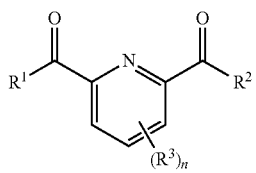
(IA)

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
or a compound having the following Formula (IB):

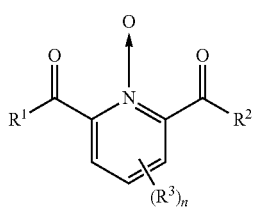
(IB)

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
a second stabilizing agent, which is a compound having the following Formula (IIA):

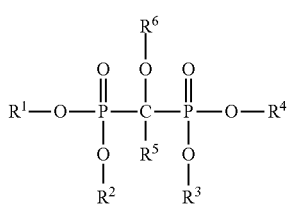
(IIA)

wherein
$R^1$, $R^2$, $R^3$, and $R^4$ are independently hydrogen, ($C_1$-$C_6$)alkyl, ($C_2$-$C_6$)alkenyl or ($C_2$-$C_6$)alkynyl, or $C_{6-20}$ aryl;
$R^5$ is ($C_1$-$C_6$)alkyl, ($C_2$-$C_6$)alkenyl or ($C_2$-$C_6$)alkynyl; and
$R^6$ is hydrogen, ($C_1$-$C_6$)alkyl, ($C_2$-$C_6$)alkenyl or ($C_2$-$C_6$)alkynyl;
or a salt thereof;
or a compound having the following Formula (IIB):

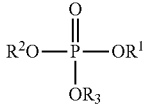
(IIB)

wherein
$R^1$, $R^2$, and $R^3$ are independently hydrogen, ($C_1$-$C_6$)alkyl, ($C_2$-$C_6$)alkenyl or ($C_2$-$C_6$)alkynyl, or $C_{6-20}$ aryl;
or a salt thereof; and
wherein said hydrogen peroxide has a concentration of at least about 0.1 wt-%, the $C_1$-$C_{22}$ percarboxylic acid has a concentration of at least about 2 times of the concentration of said hydrogen peroxide, and said composition has a pH at about 4 or less.

In some embodiments, the present composition is an equilibrated composition that comprises peracid, hydrogen peroxide, carboxylic acid and a solvent, e.g., water. In some embodiments, the present composition does not comprise a mineral acid, e.g., the mineral acids disclosed in WO 91/07375.

The $C_1$-$C_{22}$ percarboxylic acid can be used at any suitable concentration relative to the concentration of the hydrogen peroxide. In some embodiments, the $C_1$-$C_{22}$ percarboxylic acid has a concentration of at least about 6 times of the concentration of the hydrogen peroxide. In other embodiments, the $C_1$-$C_{22}$ percarboxylic acid has a concentration of at least about 10 times of the concentration of the hydrogen peroxide. In still other embodiments, the $C_1$-$C_{22}$ percarboxylic acid has a concentration of at least about 6, 7, 8, 9 or 10 times of the concentration of the hydrogen peroxide.

Carboxylic Acid

The present invention includes a carboxylic acid with the peracid composition and hydrogen peroxide. A carboxylic acid includes any compound of the formula R—(COOH)$_n$ in which R can be hydrogen, alkyl, alkenyl, alkyne, acylic, alicyclic group, aryl, heteroaryl, or heterocyclic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined below with respect to peracids.

Examples of suitable carboxylic acids according to the equilibrium systems of peracids according to the invention include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect of the invention, a particularly well suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid.

Additional examples of suitable carboxylic acids are employed in sulfoperoxycarboxylic acid or sulfonated peracid systems, which are disclosed in U.S. Patent Publication Nos. 2010/0021557, 2010/0048730 and 2012/0052134 herein incorporated by reference in their entireties.

Any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic acid is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ carboxylic acid comprises acetic acid, octanoic acid and/or sulfonated oleic acid.

The $C_1$-$C_{22}$ carboxylic acid can be used at any suitable concentration. In some embodiments, the $C_1$-$C_{22}$ carboxylic acid has a concentration from about 10 wt-% to about 90 wt-%. In other embodiments, the $C_1$-$C_{22}$ carboxylic acid has a concentration from about 20 wt-% to about 80 wt-%. In still other embodiments, the $C_1$-$C_{22}$ carboxylic acid has a concentration at about 10 wt-%, 20 wt-%, 30 wt-%, 40 wt-%, 50 wt-%, 60 wt-%, 70 wt-%, 80 wt-%, or 90 wt-%.

Peracids

In some aspects, a peracid is included for antimicrobial efficacy in the compositions. As used herein, the term "peracid" may also be referred to as a "percarboxylic acid" or "peroxyacid." Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Patent Publication Nos. 2010/0021557, 2010/0048730 and 2012/0052134 which are incorporated herein by reference in their entireties. A peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" includes a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like. The term "alkyl" or "alkyl groups" also refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

In some embodiments, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —SO$_3$H, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

In some embodiments, aryl and heteroaryl groups can be unsubstituted or substituted on the ring by, for example, aryl, heteroaryl, alkyl, alkenyl, alkoxy, amino, carboxy, halo, nitro, cyano, —SO$_3$H, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic and percarboxylic acids (e.g. C1-22) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, or sodium alcoholate. Alternatively, peracids can be prepared through non-equilibrium reactions, which may be generated for use in situ, such as the methods disclosed in U.S. patent application Ser. Nos. 13/331,304 and 13/331,486 each titled "In Situ Generation of Peroxycarboxylic Acids at Alkaline pH, and Methods of Use Thereof," which are incorporated herein by reference. Preferably a composition of the invention includes peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with hydroxy. Methods of preparing peroxyacetic acid are known to those of skill in the art including those disclosed in U.S. Pat. No. 2,833,813, which is herein incorporated herein by reference.

In another embodiment, a sulfoperoxycarboxylic acid has the following formula:

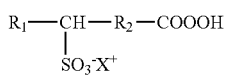

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In additional embodiments, a sulfoperoxycarboxylic acid is combined with a single or mixed peroxycarboxylic acid composition, such as a sulfoperoxycarboxylic acid with peroxyacetic acid and peroxyoctanoic acid .(PSOA/POOA/POAA).

In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid. Other combinations of mixed peracids are well suited for use in the current invention.

In another embodiment, a mixture of peracetic acid and peroctanoic acid is used to treat a water source, such as disclosed in U.S. Pat. No. 5,314,687 which is herein incorporated by reference in its entirety. In an aspect, the peracid mixture is a hydrophilic peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are used to treat a water source, such as disclosed in U.S. Patent Publication No. 2010/00021557 which is incorporated herein by reference in its entirety. A combination of the three peracids provides significant antimicrobial synergy providing an efficient antimicrobial composition for the water treatment methods according to the invention. In addition, it is thought the high acidity built in the composition assists in removing chemical contaminants from the water (e.g. sulfite and sulfide species).

Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example, peracetic acid (15%) available as EnviroSan (EcolabInc., St. Paul Minn.). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

Any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ percarboxylic acid comprises peroxyacetic acid, peroxyoctanoic acid and/or peroxysulfonated oleic acid.

The $C_1$-$C_{22}$ percarboxylic acid can be used at any suitable concentration. In some embodiments, the $C_1$-$C_{22}$ percarboxylic acid has a concentration from about 1 wt-% to about 40 wt-%. In other embodiments, the $C_1$-$C_{22}$ percarboxylic acid has a concentration from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%.

Hydrogen Peroxide

The present invention includes the use of hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In one aspect of the invention, hydrogen peroxide is initially in an antimicrobial peracid composition in an amount effective for maintaining an equilibrium between a carboxylic acid, hydrogen peroxide, a solvent such as water, and a peracid. The amount of hydrogen peroxide should not exceed an amount that would adversely affect the antimicrobial activity of a composition of the invention. In further aspects of the invention, hydrogen peroxide concentration is significantly reduced within an antimicrobial peracid composition, preferably containing hydrogen peroxide at a concentration as close to zero as possible. That is, the concentration of hydrogen peroxide is minimized, through the use of a selected catalase or peroxidase enzymes according to the invention. In further aspects, the concentration of hydrogen peroxide is reduced and/or eliminated as a result of distilled equilibrium peracid compositions, other catalysts for hydrogen peroxide decomposition (e.g. biomimetic complexes) and/or the use of anionic perhydrolysis of esters (e.g. triacetin) to obtain peracids with very low hydrogen peroxide.

In some embodiments, an advantage of minimizing the concentration of hydrogen peroxide is that antimicrobial activity of a composition of the invention is improved as compared to conventional equilibrium peracid compositions. Without being limited to a particular theory of the invention, significant improvements in antimicrobial efficacy result from enhanced peracid stability from the reduced hydrogen peroxide concentration in use solution.

The hydrogen peroxide can be used at any suitable concentration. In some embodiments, the hydrogen peroxide has a concentration from about 0.5 wt-% to about 10 wt-%. In other embodiments, the hydrogen peroxide has a concentration from about 1 wt-% to about 2 wt-%. In still other embodiments, the hydrogen peroxide has a concentration at about 0.5 wt-%, 1 wt-%, 2 wt-%, 3 wt-%, 4 wt-%, 5 wt-%, 6 wt-%, 7 wt-%, 8 wt-%, 9 wt-%, or 10 wt-%. In yet other embodiments, the hydrogen peroxide has a concentration at about 1 wt-%, 1.1 wt-%, 1.2 wt-%, 1.3 wt-%, 1.4 wt-%, 1.5 wt-%, 1.6 wt-%, 1.7 wt-%, 1.8 wt-%, 1.9 wt-%, or 2 wt-%.

In some embodiments, the $C_1$-$C_{22}$ carboxylic acid is acetic acid and the $C_1$-$C_{22}$ percarboxylic acid is peracetic acid. In other embodiments, the $C_1$-$C_{22}$ carboxylic acid, e.g., acetic acid, has a concentration of about 70 wt-%, the $C_1$-$C_{22}$ percarboxylic acid, e.g., peracetic acid, has a concentration of about 15 wt-%, and the hydrogen peroxide has a concentration of at least about 1 wt-%.

Stabilizing Agents

In some aspects, more than one type of stabilizer is used in the compositions. In some embodiments, at least one stabilizer is a phosphonic acid or a derivative thereof. Without wishing to be bound by any particular theory, it is thought that in addition to functioning as a stabilizer through the chelating of transition metal ions, phosphonic acid based stabilizers such as HEDP, also act as an acid catalyst and aid in the formation of the peroxycarboxylic acid from the corresponding carboxylic acid and hydrogen peroxide. In some embodiments, a pyridine carboxylic acid based stabilizer is used as a second stabilizer. Pyridine carboxylic acids such as 2,6-pyridinedicarboxylic acid (DPA), are well known chelators for metal ions. It is thought that by using two different types of stabilizers, the transition metals responsible for the catalytic decomposition of peroxycarboxylic acids are more efficiently deactivated by forming a more stable complex(es) involving both chelators.

Any suitable first stabilizing agent can be used in the present compositions. In some embodiments, the first stabilizing agent is a picolinic acid, or a salt thereof. In other embodiments, the first stabilizing agent is 2,6-pyridinedicarboxylic acid, or a salt thereof. The first stabilizing agent can be used at any suitable concentration. In some embodiments, the first stabilizing agent has a concentration from about 0.005 wt-% to about 5 wt-%. In other embodiments, the first stabilizing agent has a concentration from about 0.05 wt-% to about 0.15 wt-%. In still other embodiments, the first stabilizing agent has a concentration at about 0.005 wt-%, 0.01 wt-%, 0.1 wt-%, 1 wt-%, 2 wt-%, 3 wt-%, 4 wt-%, or 5 wt-%. In yet other embodiments, the first stabilizing agent has a concentration at about 0.05 wt-%, 0.06 wt-%, 0.07 wt-%, 0.08 wt-%, 0.09 wt-%, 0.10 wt-%, 0.11 wt-%, 0.12 wt-%, 0.13 wt-%, 0.14 wt-%, or 0.15 wt-%.

Any suitable second stabilizing agent can be used in the present compositions. In some embodiments, the second stabilizing agent is 1-hydroxy ethylidene-1,1-diphosphonic acid (HEDP), or a salt thereof. The second stabilizing agent can be used at any suitable concentration. In some embodiments, the second stabilizing agent has a concentration from about 0.1 wt-% to about 10 wt-%, e.g., 0.1 wt-%, 0.5 wt-%, 1 wt-%, 2 wt-%, 3 wt-%, 4 wt-%, 5 wt-%, 6 wt-%, 7 wt-%, 8 wt-%, 9 wt-%, or 10 wt-%. In other embodiments, the second stabilizing agent has a concentration from about 0.5 wt-% to about 5 wt-%, e.g., 0.5 wt-%, 1 wt-%, 1.5 wt-%, 2 wt-%, 2.5 wt-%, 3 wt-%, 3.5 wt-%, 4 wt-%, 4.5 wt-% or 5 wt-%. In still other embodiments, the second stabilizing agent has a concentration from about 0.6 wt-% to about 1.8 wt-%, e.g., 0.6 wt-%, 0.7 wt-%, 0.8 wt-%, 0.9 wt-%, 1.0 wt-%, 1.1 wt-%, 1.2 wt-%, 1.3 wt-%, 1.4 wt-%, 1.5 wt-%, 1.6 wt-%, 1.7 wt-%, 1.8 wt-%.

In some embodiments, the present composition can further comprise a substance that aids solubilization of the first and/or second stabilizing agent(s). Exemplary substances that can aid solubilization of the first and/or second stabilizing agent(s) include hydrotropes such as sodium xylene sulfonate, sodium cumene sulfonates, and surfactants, such as anionic surfactants and noinionic surfactants.

In some embodiments, the first stabilizing agent is a 2,6-pyridinedicarboxylic acid, or a salt thereof, and the second stabilizing agent is HEDP, or a salt thereof. In other embodiments, the first and second stabilizing agents act synergistically to delay or prevent the composition from meeting its self-accelerating decomposition temperature (SADT). SADT refers to the lowest temperature at which self-accelerating decomposition may occur with a composition. In some embodiments, SADT refers to the lowest temperature at which self-accelerating decomposition may occur under the commercial packaging, storage, transportation and/or use condition(s). SADT can be estimated, calculated, predicted and/or measured by any suitable methods. For example, SADT can be estimated, or measured directly by one of 3 methods (H1, H2 and H4) recommended by UN Committee for the Transportation of Dangerous Goods in "Recommendations on the Transport of Dangerous Goods, Model Regulations" (Rev.17) ST/SG/AC.10/1/Rev.17. For example, the methodology disclosed in Malow and Wehrstedt, *J. Hazard Mater.*, 120(1-3):21-4 (2005) can be used.

The present compositions can retain any suitable level or percentage of the $C_1$-$C_{22}$ percarboxylic acid activity under the usual packaging, storage, transportation and/or use condition(s). In some embodiments, the present compositions retain at least about 80% of the $C_1$-$C_{22}$ percarboxylic acid activity after storage of about 30 days at about 50° C. Preferably, the present compositions retain at least about 85%, 90% or higher percentage of the $C_1$-$C_{22}$ percarboxylic acid activity after storage of about 30 days at about 50° C.

Additional Optional Materials

The present compositions can optionally include additional ingredients to enhance the composition for water treatment according to the invention, including for example, friction reducers, viscosity enhancers and the like. Additional optional functional ingredients may include for example, peracid stabilizers, emulsifiers, corrosion inhibitors and/or descaling agents (i.e. scale inhibitors), surfactants and/or additional antimicrobial agents for enhanced efficacy (e.g. mixed peracids, biocides), antifoaming agents, acidulants (e.g. strong mineral acids), additional carboxylic acids, and the like. In an embodiment, no additional functional ingredients are employed.

Friction Reducers

Friction reducers are used in water or other water-based fluids used in hydraulic fracturing treatments for subterranean well formations in order to improve permeability of the desired gas and/or oil being recovered from the fluid-conductive cracks or pathways created through the fracking process.

The friction reducers allow the water to be pumped into the formations more quickly. Various polymer additives have been widely used as friction reducers to enhance or modify the characteristics of the aqueous fluids used in well drilling, recovery and production applications.

Examples of commonly used friction reducers include polyacrylamide polymers and copolymers. In an aspect, additional suitable friction reducers may include acrylamide-derived polymers and copolymers, such as polyacrylamide (sometime abbreviated as PAM), acrylamide-acrylate (acrylic acid) copolymers, acrylic acid-methacrylamide copolymers, partially hydrolyzed polyacrylamide copolymers (PHPA), partially hydrolyzed polymethacrylamide, acrylamide-methyl-propane sulfonate copolymers (AMPS) and the like. Various derivatives of such polymers and copolymers, e.g., quaternary amine salts, hydrolyzed versions, and the like, should be understood to be included with the polymers and copolymers described herein.

Friction reducers are combined with water and/or other aqueous fluids, which in combination are often referred to as "slick water" fluids. Slick water fluids have reduced frictional drag and beneficial flow characteristics which enable the pumping of the aqueous fluids into various gas- and/or oil-producing areas, including for example for fracturing.

In an aspect of the invention, a friction reducer is present in a use solution in an amount between about 100 ppm to 1,000 ppm. In a further aspect, a friction reducer is present in a use solution in an amount of at least about 0.01 wt-% to about 10 wt-%, preferably at least about 0.01 wt-% to about 5 wt-%, preferably at least about 0.01 wt-% to about 1 wt-%, more preferably at least about 0.01 wt-% to about 0.5 wt-%, and still more preferably at least about 0.01 wt-% to about 0.1 wt-%. Beneficially, the compositions and methods of the invention do not negatively interfere with friction reducers included in an aqueous solution. Without being limited to a particular theory of the invention, it is thought that the reduction and/or elimination of the oxidant hydrogen peroxide from the peracid composition promotes the stability and efficacy of any variation in the amount of friction reducer present in a use solution.

Viscosity Enhancers

Viscosity enhancers are additional polymers used in water or other water-based fluids used in hydraulic fracturing treatments to provide viscosity enhancement. Natural and/or synthetic viscosity-increasing polymers may be employed in compositions and methods according to the invention. Viscosity enhancers may also be referred to as gelling agents and examples include guar, xanthan, cellulose derivatives and polyacrylamide and polyacrylate polymers and copolymers, and the like.

In an aspect of the invention, a viscosity enhancer is present in a use solution in an amount between about 100 ppm to 1,000 ppm. In a further aspect, a viscosity enhancer is present in a use solution in an amount of at least about 0.01 wt-% to about 10 wt-%, preferably at least about 0.01 wt-% to about 5 wt-%, preferably at least about 0.01 wt-% to about 1 wt-%, at least about 0.01 wt-% to about 2 wt-%, preferably at least about 0.01 wt-% to about 1 wt-%, preferably at least about 0.01 wt-% to about 0.5 wt-%. Beneficially, the compositions and methods of the invention do not negatively interfere with viscosity enhancer included in an aqueous solution. Without being limited to a particular theory of the invention, it is believed the reduction and/or elimination of the oxidant hydrogen peroxide from the peracid composition promotes the stability and efficacy of any variation in the amount of viscosity enhancer present in a use solution.

Corrosion Inhibitors

Corrosion inhibitors are additional molecules used in oil and gas recovery operations. Corrosion inhibitors that may be employed in the present disclosure include the exemplary corrosion inhibitors disclosed in U.S. Pat. No. 5,965,785, U.S. patent application Ser. No. 12/263,904, GB Pat. No. 1,198,734, WO/03/006581, WO04/044266, and WO08/005,058, each incorporated herein by reference in their entireties.

In an aspect of the invention, a corrosion inhibitor is present in a use solution in an amount between about 100 ppm to 1,000 ppm. In a further aspect, a corrosion inhibitor is present in a use solution in an amount of at least about 0.0001 wt-% to about 10 wt-%, preferably at least about 0.0001 wt-% to about 5 wt-%, preferably at least about 0.0001 wt-% to about 1 wt-%, preferably at least about 0.0001 wt-% to about 0.1 wt-%, and still more preferably at least about 0.0001 wt-% to about 0.05 wt-%. Beneficially, the compositions and methods of the invention do not negatively interfere with corrosion inhibitor included in an aqueous solution. Without being limited to a particular theory of the invention, it is believed the reduction and/or elimination of the oxidant hydrogen peroxide from the peracid composition promotes the stability and efficacy of any variation in the amount of corrosion inhibitor present in a use solution.

Scale Inhibitors

Scale inhibitors are additional molecules used in oil and gas recovery operations. Common scale inhibitors that may be employed in these types of applications include polymers and co-polymers, phosphates, phosphate esters and the like.

In an aspect of the invention, a scale inhibitor is present in a use solution in an amount between about 100 ppm to 1,000 ppm. In a further aspect, a scale inhibitor is present in a use solution in an amount of at least about 0.0001 wt-% to about 10 wt-%, at least about 0.0001 wt-% to about 1 wt-%, preferably at least about 0.0001 wt-% to about 0.1 wt-%, preferably at least about 0.0001 wt-% to about 0.05 wt-%. Beneficially, the compositions and methods of the invention do not negatively interfere with scale inhibitor included in an aqueous solution. Without being limited to a particular theory of the invention, it is thought that the reduction and/or elimination of the oxidant hydrogen peroxide from the peracid composition promotes the stability and efficacy of any variation in the amount of scale inhibitor present in a use solution.

Additional Antimicrobial Agents

Additional antimicrobial agents may be included in the compositions and/or methods of the invention for enhanced antimicrobial efficacy. In addition to the use of peracid compositions, additional antimicrobial agents and biocides may be employed. Additional biocides may include, for example, a quaternary ammonium compound as disclosed in U.S. Pat. No. 6,627,657, which is incorporated herein by reference in its entirety. Beneficially, the presence of the quaternary ammonium compound provides both synergistic antimicrobial efficacies with peracids, as well as maintains long term biocidal efficacy of the compositions.

In another embodiment, the additional biocide may include an oxidizer compatible phosphonium biocide, such as tributyl tetradecyl phosphonium chloride. The phosphonium biocide provides similar antimicrobial advantages as the quaternary ammonium compound in combination with the peracids. In addition, the phosphonium biocide is compatible with the anionic polymeric chemicals commonly used in the oil field applications, such as the methods of the fracking disclosed according to the invention.

Additional antimicrobial and biocide agents may be employed in amounts sufficient to provide antimicrobial efficacy, as may vary depending upon the water source in need of treatment and the contaminants therein. Such agents may be present in a use solution in an amount of at least about 0.1 wt-% to about 50 wt-%, preferably at least about 0.1 wt-% to about 20 wt-%, more preferably from about 0.1 wt-% to about 10 wt-%.

Acidulants

Acidulants may be included as additional functional ingredients in a composition according to the invention. In an aspect, a strong mineral acid such as nitric acid or sulfuric acid can be used to treat water sources, as disclosed in U.S. Pat. No. 4,587,264, which is incorporated herein by reference in its entirety. The combined use of a strong mineral acid with the peracid composition provides enhanced antimicrobial efficacy as a result of the acidity assisting in removing chemical contaminants within the water source (e.g. sulfite and sulfide species). In addition, some strong mineral acids, such as nitric acid, provide a further benefit of reducing the risk of corrosion toward metals contacted by the peracid compositions according to the invention. Exemplary products are commercially available from Enviro Tech Chemical Services, Inc. (Reflex brand) and from Solvay Chemicals (Proxitane® NT brand).

Acidulants may be employed in amounts sufficient to provide the intended antimicrobial efficacy and/or anticorrosion benefits, as may vary depending upon the water source in need of treatment and the contaminants therein. Such agents may be present in a use solution in an amount of at least about 0.1 wt-% to about 50 wt-%, preferably at least about 0.1 wt-% to about 20 wt-%, more preferably from about 0.1 wt-% to about 10 wt-%.

Catalase and Peroxidase Enzyme

In an aspect of the invention, a catalase or peroxidase enzyme is used to reduce and/or eliminate the concentration of hydrogen peroxide in an antimicrobial peracid composition. The enzymes catalyze the decomposition of hydrogen peroxide to water and oxygen. Beneficially, the reduction and/or elimination of hydrogen peroxide (strong oxidizer) results in other additives for a water treatment source (e.g. water source) not being degraded or rendered incompatible. Various additives used to enhance or modify the characteristics of the aqueous fluids used in well drilling, recovery and production applications are at risk of degradation by the oxidizing effects of hydrogen peroxide. These may include for example, friction reducers and viscosity enhancers used in commercial well drilling, well completion and stimulation, or production applications.

Various sources of catalase enzymes may be employed according to the invention, including: animal sources such as bovine catalase isolated from beef livers; fungal catalases isolated from fungi including *Penicillium chrysogenum*, *Penicillium notatum*, and *Aspergillus niger*; plant sources; bacterial sources such as *Staphylcoccus aureus*, and genetic variations and modifications thereof. In an aspect of the invention, fungal catalases are utilized to reduce the hydrogen peroxide content of a peracid composition. Catalases are commercially available in various forms, including liquid and spray dried forms. Commercially available catalase includes both the active enzyme as well as additional ingredients to enhance the stability of the enzyme. Some exemplary commercially available catalase enzymes include Genencor CA-100 and CA-400, as well as Mitsubishi Gas and Chemical (MGC) ASC super G and ASC super 200, and Optimase CA 400L from Genecor International. Additional description of suitable catalase enzymes are disclosed and herein incorporated by reference in its entirety from U.S. Patent Publication No. 2009/0269324.

In an aspect of the invention, catalase enzymes have a high ability to decompose hydrogen peroxide. Beneficially, the reduction or elimination of hydrogen peroxide from oxidizing compositions obviates the various detriments caused by oxidizing agents. In particular, the use of catalase with the peracids compositions provides enhanced antimicrobial benefits without causing the damage associated with conventional oxidizing agents (e.g. peracetic acid, hypochlorite or hypochlorous acid, and/or chlorine dioxide), such as corrosion.

Peroxidase enzymes may also be employed to decompose hydrogen peroxide from a peracid composition. Although peroxidase enzymes primarily function to enable oxidation of substrates by hydrogen peroxide, they are also suitable for effectively lowering hydrogen peroxide to peracid ratios in compositions. Various sources of peroxidase enzymes may be employed according to the invention, including for example animal sources, fungal peroxidases, and genetic variations and modifications thereof. Peroxidases are commercially available in various forms, including liquid and spray dried forms. Commercially available peroxidases include both the active enzyme as well as additional ingredients to enhance the stability of the enzyme.

In some embodiments, the catalase or peroxidase enzyme is able to degrade at least about 50% of the initial concentration of hydrogen peroxide in a peracid composition. Preferably, the enzyme is provided in sufficient amount to reduce the hydrogen peroxide concentration of a peracid composition by at least more than about 50%, more preferably at least about 60%, at least about 70%, at least about 80%, at least about 90%. In some embodiments, the enzyme reduces the hydrogen peroxide concentration of a peracid composition by more than 90%.

In an aspect of the invention, the enzymes are suitable for use and have a tolerance to a wide range of temperatures, including the temperatures ranges in water treatment applications which may range from about 0-180° C. A suitable catalase enzyme will maintain at least 50% of its activity under such storage and/or application temperatures for at least about 10 minutes, preferably for at least about 1 hour.

In a further aspect of the invention, the catalase or peroxidase enzymes described herein have a tolerance to pH ranges found in water treatment applications. Acetic acid levels (or other carboxylic acid) in a water treatment application can widely range in parts per million (ppm) of acetic or other carboxylic acid. The solutions may have a corresponding range of pH range from greater than 0 to about 10. A suitable catalase or peroxidase enzyme will maintain at least about 50% of its activity in such solutions of acetic or other carboxylic acid over a period of about 10 minutes.

In an aspect of the invention, a catalase or peroxidase enzyme is present in a use solution of the water treatment and peracid composition in sufficient amounts to reduce the concentration of hydrogen peroxide from the peracid composition by at least 50% within about 10 minutes, preferably within about 5 minutes, preferably within about 2 to 5 minutes, more preferably within about 1 minute. The ranges of concentration of the enzymes will vary depending upon the amount of time within which 50% of the hydrogen peroxide from the peracid composition is removed. In certain aspects of the invention, a catalase or peroxidase enzyme is present in a use solution composition including the water source to be treated in amounts between about 1 ppm and about 1,000 ppm, preferably between about 5 ppm and 500 ppm, and more preferably between about 10 ppm and about 100 ppm.

Uses of the Present Compositions

In another aspect, the present invention is directed to a method for storing a percarboxylic acid containing composition, which method comprises storing the above compositions, wherein said composition retains at least about 80% of the $C_1$-$C_{22}$ percarboxylic acid activity after storage for any suitable time under any suitable conditions, e.g., retaining at least about 80% of the $C_1$-$C_{22}$ percarboxylic acid activity after storage of about 30 days at about 50° C. Preferably, the present compositions retain at least about 85%, 90% or higher of the $C_1$-$C_{22}$ percarboxylic acid activity after storage of about 30 days at about 50° C.

In still another aspect, the present invention is directed to a method for transporting a percarboxylic acid containing composition, which method comprises transporting the above compositions under ambient conditions, preferably in bulk e.g., 1,000 gallons and above, wherein the SADT of said composition is at least 45° C. during transportation. Preferably, the SADT of said composition is higher than at least 50° C., 55° C., 60° C. 65° C. or 70° C.

In yet another aspect, the present invention is directed to a method for treating water, which method comprises providing the above compositions to a water source in need of treatment to form a treated water source, wherein said treated water source comprises from about 1 ppm to about 1,000 ppm of said $C_1$-$C_{22}$ percarboxylic acid.

The present methods can be used to treat any suitable or desirable water sources. For example, the present methods can be used to treat fresh water, pond water, sea water, produced water and a combination thereof. In some embodiments, the water source comprises at least about 1 wt-% produced water. In other embodiments, the water source comprises at least about 1 wt-%, 2 wt-%, 3 wt-%, 4 wt-%, 5 wt-%, 6 wt-%, 7 wt-%, 8 wt-%, 9 wt-%, or 10 wt-%, 15 wt-%, 20 wt-%, 25 wt-%, 30 wt-% or more produced water.

The treated water source can comprise any suitable concentration of the $C_1$-$C_{22}$ percarboxylic acid. In some embodiments, the treated water source comprises from about 10 ppm to about 200 ppm of the $C_1$-$C_{22}$ percarboxylic acid. In other embodiments, the treated water source comprises about 1 ppm, 10 ppm, 100 ppm, 200 ppm, 300 ppm, 400 ppm, 500 ppm, 600 ppm, 700 ppm, 800 ppm, 900 ppm or 1,000 ppm of the $C_1$-$C_{22}$ percarboxylic acid.

The present methods can be used to treat any suitable or desirable water sources. In another example, the present methods can be used to treat fresh water, pond water, sea water, produced water and a combination thereof. In some embodiments, the water source comprises at least about 1 wt-% produced water. In other embodiments, the water source comprises at least about 1 wt-%, 2 wt-%, 3 wt-%, 4 wt-%, 5 wt-%, 6 wt-%, 7 wt-%, 8 wt-%, 9 wt-%, or 10 wt-%, 15 wt-%, 20 wt-%, 25 wt-%, 30 wt-% or more produced water.

Any suitable $C_1$-$C_{22}$ percarboxylic acid can be used in the present methods. For example, peroxyacetic acid, peroxyoctanoic acid and/or peroxysulfonated oleic acid can be used. In some embodiments, a combination of peroxyacetic acid, peroxyoctanoic acid and peroxysulfonated oleic acid is used.

The treated water source can comprise any suitable concentration of the hydrogen peroxide. In some embodiments, the treated water source comprises from about 1 ppm to about 15 ppm of the hydrogen peroxide. In other embodiments, the treated water source comprises about 1 ppm, 2 ppm, 3 ppm, 4 ppm, 5 ppm, 6 ppm, 7 ppm, 8 ppm, 9 ppm, 10 ppm, 11 ppm, 12 ppm, 13 ppm, 14 ppm, or 15 ppm of the hydrogen peroxide.

The treated water source can retain any suitable concentration and/or percentage of the initial $C_1$-$C_{22}$ percarboxylic acid activity in the treated water source for any suitable time period after the treated water source is formed. In some embodiments, the treated water source retains at least about 60%, 65%, 70%, 75%, 80%, 85% or 90% of the initial $C_1$-$C_{22}$ percarboxylic acid activity in the treated water source for a suitable time after the treated water source is formed. In other embodiments, the treated water source retains at least about 60%, 65%, 70%, 75%, 80%, 85% or 90% of the initial $C_1$-$C_{22}$ percarboxylic acid activity in the treated water source for at least 15 minutes after the treated water source is formed.

In some embodiments, the level of a microorganism, if present in the water source, is stabilized or reduced by the present methods. For example, at least 10%, 20%, 30%, 40%, 50%, 60%, 70%, 80%, or 90% or more of the microorganism, if present in the water source, is killed, destroyed, removed and/or inactivated by the present methods.

In some embodiments, the antimicrobial efficacy of the composition used in the present methods on the treated water source is comparable to antimicrobial effect of a water source that does not contain produced water. In other embodiments, the treated water source reduces corrosion caused by hydrogen peroxide and reduces microbial-induced corrosion, and the composition used in the present methods does not substantially interfere with a friction reducer, a viscosity enhancer, other functional ingredients present in the treated water source, or a combination thereof.

In some embodiments, the present methods can comprise adding a peroxidase or a catalase to further reduce the hydrogen peroxide level in the treated water source. The peroxidase or catalase can be added in any suitable manner. In some embodiments, the peroxidase or catalase can be added to the water source before a composition used in the present methods is provided to the water source. In other embodiments, the present compositions can be diluted into a suitable intermediate volume, and the peroxidase or catalase can be added to the diluted, intermediate volume. Thereafter, the diluted, intermediate volume, which contains the peroxidase or catalase, can be added to the water source. Any suitable peroxidase or catalase, including the ones described below, can be used in the present methods.

In some embodiments, the present methods can further comprise directing the treated water source into a subterranean environment or disposing of the treated water source.

In some embodiments, the water source treated by the present methods does not comprise reuse water, the treated water source comprises from about 10 ppm to about 20 ppm of the $C_1$-$C_{22}$ percarboxylic acid and from about 1 ppm to about 2 ppm of hydrogen peroxide and the treated water source does not comprise a friction reducer and/or a rheology modifier.

In some embodiments, the water source treated by the present methods is a blended water source that comprises about 80 wt-% fresh water or pond water and about 20 wt-% of reuse water, the treated water source comprises from about 25 ppm to about 35 ppm of the $C_1$-$C_{22}$ percarboxylic acid and from about 2 ppm to about 3 ppm of hydrogen peroxide and catalase, the treated water source does not comprise a friction reducer and/or a rheology modifier, and the treated water source is formed before reaching a blending tub.

In some embodiments, the water source treated by the present methods is a blended water source that comprises about 80 wt-% fresh water or pond water and about 20 wt-% of reuse water, the treated water source comprises from about 25 ppm to about 35 ppm of the $C_1$-$C_{22}$ percarboxylic acid and from about 2 ppm to about 3 ppm of hydrogen peroxide and catalase, the treated water source comprises a friction reducer and/or a rheology modifier, and the treated water source is formed in a blending tub.

In some embodiments, the treated water source comprises from about 30 ppm or less of the $C_1$-$C_{22}$ percarboxylic acid and about 0.5 ppm or less of the hydrogen peroxide, the treated water source comprises a friction reducer and/or a rheology modifier, and the treated water source is directed into or is at a subterranean environment.

In some aspects, the methods disclosed for water treatment in oil and gas recovery provide effective antimicrobial efficacy without deleterious interaction with functional agents, including for example friction reducers. In a further aspect, the methods for water treatment provide increased antimicrobial efficacy compared to the use of the antimicrobial peracids alone. In a still further aspect, the methods of use result in the disposal of cleaner water with low numbers of microorganisms. In yet a further aspect of the methods of the invention, the reduction and/or elimination of $H_2O_2$ from the peracid compositions minimizes the negative effects of the oxidant $H_2O_2$. Still further, the methods of the invention reduce the volume expansion within sealed systems used in oil and gas recovery methods, as a result of the reduction and/or elimination of $H_2O_2$ from the systems.

Use in Water Treatment

The treated peracid compositions can be used for a variety of industrial applications, e.g., to reduce microbial or viral populations on a surface or object or in a body or stream of water. In some aspects, the invention includes methods of using the treated peracid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, peracid and catalase compositions (or other treated peracid compositions having low to substantially no hydrogen peroxide) are used to control the growth of microorganisms in water used in various oil and gas operations. In a further aspect, the compositions are suitable for incorporating into fracturing fluids to control or eliminate microorganisms.

As used herein for the methods of the invention, treated peracid compositions can employ a variety of peracid compositions having a low to substantially no hydrogen peroxide concentration. These treated peracid compositions include peracid compositions with a catalase or peroxidase enzyme to reduce the hydrogen peroxide to peracid ratio and/or other reduced hydrogen peroxide peracid compositions disclosed herein. In a preferred embodiment peracid and catalase use solutions having reduced or substantially no hydrogen peroxide are introduced to a water source in need of treatment.

The methods by which the treated peracid use solutions are introduced into the aqueous fluids according to the invention are not critical. Introduction of the treated peracid compositions may be carried out in a continuous or intermittent manner and will depend on the type of water being treated. In some embodiments, the treated peracid compositions are introduced into an aqueous fluid according to the methods disclosed in U.S. patent application Ser. No. 13/645,671, titled "New Method and Arrangement for Feeding Chemicals into a Hydrofracturing Process and Oil and Gas Applications", which is hereby incorporated by reference in its entirety.

In an aspect, the treated peracid use solutions are added to waters in need of treatment prior to the drilling and fracking steps in order to restrict the introduction of microbes into the reservoir and to prevent the microbes from having a negative effect on the integrity of the fluids. The treatment of source waters (e.g. pond, lake, municipal, etc.) and/or produced waters is particularly well suited for use according to the invention.

The treated waters according to the invention can be used for both slick water fracturing (i.e. using frictions reducers) and/or gel fracturing (i.e. using viscosity enhancers), depending on the type of formation being fractured and the type of hydrocarbon expected to be produced. Use of a treated peracid use solution, including a catalase treated peracid composition use solution having low to substantially no hydrogen peroxide, is suitable for both slick water fracturing and gel fracturing.

In an aspect, pretreating the peracid peracetic acid (including a mixture of acetic acid, hydrogen peroxide and water) with catalase substantially removes the hydrogen peroxide with minimal to no impact on the fracturing fluids and the well itself. In an aspect, the peracetic acid pretreated with catalase allows the formation of gel suitable for gel fracturing, as opposed to untreated peracetic acid/hydrogen peroxide solutions that do not allow a gel to form under certain conditions. In a further aspect, the treated peracid use solutions are added to waters in need of treatment in the subterranean well formations (e.g. introduced through a bore hole in a subterranean formation). These methods provide additional control within the well formation suitable for reducing microbial populations already present within the down hole tubing in the well or within the reservoir itself.

In a still further aspect, the treated peracid use solutions are added to waters in need of treatment before disposal. In such an aspect, flow back waters (e.g. post fracking) are treated to minimize microbial contaminations in the waters and to remove solids prior to disposal of the water into a subterranean well, reuse in a subsequent fracturing application or return of the water into local environmental water sources.

In an aspect, the water source in need of treatment may vary significantly. For example, the water source may be a freshwater source (e.g. pond water), salt water or brine source, brackish water source, recycled water source, or the like. In an aspect, wherein offshore well drilling operations are involved, seawater sources are often employed (e.g. saltwater or non-saltwater). Beneficially, the peracid compositions, with or without catalase, of the invention are suitable for use with any types of water and provide effective antimicrobial efficiency with any of such water sources.

Large volumes of water are employed according to the invention as required in well fluid operations. As a result, in an aspect of the invention, recycled water sources (e.g. produced waters) are often employed to reduce the amount of a freshwater, pond water or seawater source required. Recycled or produced water are understood to include non-potable water sources. The use of such produced waters (in combination with freshwater, pond water or seawater) reduces certain economic and/or environmental constraints. In an aspect of the invention, thousands to millions of gallons of water may be employed and the combination of produced water with fresh water sources provides significant economic and environmental advantages. In an aspect of the invention, as much produced water as practical is employed. In an embodiment at least 1% produced water is employed, preferably at least 5% produced water is employed, preferably at least 10% produced water is employed, preferably at least 20% produced water is employed, or more preferably more than 20% produced water is employed.

In an aspect of the invention, the method includes a pretreatment step, wherein the peracid composition is treated with a catalase enzyme to reduce the hydrogen peroxide concentration in a use solution. The pretreatment step occurs prior to combining the peracid antimicrobial composition and/or catalase to a water source in need of treatment. In an aspect of the invention, the pretreatment may occur within a few minutes to hours before addition to a water source. Preferably, a commercial peracid formulation is employed (e.g. peracetic acid). Thereafter, the peracid and catalase composition use solution may be diluted to obtain the desired peracetic acid concentrations, with low and/or no hydrogen peroxide concentration.

According to embodiments of the invention, a sufficient amount of the pretreated peracid use solution composition, with or without catalase, is added to the aqueous water source in need of treatment to provide the desired peracid concentration for antimicrobial efficacy. For example, a water source is dosed amounts of the peracid and catalase use solution composition until a peracid concentration within the water source is detected within the preferred concentration range (e.g. about 1 ppm to about 100 ppm peracid). In an aspect, it is preferred to have a microbial count of less than about 100,000 microbes/mL, more preferably less than about 10,000 microbes/mL, or more preferably less than about 1,000 microbes/mL.

The methods of use as described herein can vary in the temperature and pH conditions associated with use of the aqueous treatment fluids. For example, the aqueous treatment fluids may be subjected to varying ambient temperatures according to the applications of use disclosed herein, including ranging from about 0° C. to about 130° C. in the course of the treatment operations. Preferably, the temperature range is between about 5° C. to about 100° C., more preferably between about 10° C. to about 80° C. However, as a majority of the antimicrobial activity of the compositions of the invention occurs over a short period of time, the exposure of the compositions to relatively high temperatures is not a substantial concern. In addition, the peracid composition aqueous treatment fluids (i.e. use solutions) may be subjected to varying pH ranges, such as from 1 to about 10.5. Preferably, the pH range is less than about 9, less than about 8.2 (pKa value of the representative peracid peracetic acid) to ensure the effective antimicrobial efficacy of the peracid.

The antimicrobial compositions of the invention are fast-acting. However, the present methods require a certain minimal contact time of the compositions with the water in need of treatment for occurrence of sufficient antimicrobial effect. The contact time can vary with concentration of the use compositions, method of applying the use compositions, temperature of the use compositions, pH of the use compositions, amount of water to be treated, amount of soil or substrates in the water to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. The contact time will further vary based upon the concentration of peracid in a use solution.

Beneficial Effects of the Methods of Use in Water Treatment

In an aspect, the methods of use provide an antimicrobial for use that does not negatively impact the environment. Beneficially, the degradation of the compositions of the invention provides a "green" alternative. In an aspect of the invention, utilizing peroxyacetic acid is beneficial as the by-products are non-toxic, non-persistent in the environment, certified as organic and permitted for discharge in surface waters.

In a further aspect, the methods of use provide an antimicrobial for use that does not negatively interfere with friction reducers, viscosity enhancers and/or other functional ingredients. In a further aspect, the methods of use do not negatively interfere with any additional functional agents utilized in the water treatment methods, including for example, corrosion inhibitors, descaling agents and the like. The compositions administered according to the invention provide extremely effective control of microorganisms without adversely affecting the functional properties of any additive polymers of an aqueous system. In addition, the treated peracid composition use solutions provide additional benefits to a system, including for example, reducing corrosion within the system due to the decreased or substantially eliminated hydrogen peroxide from a treated peracid composition. Beneficially, the non-deleterious effects of the treated peracid compositions (with or without a catalase) on the various functional ingredients used in water treatment methods are achieved regardless of the make-up of the water source in need of treatment.

In an additional aspect, the methods of use prevent the contamination of systems, such as well or reservoir souring. In further aspects, the methods of use prevent microbiologically-influenced corrosion of the systems upon which it is employed.

In additional aspects of the invention, the reduction and/or elimination of $H_2O_2$ from the systems reduces volume expansion within sealed systems (e.g. wells). As a result there is a significantly decreased or eliminated risk of well blow outs due to the removal of gases within the antimicrobial compositions used for treating the various water sources.

In further aspects, the methods of use employ the antimicrobial and/or bleaching activity of the peracid compositions. For example, the invention includes a method for reducing a microbial population and/or a method for bleaching. These methods can operate on an article, surface, in a body or stream of water or a gas, or the like, by contacting the article, surface, body, or stream with the compositions. Contacting can include any of numerous methods for applying the compositions, including, but not limited to, providing the antimicrobial peracid compositions in an aqueous use solution and immersing any articles, and/or providing to a water source in need of treatment.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms associated with oil- and gas-field operations.

Exemplary microorganisms susceptible to the peracid compositions of the invention include, gram positive bacteria (e.g., *Staphylococcus aureus, Bacillus* species (sp.) like *Bacillus subtilis, Clostridia* sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger, Cephalosporium acremonium, Penicillium*

*notatum*, and *Aureobasidium pullulans*), filamentous fungi (e.g., *Aspergillus niger* and *Cladosporium resinae*), algae (e.g., *Chlorella vulgaris, Euglena gracilis,* and *Selenastrum capricornutum*), and other analogous microorganisms and unicellular organisms (e.g., phytoplankton and protozoa). Other exemplary microorganisms susceptible to the peracid compositions of the invention include the exemplary microorganisms disclosed in U.S. patent application US 2010/0160449 A1, e.g., the sulfur- or sulfate-reducing bacteria, such as *Desulfovibrio* and *Desulfotomaculum* species.

Use in Other Treatments

Additional embodiments of the invention include water treatments for various industrial processes for treating liquid systems. As used herein, "liquid system" refers to flood waters or an environment within at least one artificial artifact, containing a substantial amount of liquid that is capable of undergoing biological fouling. Liquid systems include but are not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In a further aspect, the compositions can also be used to treat other liquid systems where both the compositions' antimicrobial function and oxidant properties can be utilized. Aside from the microbial issues surrounding waste water, waste water is often rich in malodorous compounds of reduced sulfur, nitrogen or phosphorous. A strong oxidant such as the compositions disclosed herein converts these compounds efficiently to their odor free derivatives e.g. the sulfates, phosphates and amine oxides. These same properties are very useful in the pulp and paper industry where the property of bleaching is also of great utility.

C. SLICK WATER COMPOSITIONS AND USES THEREOF

The present invention also relates to slick water compositions useful in oil and/or gas drilling that comprise stable percarboxylic acid compositions and uses thereof. In one aspect, the present invention is directed to a composition, which composition comprises:

1) a $C_1$-$C_{22}$ carboxylic acid;
2) a $C_1$-$C_{22}$ percarboxylic acid;
3) hydrogen peroxide;
4) a first stabilizing agent, which is a picolinic acid or a compound having the following Formula (IA):

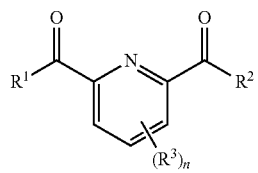

(IA)

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
or a compound having the following Formula (IB):

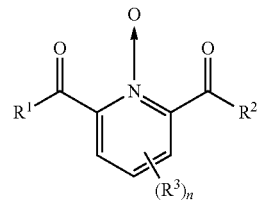

(IB)

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
5) a second stabilizing agent, which is a compound having the following
Formula (IIA):

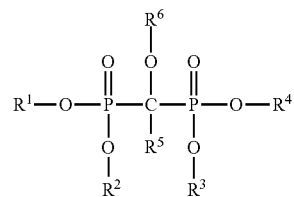

(IIA)

wherein
$R^1$, $R^2$, $R^3$, and $R^4$ are independently hydrogen, ($C_1$-$C_6$) alkyl, ($C_2$-$C_6$)alkenyl or ($C_2$-$C_6$)alkynyl, or $C_{6-20}$ aryl;
$R^5$ is ($C_1$-$C_6$)alkyl, ($C_2$-$C_6$)alkenyl or ($C_2$-$C_6$)alkynyl; and
$R^6$ is hydrogen, ($C_1$-$C_6$)alkyl, ($C_2$-$C_6$)alkenyl or ($C_2$-$C_6$) alkynyl;
or a salt thereof;
or a compound having the following Formula (IIB):

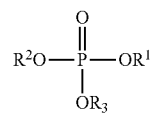

(IIB)

wherein
$R^1$, $R^2$, and $R^3$ are independently hydrogen, ($C_1$-$C_6$)alkyl, ($C_2$-$C_6$)alkenyl or ($C_2$-$C_6$)alkynyl, or $C_{6-20}$ aryl;
or a salt thereof;
6) a friction reducer; and
wherein said hydrogen peroxide has a concentration of about 1 ppm to about 20 ppm, and the $C_1$-$C_{22}$ percarboxylic acid has a concentration of at least about 2 times of the concentration of said hydrogen peroxide.

In some embodiments, the present composition is an equilibrated composition that comprises peracid, hydrogen peroxide, carboxylic acid and a solvent, e.g., water. In some embodiments, the present composition does not comprise a mineral acid, e.g., the mineral acids disclosed in WO 91/07375.

The present composition can comprise any suitable level of the hydrogen peroxide. In some embodiments, the hydrogen peroxide in the present compositions has a concentration of about 1 ppm to about 10 ppm, e.g., 1 ppm, 2 ppm, 3 ppm, 4 ppm, 5 ppm, 6 ppm, 7 ppm, 8 ppm, 9 ppm, or 10 ppm.

The present composition can comprise any suitable level of the $C_1$-$C_{22}$ percarboxylic acid relative to the level of the hydrogen peroxide. In some embodiments, the $C_1$-$C_{22}$ percarboxylic acid has a concentration of at least about 6 times of the concentration of the hydrogen peroxide. In other embodiments, the $C_1$-$C_{22}$ percarboxylic acid has a concentration of at least about 10 times of the concentration of the hydrogen peroxide. In still other embodiments, the $C_1$-$C_{22}$ percarboxylic acid has a concentration of at least about 2, 3, 4, 5, 6, 7, 8, 9 or 10 times of the concentration of the hydrogen peroxide.

The present composition can comprise any suitable friction reducer. In some embodiments, the friction reducer is a polyacrylamide polymer and/or copolymer, or an acrylamide-derived polymer and/or copolymer. Other exemplary friction reducers include the ones described in the above Section B. The present composition can comprise any suitable level of the friction reducer. In some embodiments, the friction reducer has a concentration from about 50 ppm to about 5,000 ppm, preferably from about 100 ppm to about 1,000 ppm. In other embodiments, the friction reducer has a concentration at about 50 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm.

The present composition can further comprise any substances suitable for oil and/or gas drilling. In some embodiments, the present composition can further comprise a proppant, a surfactant and/or a scale inhibitor. Any suitable proppant can be used. In some embodiments, the proppant is a sand or a ceramic bead. Any suitable scale inhibitor can be used. In some embodiments, the scale inhibitor is a polymer, a phosphonate or a phosphate ester.

Any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic acid comprises peroxyacetic acid, peroxyoctanoic acid and/or peroxysulfonated oleic acid. Other exemplary $C_1$-$C_{22}$ percarboxylic acids are described in the above Section B. The present composition can comprise any suitable level of the $C_1$-$C_{22}$ percarboxylic acid and hydrogen peroxide. In some embodiments, the $C_1$-$C_{22}$ percarboxylic acid has a concentration from about 10 ppm to about 30 ppm, e.g., 10 ppm, 15 ppm, 20 ppm, 25 ppm, or 30 ppm, and the hydrogen peroxide has a concentration from about 1 ppm to about 3 ppm, e.g., 1 ppm, 1.5 ppm, 2 ppm, 2.5 ppm, or 3 ppm.

Any suitable first stabilizing agent can be used in the present compositions. In some embodiments, the first stabilizing agent is a picolinic acid, or a salt thereof. In other embodiments, the first stabilizing agent is 2,6-pyridinedicarboxylic acid, or a salt thereof. The first stabilizing agent can be used at any suitable concentration. In some embodiments, the first stabilizing agent has a concentration from about 0.005 wt-% to about 5 wt-%. In other embodiments, the first stabilizing agent has a concentration from about 0.05 wt-% to about 0.15 wt-%. In still other embodiments, the first stabilizing agent has a concentration at about 0.005 wt-%, 0.01 wt-%, 0.1 wt-%, 1 wt-%, 2 wt-%, 3 wt-%, 4 wt-%, or 5 wt-%. In yet other embodiments, the first stabilizing agent has a concentration at about 0.05 wt-%, 0.06 wt-%, 0.07 wt-%, 0.08 wt-%, 0.09 wt-%, 0.10 wt-%, 0.11 wt-%, 0.12 wt-%, 0.13 wt-%, 0.14 wt-%, or 0.15 wt-%.

Any suitable second stabilizing agent can be used in the present compositions. In some embodiments, the second stabilizing agent is 1-hydroxy ethylidene-1,1-diphosphonic acid (HEDP), or a salt thereof. The second stabilizing agent can be used at any suitable concentration. In some embodiments, the second stabilizing agent has a concentration from about 0.1 wt-% to about 10 wt-%, e.g., 0.1 wt-%, 0.5 wt-%, 1 wt-%, 2 wt-%, 3 wt-%, 4 wt-%, 5 wt-%, 6 wt-%, 7 wt-%, 8 wt-%, 9 wt-%, or 10 wt-%. In other embodiments, the second stabilizing agent has a concentration from about 0.5 wt-% to about 5 wt-%, e.g., 0.5 wt-%, 1 wt-%, 1.5 wt-%, 2 wt-%, 2.5 wt-%, 3 wt-%, 3.5 wt-%, 4 wt-%, 4.5 wt-% or 5 wt-%. In still other embodiments, the second stabilizing agent has a concentration from about 0.6 wt-% to about 1.8 wt-%, e.g., 0.6 wt-%, 0.7 wt-%, 0.8 wt-%, 0.9 wt-%, 1.0 wt-%, 1.1 wt-%, 1.2 wt-%, 1.3 wt-%, 1.4 wt-%, 1.5 wt-%, 1.6 wt-%, 1.7 wt-%, or 1.8 wt-%.

In some embodiments, the first stabilizing agent is a 2,6-pyridinedicarboxylic acid, or a salt thereof, and the second stabilizing agent is HEDP, or a salt thereof.

The present compositions can retain any suitable level or percentage of the $C_1$-$C_{22}$ percarboxylic acid activity for any suitable time after the composition is formed. In some embodiments, the present composition retains at least about 60%, 65%, 70%, 75%, 80%, 85% or 90% of the initial $C_1$-$C_{22}$ percarboxylic acid activity for any suitable time after the composition is formed. In other embodiments, the present composition retains at least about 60% of the initial $C_1$-$C_{22}$ percarboxylic acid activity for at least 1, 2, 3, 4, 5, 6, 7, 8, 9, 10, 11, 12, 13, 14, 15, 20, 25, 30 minutes, 1, 2, 5, 10, 15, 20 or 24 hours, or longer after the composition is formed.

In some embodiments, the present compositions can comprise a peroxidase or a catalase to further reduce the hydrogen peroxide concentration. Any suitable peroxidase or a catalase can be used in the present compositions. Exemplary peroxidases and catalases are described in the above Section B. In other embodiments, the present compositions can further comprise a substance that aids solubilization of the first and/or second stabilizing agent(s). Exemplary substances that can aid solubilization of the first and/or second stabilizing agent(s) include hydrotropes such as sodium xylene sulfonate, sodium cumene sulfonates, and surfactants, such as anionic surfactants and noinionic surfactants.

In another aspect, the present invention is directed to a method for slick water fracturing, which method comprises directing the above composition into a subterranean environment.

The present compositions can be directed into a subterranean environment at any suitable speed. In some embodiments, the present composition is directed into a subterranean environment at a speed faster than 30 barrel (bbl)/min. In other embodiments, the present composition is directed into a subterranean environment at a speed from about 50 bbl/min to about 100 bbl/min., e.g., 50, 60, 70, 80, 90 or 100 bbl/min The present compositions can be directed into any suitable subterranean environment. In some embodiments, the subterranean environment comprises a well in a shale gas and/or oil reservoir.

The present compositions can be directed into a subterranean environment by any suitable methods. In some embodiments, the composition is pumped down a well-bore.

D. GEL BASED COMPOSITIONS AND USES THEREOF

The present invention further relates to gel based compositions useful in oil and/or gas drilling that comprise stable percarboxylic acid compositions and uses thereof. In one aspect, the present invention is directed to a composition, which composition comprises:

1) a $C_1$-$C_{22}$ carboxylic acid;
2) a $C_1$-$C_{22}$ percarboxylic acid;
3) hydrogen peroxide;
4) a first stabilizing agent, which is a picolinic acid or a compound having the following Formula (IA):

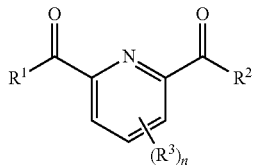

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
or a compound having the following Formula (IB):

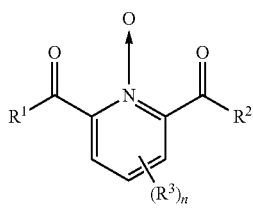

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
5) a second stabilizing agent, which is a compound having the following Formula (IIA):

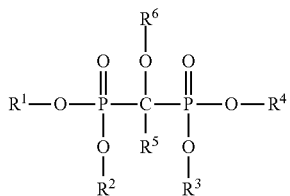

wherein
$R^1$, $R^2$, $R^3$, and $R^4$ are independently hydrogen, ($C_1$-$C_6$) alkyl, ($C_2$-$C_6$)alkenyl or ($C_2$-$C_6$)alkynyl, or $C_{6-20}$ aryl;
$R^5$ is ($C_1$-$C_6$)alkyl, ($C_2$-$C_6$)alkenyl or ($C_2$-$C_6$)alkynyl; and $R^6$ is hydrogen, ($C_1$-$C_6$)alkyl, ($C_2$-$C_6$)alkenyl or ($C_2$-$C_6$) alkynyl;
or a salt thereof;
or a compound having the following Formula (IIB):

wherein
$R^1$, $R^2$, and $R^3$ are independently hydrogen, ($C_1$-$C_6$)alkyl, ($C_2$-$C_6$)alkenyl or ($C_2$-$C_6$)alkynyl, or $C_{6-20}$ aryl;
or a salt thereof;
6) a viscosity enhancer; and
wherein said hydrogen peroxide has a concentration of about 1 ppm to about 15 ppm, and said $C_1$-$C_{22}$ percarboxylic acid has a concentration of at least about 2 times of the concentration of said hydrogen peroxide.

In some embodiments, the present composition is an equilibrated composition that comprises peracid, hydrogen peroxide, carboxylic acid and a solvent, e.g., water. In some embodiments, the present composition does not comprise a mineral acid, e.g., the mineral acids disclosed in WO 91/07375.

The present composition can comprise any suitable level of the hydrogen peroxide. In some embodiments, the hydrogen peroxide in the present compositions has a concentration of about 1 ppm to about 15 ppm, e.g., 1 ppm, 2 ppm, 3 ppm, 4 ppm, 5 ppm, 6 ppm, 7 ppm, 8 ppm, 9 ppm, 10 ppm, 11 ppm, 12 ppm, 13 ppm, 14 ppm, or 15 ppm.

The present composition can comprise any suitable level of the $C_1$-$C_{22}$ percarboxylic acid relative to the level of the hydrogen peroxide. In some embodiments, the $C_1$-$C_{22}$ percarboxylic acid has a concentration of at least about 6 times of the concentration of the hydrogen peroxide. In other embodiments, the $C_1$-$C_{22}$ percarboxylic acid has a concentration of at least about 10 times of the concentration of the hydrogen peroxide. In still other embodiments, the $C_1$-$C_{22}$ percarboxylic acid has a concentration of at least about 2, 3, 4, 5, 6, 7, 8, 9 or 10 times of the concentration of the hydrogen peroxide.

Any suitable viscosity enhancer can be used in the present compositions. In some embodiments, the viscosity enhancer is a conventional linear gel, a borate-crosslinked gel, an organometallic-crosslinked gel or an aluminium phosphate-ester oil gel. Other exemplary viscosity enhancers include the ones described in the above Section B. The viscosity enhancer can be used at any suitable levels. In some embodiments, the viscosity enhancer has a concentration from about 2 to about 100 units of pounds per thousand gallons, preferably from about 5 to about 65 units of pounds per thousand gallons. In other embodiments, the viscosity enhancer has a concentration at about 2, 3, 4, 5, 6, 7, 8, 9, 10, 20, 30, 40, 50, 60, 70, 80, 90 or 100 units of pounds per thousand gallons.

The present composition can further comprise any substances suitable for oil and/or gas drilling. In some embodiments, the present composition can further comprise a proppant, a surfactant, a scale inhibitor and/or a breaker. Any suitable proppant can be used. In some embodiments, the proppant is a sand or a ceramic bead. Any suitable scale inhibitor can be used. In some embodiments, the scale inhibitor is a polymer, a phosphonate or a phosphate ester. Any suitable breaker can be used. In some embodiments, the breaker is an oxidizer, an enzyme or a pH modifier.

Any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic acid comprises peroxyacetic acid, peroxyoctanoic acid and/or peroxysulfonated oleic acid. Other exemplary $C_1$-$C_{22}$ percarboxylic acids are described in the above Section B.

The present composition can comprise any suitable level of the $C_1$-$C_{22}$ percarboxylic acid and hydrogen peroxide. In some embodiments, the $C_1$-$C_{22}$ percarboxylic acid has a concentration that is effective for its anti-microbial function and the hydrogen peroxide has a concentration that will not cause gel failure. In other embodiments, the hydrogen peroxide has a concentration that is about 14 ppm or less. In still other embodiments, the $C_1$-$C_{22}$ percarboxylic acid has a concentration from about 10 ppm to about 30 ppm, e.g., 10 ppm, 15 ppm, 20 ppm, 25 ppm, or 30 ppm, and the hydrogen peroxide has a concentration from about 1 ppm to about 3 ppm, e.g., 1 ppm, 1.5 ppm, 2 ppm, 2.5 ppm, or 3 ppm.

Any suitable first stabilizing agent can be used in the present compositions. In some embodiments, the first stabilizing agent is a picolinic acid, or a salt thereof. In other embodiments, the first stabilizing agent is 2,6-pyridinedicarboxylic acid, or a salt thereof. The first stabilizing agent can be used at any suitable concentration. In some embodiments, the first stabilizing agent has a concentration from about 0.005 wt-% to about 5 wt-%. In other embodiments, the first stabilizing agent has a concentration from about 0.05 wt-% to about 0.15 wt-%. In still other embodiments, the first stabilizing agent has a concentration at about 0.005 wt-%, 0.01 wt-%, 0.1 wt-%, 1 wt-%, 2 wt-%, 3 wt-%, 4 wt-%, or 5 wt-%. In yet other embodiments, the first stabilizing agent has a concentration at about 0.05 wt-%, 0.06 wt-%, 0.07 wt-%, 0.08 wt-%, 0.09 wt-%, 0.10 wt-%, 0.11 wt-%, 0.12 wt-%, 0.13 wt-%, 0.14 wt-%, 0.15 wt-%.

Any suitable second stabilizing agent can be used in the present compositions. In some embodiments, the second stabilizing agent is 1-hydroxy ethylidene-1,1-diphosphonic acid (HEDP), or a salt thereof. The second stabilizing agent can be used at any suitable concentration. In some embodiments, the second stabilizing agent has a concentration from about 0.1 wt-% to about 10 wt-%, e.g., 0.1 wt-%, 0.5 wt-%, 1 wt-%, 2 wt-%, 3 wt-%, 4 wt-%, 5 wt-%, 6 wt-%, 7 wt-%, 8 wt-%, 9 wt-%, or 10 wt-%. In other embodiments, the second stabilizing agent has a concentration from about 0.5 wt-% to about 5 wt-%, e.g., 0.5 wt-%, 1 wt-%, 1.5 wt-%, 2 wt-%, 2.5 wt-%, 3 wt-%, 3.5 wt-%, 4 wt-%, 4.5 wt-% or 5 wt-%. In still other embodiments, the second stabilizing agent has a concentration from about 0.6 wt-% to about 1.8 wt-%, e.g., 0.6 wt-%, 0.7 wt-%, 0.8 wt-%, 0.9 wt-%, 1.0 wt-%, 1.1 wt-%, 1.2 wt-%, 1.3 wt-%, 1.4 wt-%, 1.5 wt-%, 1.6 wt-%, 1.7 wt-%, or 1.8 wt-%.

In some embodiments, the first stabilizing agent is a 2,6-pyridinedicarboxylic acid, or a salt thereof, and the second stabilizing agent is HEDP, or a salt thereof.

The present compositions can retain any suitable level or percentage of the $C_1$-$C_{22}$ percarboxylic acid activity for any suitable time after the composition is formed. In some embodiments, the present composition retains at least about 60%, 65%, 70%, 75%, 80%, 85% or 90% of the initial $C_1$-$C_{22}$ percarboxylic acid activity for any suitable time after the composition is formed. In other embodiments, the present composition retains at least about 60% of the initial $C_1$-$C_{22}$ percarboxylic acid activity for at least 1, 2, 3, 4, 5, 6, 7, 8, 9, 10, 11, 12, 13, 14, 15, 20, 25, 30 minutes, 1, 2, 5, 10, 15, 20 or 24 hours, or longer after the composition is formed.

In some embodiments, the present compositions can comprise a peroxidase or a catalase to further reduce the hydrogen peroxide concentration. Any suitable peroxidase or a catalase can be used in the present compositions. Exemplary peroxidases and catalases are described in the above Section B. In other embodiments, the present compositions can further comprise a substance that aids solubilization of the first and/or second stabilizing agent(s). Exemplary substances that can aid solubilization of the first and/or second stabilizing agent(s) include hydrotropes such as sodium xylene sulfonate, sodium cumene sulfonates, and surfactants, such as anionic surfactants and noinionic surfactants.

In another aspect, the present invention is directed to a method for high-viscosity fracturing, which method comprises directing the above composition into a subterranean environment.

The present methods can be used to direct the above composition into any suitable subterranean environment. In some embodiments, the present methods can be used to direct the above composition into a subterranean environment comprising a well in a gas and/or oil field.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

E. METHODS FOR TREATING A TARGET

In yet another aspect, the present invention is directed to a method for treating a target, which method comprises a step of contacting a target with a composition in a diluted level to form a treated target composition, wherein said composition comprises:
1) a $C_1$-$C_{22}$ carboxylic acid;
2) a $C_1$-$C_{22}$ percarboxylic acid;
3) hydrogen peroxide;
4) a first stabilizing agent, which is a picolinic acid or a compound having the following Formula (IA):

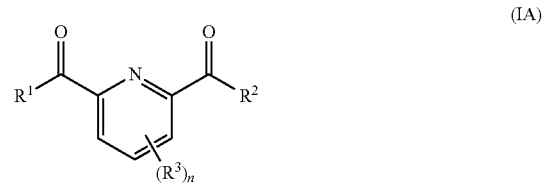

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and n is a number from zero to 3;
or a salt thereof;
or a compound having the following Formula (IB):

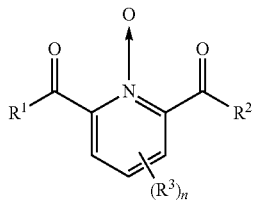

(IB)

wherein
R$^1$ is OH or —NR$^{1a}$R$^{1b}$, wherein R$^{1a}$ and R$^{1b}$ are independently hydrogen or (C$_1$-C$_6$)alkyl;
R$^2$ is OH or —NR$^{2a}$R$^{2b}$, wherein R$^{2a}$ and R$^{2b}$ are independently hydrogen or (C$_1$-C$_6$)alkyl;
each R$^3$ is independently (C$_1$-C$_6$)alkyl, (C$_2$-C$_6$)alkenyl or (C$_2$-C$_6$)alkynyl; and
n is a number from zero to 3; or a salt thereof;
5) a second stabilizing agent, which is a compound having the following Formula (IIA):

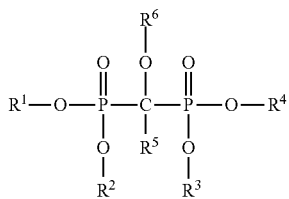

(IIA)

wherein
R$^1$, R$^2$, R$^3$, and R$^4$ are independently hydrogen, (C$_1$-C$_6$) alkyl, (C$_2$-C$_6$)alkenyl or (C$_2$-C$_6$)alkynyl, or C$_{6\text{-}20}$ aryl;
R$^5$ is (C$_1$-C$_6$)alkyl, (C$_2$-C$_6$)alkenyl or (C$_2$-C$_6$)alkynyl; and
R$^6$ is hydrogen, (C$_1$-C$_6$)alkyl, (C$_2$-C$_6$)alkenyl or (C$_2$-C$_6$)alkynyl;
or a salt thereof;
or a compound having the following Formula (IIB):

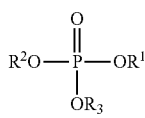

(IIB)

wherein
R$^1$, R$^2$, and R$^3$ are independently hydrogen, (C$_1$-C$_6$)alkyl, (C$_2$-C$_6$)alkenyl or (C$_2$-C$_6$)alkynyl, or C$_{6\text{-}20}$ aryl;
or a salt thereof; and
wherein said hydrogen peroxide has a concentration of at least about 0.1 wt-%, the C$_1$-C$_{22}$ percarboxylic acid has a concentration of at least about 2 times of the concentration of said hydrogen peroxide, and said composition has a pH at about 4 or less, and
wherein said treated target composition comprises from about 1 ppm to about 10,000 ppm of said C$_1$-C$_{22}$ percarboxylic acid, and said contacting step lasts for sufficient time to stabilize or reduce microbial population in and/or on said target or said treated target composition.

In some embodiments, the composition used in the present methods is an equilibrated composition that comprises peracid, hydrogen peroxide, carboxylic acid and a solvent, e.g., water. In some embodiments, the composition used in the present methods does not comprise a mineral acid, e.g., the mineral acids disclosed in WO 91/07375.

The composition used in the present methods can comprise any suitable level of the hydrogen peroxide. In some embodiments, the hydrogen peroxide in the equilibrated composition has a concentration of about 0.1% to about 15%, e.g., about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, or 15%. Prior to or during use, the exemplary compositions can be diluted to a desired level.

The composition used in the present methods can comprise any suitable level of the C$_1$-C$_{22}$ percarboxylic acid relative to the level of the hydrogen peroxide. In some embodiments, the C$_1$-C$_{22}$ percarboxylic acid has a concentration of at least about 6 times of the concentration of the hydrogen peroxide. In other embodiments, the C$_1$-C$_{22}$ percarboxylic acid has a concentration of at least about 10 times of the concentration of the hydrogen peroxide. In still other embodiments, the C$_1$-C$_{22}$ percarboxylic acid has a concentration of at least about 2, 3, 4, 5, 6, 7, 8, 9 or 10 times of the concentration of the hydrogen peroxide.

Any suitable C$_1$-C$_{22}$ percarboxylic acid can be used in the present methods. In some embodiments, the C$_1$-C$_{22}$ percarboxylic acid is a C$_2$-C$_{20}$ percarboxylic acid. In other embodiments, the C$_1$-C$_{22}$ percarboxylic acid comprises peroxyacetic acid, peroxyoctanoic acid and/or peroxysulfonated oleic acid. Other exemplary C$_1$-C$_{22}$ percarboxylic acids are described in the above Section B. The composition used in the present methods can comprise any suitable level of the C$_1$-C$_{22}$ percarboxylic acid and hydrogen peroxide. In some embodiments, the C$_1$-C$_{22}$ percarboxylic acid in the equilibrated composition has a concentration from about 0.1% to about 30%, e.g., about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%. Prior to or during use, the exemplary compositions can be diluted to a desired level.

Any suitable first stabilizing agent can be used in the composition used in the present methods. In some embodiments, the first stabilizing agent is a picolinic acid, or a salt thereof. In other embodiments, the first stabilizing agent is 2,6-pyridinedicarboxylic acid, or a salt thereof. The first stabilizing agent can be used at any suitable concentration. In some embodiments, the first stabilizing agent has a concentration from about 0.005 wt-% to about 5 wt-%. In other embodiments, the first stabilizing agent has a concentration from about 0.05 wt-% to about 0.15 wt-%. In still other embodiments, the first stabilizing agent has a concentration at about 0.005 wt-%, 0.01 wt-%, 0.1 wt-%, 1 wt-%, 2 wt-%, 3 wt-%, 4 wt-%, or 5 wt-%. In yet other embodiments, the first stabilizing agent has a concentration at about 0.05 wt-%, 0.06 wt-%, 0.07 wt-%, 0.08 wt-%, 0.09 wt-%, 0.10 wt-%, 0.11 wt-%, 0.12 wt-%, 0.13 wt-%, 0.14 wt-%, or 0.15 wt-%.

Any suitable second stabilizing agent can be used in the present compositions. In some embodiments, the second stabilizing agent is 1-hydroxy ethylidene-1,1-diphosphonic acid (HEDP), or a salt thereof. The second stabilizing agent can be used at any suitable concentration. In some embodiments, the second stabilizing agent has a concentration from about 0.1 wt-% to about 10 wt-%, e.g., 0.1 wt-%, 0.5 wt-%, 1 wt-%, 2 wt-%, 3 wt-%, 4 wt-%, 5 wt-%, 6 wt-%, 7 wt-%, 8 wt-%, 9 wt-%, or 10 wt-%. In other embodiments, the second stabilizing agent has a concentration from about 0.5 wt-% to about 5 wt-%, e.g., 0.5 wt-%, 1 wt-%, 1.5 wt-%, 2 wt-%, 2.5 wt-%, 3 wt-%, 3.5 wt-%, 4 wt-%, 4.5 wt-% or 5 wt-%. In still other embodiments, the second stabilizing agent has a concentration from about 0.6 wt-% to about 1.8 wt-%, e.g., 0.6 wt-%, 0.7 wt-%, 0.8 wt-%, 0.9 wt-%, 1.0 wt-%, 1.1 wt-%, 1.2 wt-%, 1.3 wt-%, 1.4 wt-%, 1.5 wt-%, 1.6 wt-%, 1.7 wt-%, or 1.8 wt-%.

In some embodiments, the first stabilizing agent is a 2,6-pyridinedicarboxylic acid, or a salt thereof, and the second stabilizing agent is HEDP, or a salt thereof.

The composition used in the present methods can retain any suitable level or percentage of the $C_1$-$C_{22}$ percarboxylic acid activity for any suitable time after the treated target composition is formed. In some embodiments, the present composition retains at least about 50%, 55%, 60%, 65%, 70%, 75%, 80%, 85% or 90% of the initial $C_1$-$C_{22}$ percarboxylic acid activity for any suitable time after the treated target composition is formed. In other embodiments, the present composition retains at least about 60% of the initial $C_1$-$C_{22}$ percarboxylic acid activity for at least 1, 2, 3, 4, 5, 6, 7, 8, 9, 10, 11, 12, 13, 14, 15, 20, 25, 30 minutes, 1, 2, 5, 10, 15, 20 or 24 hours, or longer after the treated target composition is formed.

In some embodiments, the composition used in the present methods can comprise a peroxidase or a catalase to further reduce the hydrogen peroxide concentration. Any suitable peroxidase or a catalase can be used in the present compositions. Exemplary peroxidases and catalases are described in the above Section B. In other embodiments, the composition used in the present methods can further comprise a substance that aids solubilization of the first and/or second stabilizing agent(s). Exemplary substances that can aid solubilization of the first and/or second stabilizing agent(s) include hydrotropes such as sodium xylene sulfonate, sodium cumene sulfonates, and surfactants, such as anionic surfactants and noinionic surfactants.

The present methods can be used for treating any suitable target. For example, the target can be a food item or a plant item and/or at least a portion of a medium, a container, an equipment, a system or a facility for growing, holding, processing, packaging, storing, transporting, preparing, cooking or serving the food item or the plant item.

The present methods can be used for treating any suitable plant item. In some embodiments, the plant item is a grain, fruit, vegetable or flower plant item. In other embodiments, the plant item is a living plant item or a harvested plant item. In still other embodiments, the plant item comprises a seed, a tuber, a growing plant, a cutting, or a root stock. In yet other embodiments, the present methods are used for treating a living plant tissue comprising treating the plant tissue with the above composition in a diluted level to stabilize or reduce microbial population in and/or on the plant tissue. In yet other embodiments, the present methods are used for growing a plant on a hydroponic substrate in a hydroponic liquid supply medium, comprising: (a) establishing a growing and living plant tissue in the hydroponic substrate; (b) contacting the living plant tissue, the hydroponic substrate and the hydroponic liquid with a diluted composition of the present invention to stabilize or reduce microbial population in and/or on the living plant tissue; and (c) harvesting a usable plant product with reduced microbial contamination.

The present methods can be used for treating any suitable food item. For example, the food item can be an animal product, e.g., an animal carcass or an egg, a fruit item, a vegetable item, or a grain item. In some embodiments, the animal carcass can be a beef, pork, veal, buffalo, lamb, fish, sea food or poultry carcass. In other embodiments, the sea food carcass can be scallop, shrimp, crab, octopus, mussel, squid or lobster. In still other embodiments, the fruit item can be a botanic fruit, a culinary fruit, a simple fruit, an aggregate fruit, a multiple fruit, a berry, an accessory fruit or a seedless fruit. In yet other embodiments, the vegetable item can be a flower bud, a seed, a leaf, a leaf sheath, a bud, a stem, a stem of leaves, a stem shoot, a tuber, a whole-plant sprout, a root or a bulb. In yet other embodiments, the grain item can be maize, rice, wheat, barley, sorghum, millet, oat, triticale, rye, buckwheat, fonio or quinoa.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

The treated target composition can comprise any suitable level of the $C_1$-$C_{22}$ percarboxylic acid. In some embodiments, the treated target composition comprises from about 10 ppm to about 200 ppm of the $C_1$-$C_{22}$ percarboxylic acid, e.g., about 10 ppm, 20 ppm, 30 ppm, 40 ppm, 50 ppm, 60 ppm, 70 ppm, 80 ppm, 90 ppm, 100 ppm, 110 ppm, 120 ppm, 130 ppm, 140 ppm, 150 ppm, 160 ppm, 170 ppm, 180 ppm, 190 ppm, or 200 ppm of the $C_1$-$C_{22}$ percarboxylic acid.

The treated target composition can comprise any suitable $C_1$-$C_{22}$ percarboxylic acid. In some embodiments, the treated target composition comprises peroxyacetic acid, peroxyoctanoic acid and/or peroxysulfonated oleic acid.

The treated target composition can comprise any suitable level of the hydrogen peroxide. In some embodiments, the treated target composition comprises from about 1 ppm to about 15 ppm of the hydrogen peroxide, e.g., about 1 ppm, 2 ppm, 3 ppm, 4 ppm, 5 ppm, 6 ppm, 7 ppm, 8 ppm, 9 ppm, 10 ppm, 11 ppm, 12 ppm, 13 ppm, 14 ppm, or 15 ppm of the hydrogen peroxide.

The treated target composition can comprise any suitable level of the $C_1$-$C_{22}$ percarboxylic acid relative to the level of the hydrogen peroxide. In some embodiments, the treated target composition comprises the $C_1$-$C_{22}$ percarboxylic acid that has a concentration of at least about 2, 3, 4, 5, 6, 7, 8, 9, 10, 11, 12, 13, 14, 15, 16, 17, 18, 19 or 20 times of the concentration of the hydrogen peroxide.

The treated target composition can comprise any suitable first stabilizing agent and second stabilizing agent. In some embodiments, the treated target composition comprises a first stabilizing agent that is a 2,6-pyridinedicarboxylic acid, or a salt thereof, and a second stabilizing agent that is HEDP, or a salt thereof.

The treated target composition can retain any suitable level of the initial $C_1$-$C_{22}$ percarboxylic acid activity for any suitable time. In some embodiments, the treated target composition retains at least about 50%, 60%, 70%, 80%, 90%, 95%, 99%, or 100% of the initial $C_1$-$C_{22}$ percarboxylic acid activity for any suitable time. In other embodiments, the treated target composition retains a suitable level of the initial $C_1$-$C_{22}$ percarboxylic acid activity for at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, or 15 minutes after the treated target composition is formed. In still other embodiments, the treated target composition retains at least about 60% of the initial $C_1$-$C_{22}$ percarboxylic acid activity for 15 minutes after the treated target composition is formed.

The contacting step can last for any suitable time. In some embodiments, the contacting step lasts for at least 10 seconds, 20 seconds, 30 seconds, 40 seconds, 50 seconds, 1 minute, 10 minutes, 30 minutes, 1 hour, 2 hours, 4 hours, 8 hours, 16 hours, 1 day, 3 days, 1 week, or longer.

The diluted composition can be applied to the target in any suitable manner. In some embodiments, the diluted composition is applied to the target by means of a spray, a fog, or a foam. In other embodiments, the diluted composition is applied to the target by applying in the form of a thickened or gelled solution. In still other embodiments, all or part of the target is dipped in the diluted composition. The target and/or the diluted composition can be subject to any suitable movement to help or facilitate the contact between the target and the diluted composition. In some embodiments, the diluted composition can be agitated. In other embodiments, the diluted composition can be sprayed onto a target, e.g., an animal carcass, under suitable pressure and at a suitable temperature. For example, the diluted composition can be sprayed onto an animal carcass at a pressure of at least 50 psi at a temperature of up to about 60° C., resulting in a contact time of at least 30 seconds.

The present methods can comprise any suitable, additional steps. In some embodiments, the present methods can comprise a vacuum treatment step. In other embodiments, the present methods can comprise a step of applying an activated light source to the target, e.g., an animal carcass.

The present methods can be used to achieve any suitable reduction of the microbial population in and/or on the target or the treated target composition. In some embodiments, the present methods can be used to reduce the microbial population in and/or on the target or the treated target composition by at least one $\log_{10}$. In other embodiments, the present methods can be used to reduce the microbial population in and/or on the target or the treated target composition by at least two $\log_{10}$. In still other embodiments, the present methods can be used to reduce the microbial population in and/or on the target or the treated target composition by at least three $\log_{10}$.

The present methods can be used to stabilize or reduce any suitable microbial population in and/or on the target or the treated target composition. In some embodiments, the present methods can be used to stabilize or reduce a prokaryotic microbial population in and/or on the target or the treated target composition. Exemplary prokaryotic microbial population can comprise a bacterial or an archaeal population. In other embodiments, the present methods can be used to stabilize or reduce an eukaryotic microbial population in and/or on the target or the treated target composition. Exemplary eukaryotic microbial population can comprise a protozoal or fungal population. In still other embodiments, the present methods can be used to stabilize or reduce a viral population in and/or on the target or the treated target composition. Exemplary viral population can comprise a population of a DNA virus, a RNA virus, and a reverse transcribing virus.

The present methods can be used to stabilize or reduce a microbial population in and/or on the target or the treated target composition, wherein the target is a food item or a plant item and the contacting step minimizes or does not induce an organoleptic effect in and/or on the food item or a plant item. Typical organoleptic properties include the aspects of food or other substances as experienced by the senses, including taste, sight, smell, and touch, in cases where dryness, moisture, and stale-fresh factors are to be considered. See e.g., Jasper Womach, the Congressional Research Service document "Report for Congress: Agriculture: A Glossary of Term, Programs, and Laws, 2005 Edition." In some embodiments, organoleptic procedures are performed as part of the meat and poultry inspections to detect signs of disease or contamination. In other embodiments, organoleptic tests are conducted to determine if package materials and components can transfer tastes and odors to the food or pharmaceutical products that they are packaged in. Shelf life studies often use taste, sight, and smell (in addition to food chemistry and toxicology tests) to determine whether a food product is suitable for consumption. In still other embodiments, organoleptic tests are conducted as part of the Hurdle technology. Typically, Hurdle technology refers to an intelligent combination of hurdles which secures the microbial safety and stability as well as the organoleptic and nutritional quality and the economic viability of food products. See generally, Leistner L (1995) "In Gould G W (Ed.) *New Methods of Food Preservation*, Springer, pp. 1-21; and Leistner I (2000)" *International Journal of Food Microbiology*, 55:181-186.

The present methods can be conducted at any suitable temperature. In some embodiments, the present methods are conducted at a temperature ranging from about 0° C. to about 70° C., e.g., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C.

The present methods can be used in the methods, processes or procedures described and/or claimed in U.S. Pat. Nos. 5,200,189, 5,314,687 and 5,718,910. In some embodiments, the present methods can be used of sanitizing facilities or equipment comprises the steps of contacting the facilities or equipment with the diluted (or use) composition of the present invention at a temperature in the range of about 4° C. to about 60° C. The diluted (or use) composition is then circulated or left in contact with the facilities or equipment for a time sufficient to sanitize (generally at least 30 seconds) and the treated target composition is thereafter drained or removed from the facilities or equipment.

As noted above, the present methods are useful in the cleaning or sanitizing of processing facilities or equipment in the food service, food processing or health care industries. Examples of process facilities in which the present methods can be employed include a milk line dairy, a continuous brewing system, food processing lines such as pumpable food systems and beverage lines, etc. Food service wares can also be disinfected with the present methods. The present methods are also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof.

Generally, the actual cleaning of the in-place system or other surface (i.e., removal of unwanted offal therein) can be accomplished with a different material such as a formulated detergent which is introduced with heated water. After this cleaning step, the present composition can be applied or introduced into the system at a use solution concentration in unheated, ambient temperature water. In some embodiments, the present composition is found to remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity.

In some embodiments, a method of sanitizing substantially fixed in-place process facilities comprises the following steps. The diluted (or use) composition of the present invention is introduced into the process facilities at a temperature in the range of about 4° C. to about 60° C. After introduction of the use solution, the solution is circulated throughout the system for a time sufficient to sanitize the process facilities (i.e., to kill undesirable microorganisms). After the system has been sanitized by means of the present composition, the use composition or solution is drained from the system. Upon completion of the sanitizing step, the system optionally may be rinsed with other materials such as potable water. The present composition is preferably circulated through the process facilities for 10 minutes or less.

In other embodiments, the present composition may also be employed by dipping food processing equipment into the diluted (or use) composition or solution of the present invention, soaking the equipment for a time sufficient to sanitize the equipment, and wiping or draining excess solution off the equipment. The composition may be further employed by spraying or wiping food processing surfaces with the use solution, keeping the surfaces wet for a time sufficient to sanitize the surfaces, and removing the excess composition or solution by wiping, draining vertically, vacuuming, etc.

In still other embodiments, the present composition may also be used in a method of sanitizing hard surfaces such as institutional type equipment, utensils, dishes, health care equipment or tools, and other hard surfaces. The present composition may also be employed in sanitizing clothing items or fabric which has become contaminated. The use composition is contacted with any of the above contaminated surfaces or items at use temperatures in the range of about 4° C. to about 60° C. for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess composition or solution can then be removed by rinsing or centrifuging the fabric.

The present methods can be used in the methods, processes or procedures described and/or claimed in U.S. Pat. Nos. 6,165,483 and 6,238,685B1, to treat field or greenhouse grown plant tissue, seeds, fruits, and growing media and containers. The present composition in diluted (or use) form can lower the natural, plant pathogen and human pathogenic microbial load resulting in less waste to molding, spoilage, and destruction because of pathogenic poisons.

In some embodiments, the present composition comprising mixed peracids can be used to protect growing plant tissue from the undesirable effects of microbial attack. The mixed peracid materials can be applied to growing plant tissues and can provide residual antimicrobial effects after the plant has completed its growth cycle, fruit or vegetable material have been harvested and sent to market. The present composition comprising mixed peracids can be an effective treatment of living or growing plant tissues including seeds, roots, tubers, seedlings, cuttings, rooting stock, growing plants, produce, fruits and vegetables, etc. Under certain circumstances, a single peroxyacid material can be effective, however, in other circumstances, a mixed peroxy acid has substantially improved and surprising properties.

In some embodiments, the invention involves a peroxyacid antimicrobial concentrate and diluted end use composition including an effective microbicidal amount of a $C_2$-$C_4$ peroxycarboxylic acid such as peracetic acid, an effective microbicidal amount of a $C_5$-$C_{12}$ peroxyacid, preferably with a $C_6$-$C_{12}$ or a $C_8$-$C_{12}$ peroxy acid, or mixtures thereof, and the first and second stabilizing agents described above. The concentrate composition can be diluted with a major proportion of water to form an antimicrobial sanitizing use solution having a pH in the range of about 2 to 8, with a $C_2$-$C_4$ peroxycarboxylic acid concentration of at least about 4 ppm, preferably about 10 to 75 ppm, and a $C_5$-$C_{12}$, a $C_6$-$C_{12}$, or a $C_8$-$C_{12}$ peroxyacid concentration of at least about 1 ppm, preferably about 1 to 25 ppm. Other components may be added such as a hydrotrope coupling agent for solubilizing the peroxyfatty acid in the concentrate form and when the concentrate composition is diluted with water.

In other embodiments, the invention involves a method of controlling fungi and microbial plant pathogens in growing plants by treating said growing plants with a dilute aqueous solution comprising an effective amount of a $C_2$-$C_4$ peroxycarboxylic acid, an aliphatic $C_5$-$C_{12}$, a $C_6$-$C_{12}$ or a $C_8$-$C_{12}$ peroxycarboxylic acid, and the first and second stabilizing agents described above.

In still other embodiments, the invention further involves a process for controlling fungi and microbial plant pathogens in growing plants by diluting in an aqueous liquid a concentrate containing: about 1 to 20 wt-% of a $C_2$-$C_4$ peroxycarboxylic acid; about 0.1 to 20 wt-% of an aliphatic $C_5$-$C_{12}$, a $C_6$-$C_{12}$ or a $C_8$-$C_{12}$ peroxycarboxylic acid, and the first and second stabilizing agents described above, to form a solution; and contacting said growing plants with said solution.

In yet other embodiments, the invention further involves a process for controlling fungi and microbial plant pathogens in growing plants by diluting in an aqueous liquid a concentrate containing: about 1 to 20 wt-% of a $C_2$-$C_4$ peroxycarboxylic acid; about 0.1 to 20 wt-% of an aliphatic $C_5$-$C_{12}$, a $C_6$-$C_{12}$ or a $C_8$-$C_{12}$ peroxycarboxylic acid; about 5 to 40 wt-% of a $C_2$-$C_4$ carboxylic acid; about 1 to 20 wt-% of an aliphatic $C_8$-$C_{12}$ carboxylic acid; about 1 to 30 wt-% of hydrogen peroxide, and the first and second stabilizing agents described above, to form a solution; and contacting said growing plants with said solution.

As disclosed in U.S. Pat. Nos. 6,165,483 and 6,238,685B1, a low pH, (e.g., preferably less than 7) $C_5$+ peroxyacids such as peroxyfatty acids are very potent biocides at low levels when used in combination with a $C_2$-$C_4$ peroxycarboxylic acid such as peroxyacetic acid, a synergistic effect is obtained, providing a much more potent biocide than can be obtained by using these components separately. This means that substantially lower concentrations of biocide can be used to obtain equal biocidal effects.

As the term is used herein, a $C_5$-$C_{12}$ peroxyacid (or peracid) is intended to mean the product of the oxidation of a $C_5$-$C_{12}$ acid such as a fatty acid, or a mixture of acids, to form a peroxyacid having from about 5 to 12 carbon atoms per molecule. The $C_5$-$C_{12}$ peroxyacids are preferably aliphatic (straight or branched). A $C_2$-$C_4$ peroxycarboxylic acid is intended to mean the product of oxidation of a $C_2$-$C_4$ carboxylic acid, or a mixture thereof. This includes both straight and branched a $C_2$-$C_4$ carboxylic acids.

In yet other embodiments, the invention is directed a method of controlling fungi and microbial plant pathogens in growing plants. This treatment utilizes a combination of two different peroxy acids. This mixture comprises at least 4 parts per million (ppm) of a smaller $C_2$-$C_4$ peroxy carboxylic acid and at least 1 ppm of a larger $C_5$-$C_{12}$ peroxy carboxylic acid, and the first and second stabilizing agents described above. The preferred mixture comprises at least 4 ppm of a smaller $C_2$-$C_4$ peroxy acid and at least 1 ppm of a large aliphatic $C_8$-$C_{12}$ peroxy acid, and the first and second stabilizing agents described above.

An especially preferred embodiment of the composition includes a mixture of peroxyacetic acid and peroctanoic acid.

In some embodiments, the composition used in the present methods also may contain a hydrotrope for the purpose of increasing the aqueous solubility of various slightly soluble organic compounds. The preferred embodiment of the composition utilizes a hydrotrope chosen from the group of n-octanesulfonate, a xylene sulfonate, a naphthalene sulfonate, ethylhexyl sulfate, lauryl sulfate, an amine oxide, or a mixture thereof.

In some embodiments, the composition used in the present methods may also contain a chelating agent for the purpose of removing ions from solution. The preferred embodiment of the invention uses 1-hydroxyethylidene-1,1-diphosphonic acid.

In some embodiments, the invention also provides a process of controlling fungi and microbial plant pathogens in growing plants. In this embodiment, the plant is contacted with a solution made by diluting in an aqueous liquid a concentrate comprising two peroxy acids, and the first and second stabilizing agents described above. This mixture includes $C_2$-$C_4$ peroxy carboxylic acid and a larger $C_8$-$C_{12}$ peroxy carboxylic acid. The preferred mixture includes about 1-20 weight percent (wt %) of a smaller $C_2$-$C_4$ peroxy acid and about 0.1-20 wt % of a larger $C_8$-$C_{12}$ peroxy acid. An especially preferred embodiment of the composition includes a mixture of peroxyacetic acid and peroxyoctanoic acid. The composition may further contain about 1-15 wt % of a hydrotrope and about 5 wt-% of a chelating agent.

In other embodiments, the invention also provides a process of controlling fungi and microbial plant pathogens in growing plants. In this embodiment, the plant is contacted with a solution made by diluting in an aqueous liquid a concentrate containing two peroxy acids, and the first and second stabilizing agents described above. This mixture includes a smaller $C_2$-$C_4$ peroxy carboxylic acid and a larger $C_8$-$C_{12}$ aliphatic peroxy carboxylic acid. An especially preferred embodiment of the composition includes a mixture of peroxyacetic acid and peroctanoic acid. The composition may further contain a hydrotrope and a chelating agent. Further, the solution contains about 1-30 wt % of hydrogen peroxide. The preferred composition includes a mixture of acetic acid and octanoic acid.

The present methods can be used in the methods, processes or procedures described and/or claimed in U.S. Pat. Nos. 6,010,729, 6,103,286, 6,545,047 and 8,030,351 B2 for sanitizing animal carcasses.

In some embodiments, the compositions of the present invention can be used in a method of treating animal carcasses to obtain a reduction by at least one $\log_{10}$ in surface microbial population which method includes the step of treating said carcass with a diluted composition of the present invention comprising an effective antimicrobial amount comprising at least 2 parts per million (ppm, parts by weight per each one million parts) of one or more peroxycarboxylic acids having up to 12 carbon atoms, an effective antimicrobial amount comprising at least 20 ppm of one or more carboxylic acids having up to 18 carbon atoms, and the first and second stabilizing agents described above, to reduce the microbial population.

In other embodiments, the present invention is directed to an antimicrobial composition adapted for cleaning and sanitizing animal carcasses which contains about 0.5 weight percent (wt-%) to about 20 wt-% of a mixture of one or more peroxycarboxylic acids having from 2-4 carbon atoms, and one or more peroxycarboxylic acids having from 8-12 carbon atoms, from about 0.5 wt-% to about 60 wt-% of an alpha-hydroxy mono or dicarboxylic acid having 3-6 carbon atoms, an effective amount of a sequestrant, an effective amount of a hydrotrope, and the first and second stabilizing agents described above.

In still other embodiments, the present invention is directed to an antimicrobial composition adapted for treating animal carcasses comprising, consisting essentially of, or consisting of a mixture of peroxyacetic and peroxyoctanoic acid in a ratio of about 10:1 to about 1:1, from about 0.1 to about 10 wt-% of acetic acid, from about 4 wt-% to about 10 wt-% of hydrogen peroxide and from about 0.5 wt-% to about 1.5 wt-% of a sequestering agent, and the first and second stabilizing agents described above.

In yet other embodiments, the present invention is directed to a method of treating an animal carcass to reduce a microbial population in resulting cut meat, the method comprising the steps of spraying an aqueous antimicrobial treatment composition onto said carcass at a pressure of at least 50 psi at a temperature of up to about 60° C. resulting in a contact time of at least 30 seconds, the antimicrobial composition comprising an effective antimicrobial amount comprising least 2 ppm of one or more carboxylic acid, peroxycarboxylic acid or mixtures thereof, and the first and second stabilizing agents described above; and achieving at least a one $\log_{10}$ reduction in the microbial population.

In yet other embodiments, the present invention is directed to a method of treating an animal carcass to reduce a microbial population in resulting cut meat, the method comprising the steps of placing the animal carcass in a chamber at atmospheric pressure; filling the chamber with condensing steam comprising an antimicrobial composition, e.g., a diluted composition of the present invention, for a short duration; and quickly venting and cooling the chamber to prevent browning of the meat carcass; wherein the duration of the steam thermal process may be from about 5 seconds to about 30 seconds and the chamber temperature may reach from about 50° C. to about 93° C.

The antimicrobial composition can be applied in various ways to obtain intimate contact with each potential place of microbial contamination. For example, it can be sprayed on the carcasses, or the carcasses can be immersed in the composition. Additional methods include applying a foamed composition and a thickened or gelled composition. Vacuum and or light treatments can be included, if desired, with the application of the antimicrobial composition. Thermal treatment can also be applied, either pre-, concurrent with or post application of the antimicrobial composition.

One preferred spray method for treating carcasses with diluted compositions of the present invention involves spraying the carcass with an aqueous spray at a temperature less than about 60° C. at a pressure of about 50 to 500 psi gauge wherein the spray comprises an effective antimicrobial amount of a carboxylic acid, an effective antimicrobial amount of a peroxycarboxylic acid or mixtures thereof, and the first and second stabilizing agents described above. These sprays can also contain an effective portion of a peroxy compound such as hydrogen peroxide and other ingredients such as sequestering agents, etc. The high pressure spray action of the aqueous treatment can remove microbial populations by combining the mechanical action of the spray with the chemical action of the antimicrobial materials to result in an improved reduction of such populations on the surface of the carcass.

All pressures are psig (or psi gauge). In some embodiments, differentiation of antimicrobial "-cidal" or "-static" activity, the definitions which describe the degree of efficacy, and the official laboratory protocols for measuring this efficacy are important considerations for understanding the relevance of antimicrobial agents in compositions. Antimicrobial compositions may effect two kinds of microbial cell damages. The first is a truly lethal, irreversible action resulting in complete microbial cell destruction or incapacitation. The second type of cell damage is reversible, such that if the organism is rendered free of the agent, it can again multiply. The former is termed bacteriocidal and the latter, bacteriostatic. A sanitizer and a disinfectant are, by definition, agents which provide antibacterial or bacteriocidal activity and achieve at least a five-fold reduction (i.e., a five log 10 reduction) in microbial populations after a 30 second contact time (see AOAC method 960.09).

The present methods can be used in the methods, processes or procedures described and/or claimed in U.S. Pat. Nos. 8,017,409 and 8,236,573. In some embodiments, the present methods may be used for a variety of domestic or industrial applications, e.g., to reduce microbial or viral populations on a surface or object or in a body or stream of water. The diluted (or use) compositions of the present invention may be applied in a variety of areas including kitchens, bathrooms, factories, hospitals, dental offices and food plants, and may be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces may be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces may be made from a variety of materials including, for example, paper, fiber, woven or non-woven fabric, soft plastics and elastomers. The diluted (or use) compositions may also be applied to soft surfaces such as food and skin (e.g., a hand). The diluted (or use) compositions may be employed as a foaming or non-foaming environmental sanitizer or disinfectant.

In other embodiments, the diluted (or use) compositions of the present invention may be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

In still other embodiments, the diluted (or use) compositions of the present invention may also be used in veterinary products such as mammalian skin treatments or in products for sanitizing or disinfecting animal enclosures, pens, watering stations, and veterinary treatment areas such as inspection tables and operation rooms. The diluted (or use) compositions may be employed in an antimicrobial foot bath for livestock or people.

In yet other embodiments, the present methods may be employed for reducing the population of pathogenic microorganisms, such as pathogens of humans, animals, and the like. Exemplary pathogenic microorganisms include fungi, molds, bacteria, spores, and viruses, for example, *S. aureus, E. coli, Streptococci, Legionella, Pseudomonas aeruginosa*, mycobacteria, tuberculosis, phages, or the like. Such pathogens may cause a varieties of diseases and disorders, including Mastitis or other mammalian milking diseases, tuberculosis, and the like. The present methods may be used to reduce the population of microorganisms on skin or other external or mucosal surfaces of an animal. In addition, the present methods may be used to kill pathogenic microorganisms that spread through transfer by water, air, or a surface substrate. In some applications, the diluted (or use) compositions of the present invention need only be applied to the skin, other external or mucosal surfaces of an animal water, air, or surface.

In yet other embodiments, the present methods may also be used on foods and plant species to reduce surface microbial populations; used at manufacturing or processing sites handling such foods and plant species; or used to treat process waters around such sites. For example, the present methods may be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The present methods may be used to treat transport waters such as those found in flumes, pipe transports, cutters, slicers, blanchers, retort systems, washers, and the like. Particular foodstuffs that may be treated with the present methods include eggs, meats, seeds, leaves, fruits and vegetables. Particular plant surfaces include both harvested and growing leaves, roots, seeds, skins or shells, stems, stalks, tubers, corms, fruit, and the like. The present methods may also be used to treat animal carcasses to reduce both pathogenic and non-pathogenic microbial levels.

In yet other embodiments, the present methods may be useful in the cleaning or sanitizing of containers, processing facilities, or equipment in the food service or food processing industries. The present methods may be used on food packaging materials and equipment, including for cold or hot aseptic packaging. Examples of process facilities in which the present methods may be employed include a milk line dairy, a continuous brewing system, food processing lines such as pumpable food systems and beverage lines, etc. Food service wares may be disinfected with the present methods. For example, the present methods may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

In yet other embodiments, the present methods may also be used on or in other industrial equipment and in other industrial process streams such as heaters, cooling towers, boilers, retort waters, rinse waters, aseptic packaging wash waters, and the like. The present methods may be used to treat microbes and odors in recreational waters such as in pools, spas, recreational flumes and water slides, fountains, and the like.

In yet other embodiments, a filter containing the diluted (or use) compositions of the present invention may be used to reduce the population of microorganisms in air and liquids. Such a filter may be used to remove water and air-born pathogens such as *Legionella*.

In yet other embodiments, the present methods may be employed for reducing the population of microbes, fruit flies, or other insect larva on a drain or other surface.

In yet other embodiments, the present methods may also be employed by dipping food processing equipment into the diluted (or use) composition or solution of the present invention, soaking the equipment for a time sufficient to sanitize the equipment, and wiping or draining excess composition or solution off the equipment. The present methods may be further employed by spraying or wiping food processing surfaces with the use composition or solution, keeping the surfaces wet for a time sufficient to sanitize the surfaces, and removing excess composition or solution by wiping, draining vertically, vacuuming, etc.

In yet other embodiments, the present methods may also be used for sanitizing hard surfaces such as institutional type equipment, utensils, dishes, health care equipment or tools, and other hard surfaces. The present methods may also be employed in sanitizing clothing items or fabrics which have become contaminated. The diluted (or use) compositions of the present invention can be contacted with any contaminated surfaces or items at use temperatures in the range of about 4° C. to 60° C., for a period of time effective to sanitize, disinfect, or sterilize the surface or item. For example, the diluted (or use) compositions may be injected into the wash or rinse water of a laundry machine and contacted with contaminated fabric for a time sufficient to sanitize the fabric. Excess composition may be removed by rinsing or centrifuging the fabric.

In yet other embodiments, the diluted (or use) compositions of the present invention may be applied to microbes or to soiled or cleaned surfaces using a variety of methods. These methods may operate on an object, surface, in a body or stream of water or a gas, or the like, by contacting the object, surface, body, or stream with the diluted (or use) composition. Contacting may include any of numerous methods for applying a composition, such as spraying the composition, immersing the object in the composition, foam or gel treating the object with the composition, or a combination thereof.

In yet other embodiments, the diluted (or use) compositions of the present invention may be employed for bleaching pulp. The compositions may be employed for waste treatment. Such a composition may include added bleaching agent.

In yet other embodiments, other hard surface cleaning applications for the diluted (or use) compositions of the present invention include clean-in-place systems (CIP), clean-out-of-place systems (COP), washer-decontaminators, sterilizers, textile laundry machines, ultra and nano-filtration systems and indoor air filters. COP systems may include readily accessible systems including wash tanks, soaking vessels, mop buckets, holding tanks, scrub sinks, vehicle parts washers, non-continuous batch washers and systems, and the like.

The concentrations of peracid and/or hydrogen peroxide in the diluted (or use) compositions of the present invention can be monitored in any suitable manner. In some embodiments, the concentrations of peracid and/or hydrogen peroxide in the diluted (or use) compositions can be monitored using a kinetic assay procedure, e.g., the exemplary procedure disclosed in U.S. Pat. Nos. 8,017,409 and 8,236,573. This can be accomplished by exploiting the difference in reaction rates between peracid and hydrogen peroxide when using, for example, a buffered iodide reagent to differentiate peracid and hydrogen peroxide concentrations when both these analyte compounds are present in the use composition. The use composition monitor may also determine the concentrations of peracid and/or hydrogen peroxide in the presence of other additional ingredients, such as acidulants, one or more stabilizing agents, nonionic surfactants, semi-polar nonionic surfactants, anionic surfactants, amphoteric or ampholytic surfactants, adjuvants, solvents, additional antimicrobial agents or other ingredients which may be present in the use composition.

In some embodiments, exemplary compositions of the present invention comprise the components set forth in the following Tables 1-3. Prior to or during use, the exemplary compositions can be diluted to a desired level. For example, the exemplary compositions can be diluted by 2, 5, 10, 50, 100, 500, 1,000, 5,000, or 10,000 folds.

TABLE 1

Vortexx ES with DPA

| Formula (pre-equilibrium) | |
| --- | --- |
| Acetic Acid | 59.00% |
| Octanoic Acid | 10.00% |
| Hydrogen Peroxide (35%) | 30.00% |
| DPA (100%) | 0.04% |
| HEDP (60%) | 0.96% |
| Water | 0.00% |
| Total | 100.00% |
| Equilibrium Concentrations | |
| Acetic Acid | 48.54% |
| Peracetic Acid | 13.25% |
| Octanoic Acid | 8.74% |
| Peroctanoic Acid | 1.40% |
| Hydrogen Peroxide | 4.00% |
| DPA (100%) | 0.04% |
| HEDP | 0.58% |
| Water | 23.45% |
| Total | 100.00% |

TABLE 2

KX-6145 (Inspexx 100)

| Formula (pre-equilibrium) | |
| --- | --- |
| Acetic Acid | 55.00% |
| Octanoic Acid | 4.00% |
| Hydrogen Peroxide (35%) | 30.00% |
| DPA (100%) | 0.04% |
| HEDP (60%) | 1.00% |
| Water | 9.96% |
| Total | 100.00% |
| Equilibrium Concentrations | |
| Acetic Acid | 45.53% |
| Peracetic Acid | 12.00% |
| Octanoic Acid | 3.28% |

TABLE 2-continued

| KX-6145 (Inspexx 100) | |
|---|---|
| Peroctanoic Acid | 0.80% |
| Hydrogen Peroxide | 6.20% |
| DPA | 0.04% |
| HEDP | 0.60% |
| Water | 31.55% |
| Total | 100.00% |

TABLE 3

| Tsunami 200 (Falcon 15AO) | |
|---|---|
| Formula (pre-equilibrium) | |
| Acetic Acid | 53.96% |
| Octanoic Acid | 15.00% |
| Hydrogen Peroxide (35%) | 30.00% |
| DPA (100%) | 0.04% |
| HEDP (60%) | 1.00% |
| Water | 0.00% |
| Total | 100.00% |
| Equilibrium Concentrations | |
| Acetic Acid | 43.93 |
| Peracetic Acid | 12.75% |
| Octanoic Acid | 12.75% |
| Peroctanoic Acid | 2.50% |
| Hydrogen Peroxide | 4.25% |
| DPA | 0.04% |
| HEDP | 0.60% |
| Water | 23.18% |
| Total | 100.00% |

F. METHODS FOR REDUCING THE LEVEL OF HYDROGEN SULFIDE

In yet another aspect, the present invention is directed to a method for reducing the level of hydrogen sulfide ($H_2S$), hydrosulfuric acid or a salt thereof in a water source, which method comprises a step of contacting a water source with a composition in a diluted level to form a treated water source, wherein said composition comprises:

1) a $C_1$-$C_{22}$ carboxylic acid;
2) a $C_1$-$C_{22}$ percarboxylic acid;
3) hydrogen peroxide;
4) a first stabilizing agent, which is a picolinic acid or a compound having the following Formula (IA):

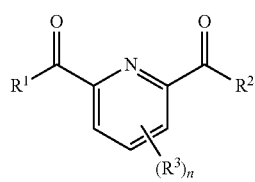

(IA)

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
or a compound having the following Formula (IB):

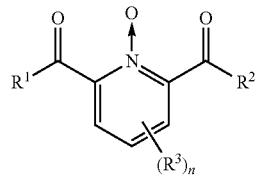

(IB)

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
6) a second stabilizing agent, which is a compound having the following Formula (IIA):

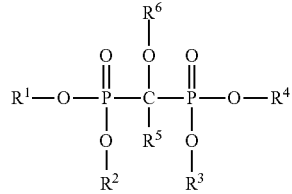

(IIA)

wherein
$R^1$, $R^2$, $R^3$, and $R^4$ are independently hydrogen, ($C_1$-$C_6$) alkyl, ($C_2$-$C_6$)alkenyl or ($C_2$-$C_6$)alkynyl, or $C_{6-20}$ aryl;
$R^5$ is ($C_1$-$C_6$)alkyl, ($C_2$-$C_6$)alkenyl or ($C_2$-$C_6$)alkynyl; and
$R^6$ is hydrogen, ($C_1$-$C_6$)alkyl, ($C_2$-$C_6$)alkenyl or ($C_2$-$C_6$) alkynyl;
or a salt thereof;
or a compound having the following Formula (IIB):

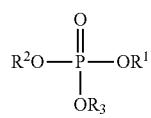

(IIB)

wherein
$R^1$, $R^2$, and $R^3$ are independently hydrogen, ($C_1$-$C_6$)alkyl, ($C_2$-$C_6$)alkenyl or ($C_2$-$C_6$)alkynyl, or $C_{6-20}$ aryl;
or a salt thereof; and
wherein said hydrogen peroxide has a concentration of at least about 0.1 wt-%, the $C_1$-$C_{22}$ percarboxylic acid has a concentration of at least about 2 times of the concentration of said hydrogen peroxide, and said composition has a pH at about 4 or less, and
wherein said treated water source comprises from about 1 ppm to about 10,000 ppm of said $C_1$-$C_{22}$ percarboxylic acid, and said contacting step lasts for sufficient time to stabilize or reduce the level of $H_2S$, hydrosulfuric acid or a salt thereof in said treated water source.

In some embodiments, the composition used in the present methods is an equilibrated composition that comprises peracid, hydrogen peroxide, carboxylic acid and a solvent, e.g., water. In some embodiments, the composition used in the present methods does not comprise a mineral acid, e.g., the mineral acids disclosed in WO 91/07375.

The composition used in the present methods can comprise any suitable level of the hydrogen peroxide. In some embodiments, the hydrogen peroxide in the equilibrated composition has a concentration of about 0.1% to about 15%, e.g., about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, or 15%. Prior to or during use, the exemplary compositions can be diluted to a desired level.

The composition used in the present methods can comprise any suitable level of the $C_1$-$C_{22}$ percarboxylic acid relative to the level of the hydrogen peroxide. In some embodiments, the $C_1$-$C_{22}$ percarboxylic acid has a concentration of at least about 6 times of the concentration of the hydrogen peroxide. In other embodiments, the $C_1$-$C_{22}$ percarboxylic acid has a concentration of at least about 10 times of the concentration of the hydrogen peroxide. In still other embodiments, the $C_1$-$C_{22}$ percarboxylic acid has a concentration of at least about 2, 3, 4, 5, 6, 7, 8, 9 or 10 times of the concentration of the hydrogen peroxide.

Any suitable $C_1$-$C_{22}$ percarboxylic acid can be used in the present methods. In some embodiments, the $C_1$-$C_{22}$ percarboxylic acid is a $C_2$-$C_{20}$ percarboxylic acid. In other embodiments, the $C_1$-$C_{22}$ percarboxylic acid comprises peroxyacetic acid, peroxyoctanoic acid and/or peroxysulfonated oleic acid. Other exemplary $C_1$-$C_{22}$ percarboxylic acids are described in the above Section B. The composition used in the present methods can comprise any suitable level of the $C_1$-$C_{22}$ percarboxylic acid and hydrogen peroxide. In some embodiments, the $C_1$-$C_{22}$ percarboxylic acid in the equilibrated composition has a concentration from about 0.1% to about 30%, e.g., about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%. Prior to or during use, the exemplary compositions can be diluted to a desired level.

Any suitable first stabilizing agent can be used in the composition used in the present methods. In some embodiments, the first stabilizing agent is a picolinic acid, or a salt thereof. In other embodiments, the first stabilizing agent is 2,6-pyridinedicarboxylic acid, or a salt thereof. The first stabilizing agent can be used at any suitable concentration. In some embodiments, the first stabilizing agent has a concentration from about 0.005 wt-% to about 5 wt-%. In other embodiments, the first stabilizing agent has a concentration from about 0.05 wt-% to about 0.15 wt-%. In still other embodiments, the first stabilizing agent has a concentration at about 0.005 wt-%, 0.01 wt-%, 0.1 wt-%, 1 wt-%, 2 wt-%, 3 wt-%, 4 wt-%, or 5 wt-%. In yet other embodiments, the first stabilizing agent has a concentration at about 0.05 wt-%, 0.06 wt-%, 0.07 wt-%, 0.08 wt-%, 0.09 wt-%, 0.10 wt-%, 0.11 wt-%, 0.12 wt-%, 0.13 wt-%, 0.14 wt-%, or 0.15 wt-%.

Any suitable second stabilizing agent can be used in the present compositions. In some embodiments, the second stabilizing agent is 1-hydroxy ethylidene-1,1-diphosphonic acid (HEDP), or a salt thereof. The second stabilizing agent can be used at any suitable concentration. In some embodiments, the second stabilizing agent has a concentration from about 0.1 wt-% to about 10 wt-%, e.g., 0.1 wt-%, 0.5 wt-%, 1 wt-%, 2 wt-%, 3 wt-%, 4 wt-%, 5 wt-%, 6 wt-%, 7 wt-%, 8 wt-%, 9 wt-%, or 10 wt-%. In other embodiments, the second stabilizing agent has a concentration from about 0.5 wt-% to about 5 wt-%, e.g., 0.5 wt-%, 1 wt-%, 1.5 wt-%, 2 wt-%, 2.5 wt-%, 3 wt-%, 3.5 wt-%, 4 wt-%, 4.5 wt-% or 5 wt-%. In still other embodiments, the second stabilizing agent has a concentration from about 0.6 wt-% to about 1.8 wt-%, e.g., 0.6 wt-%, 0.7 wt-%, 0.8 wt-%, 0.9 wt-%, 1.0 wt-%, 1.1 wt-%, 1.2 wt-%, 1.3 wt-%, 1.4 wt-%, 1.5 wt-%, 1.6 wt-%, 1.7 wt-%, or 1.8 wt-%.

In some embodiments, the first stabilizing agent is a 2,6-pyridinedicarboxylic acid, or a salt thereof, and the second stabilizing agent is HEDP, or a salt thereof.

The composition used in the present methods can retain any suitable level or percentage of the $C_1$-$C_{22}$ percarboxylic acid activity for any suitable time after the treated target composition is formed. In some embodiments, the present composition retains at least about 50%, 55%, 60%, 65%, 70%, 75%, 80%, 85% or 90% of the initial $C_1$-$C_{22}$ percarboxylic acid activity for any suitable time after the treated target composition is formed. In other embodiments, the present composition retains at least about 60% of the initial $C_1$-$C_{22}$ percarboxylic acid activity for at least 1, 2, 3, 4, 5, 6, 7, 8, 9, 10, 11, 12, 13, 14, 15, 20, 25, 30 minutes, 1, 2, 5, 10, 15, 20 or 24 hours, or longer after the treated target composition is formed.

In some embodiments, the composition used in the present methods can comprise a peroxidase or a catalase to further reduce the hydrogen peroxide concentration. Any suitable peroxidase or a catalase can be used in the present compositions. Exemplary peroxidases and catalases are described in the above Section B. In other embodiments, the composition used in the present methods can further comprise a substance that aids solubilization of the first and/or second stabilizing agent(s). Exemplary substances that can aid solubilization of the first and/or second stabilizing agent(s) include hydrotropes such as sodium xylene sulfonate, sodium cumene sulfonates, and surfactants, such as anionic surfactants and noinionic surfactants.

The treated water source can comprise any suitable level of the $C_1$-$C_{22}$ percarboxylic acid. In some embodiments, the treated water source comprises from about 10 ppm to about 1,000 ppm of the $C_1$-$C_{22}$ percarboxylic acid, e.g., about 10 ppm, 20 ppm, 30 ppm, 40 ppm, 50 ppm, 60 ppm, 70 ppm, 80 ppm, 90 ppm, 100 ppm, 110 ppm, 120 ppm, 130 ppm, 140 ppm, 150 ppm, 160 ppm, 170 ppm, 180 ppm, 190 ppm, 200 ppm, 300 ppm, 400 ppm, 500 ppm, 600 ppm, 700 ppm, 800 ppm, 900 ppm, or 1,000 ppm of the $C_1$-$C_{22}$ percarboxylic acid.

The treated water source can comprise any suitable $C_1$-$C_{22}$ percarboxylic acid. In some embodiments, the treated target composition comprises peroxyacetic acid, peroxyoctanoic acid and/or peroxysulfonated oleic acid.

The treated water source can comprise any suitable level of the hydrogen peroxide. In some embodiments, the treated water source comprises from about 1 ppm to about 15 ppm of the hydrogen peroxide, e.g., about 1 ppm, 2 ppm, 3 ppm, 4 ppm, 5 ppm, 6 ppm, 7 ppm, 8 ppm, 9 ppm, 10 ppm, 11 ppm, 12 ppm, 13 ppm, 14 ppm, or 15 ppm of the hydrogen peroxide.

The treated water source can comprise any suitable level of the $C_1$-$C_{22}$ percarboxylic acid relative to the level of the hydrogen peroxide. In some embodiments, the treated water source comprises the $C_1$-$C_{22}$ percarboxylic acid that has a concentration of at least about 2, 3, 4, 5, 6, 7, 8, 9, 10, 11, 12, 13, 14, 15, 16, 17, 18, 19 or 20 times of the concentration of the hydrogen peroxide.

The treated water source can comprise any suitable first stabilizing agent and second stabilizing agent. In some embodiments, the treated water source comprises a first stabilizing agent that is a 2,6-pyridinedicarboxylic acid, or a salt thereof, and a second stabilizing agent that is HEDP, or a salt thereof.

The treated water source can retain any suitable level of the initial $C_1$-$C_{22}$ percarboxylic acid activity for any suitable time. In some embodiments, the treated water source retains at least about 50%, 60%, 70%, 80%, 90%, 95%, 99%, or 100% of the initial $C_1$-$C_{22}$ percarboxylic acid activity for any suitable time. In other embodiments, the treated water source retains a suitable level of the initial $C_1$-$C_{22}$ percarboxylic acid activity for at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, or 15 minutes after the treated target composition is formed. In still other embodiments, the treated water source retains at least about 60% of the initial $C_1$-$C_{22}$ percarboxylic acid activity for 15 minutes after the treated water source is formed.

The contacting step can last for any suitable time. In some embodiments, the contacting step lasts for at least 10 seconds, 20 seconds, 30 seconds, 40 seconds, 50 seconds, 1 minute, 10 minutes, 30 minutes, 1 hour, 2 hours, 4 hours, 8 hours, 16 hours, 1 day, 3 days, 1 week, or longer.

The present methods can be used for reducing the level of hydrogen sulfide ($H_2S$), hydrosulfuric acid or a salt thereof in any suitable water source. Exemplary water source includes fresh water, pond water, sea water, produced water and a combination thereof. The water source can comprise any suitable level of produced water, e.g., at least about 1 wt-%, 2 wt-%, 3 wt-%, 4 wt-%, 5 wt-%, 6 wt-%, 7 wt-%, 8 wt-%, 9 wt-%, 10 wt-%, 20 wt-%, 30 wt-%, 40 wt-%, 50 wt-%, 60 wt-%, 70 wt-%, 80 wt-%, 90 wt-%, or more produced water.

The present methods can be used for reducing the level of hydrogen sulfide ($H_2S$), hydrosulfuric acid or a salt thereof in a water source by any suitable degree. For example, the level of $H_2S$, hydrosulfuric acid or a salt thereof in the treated water source can be reduced by at least 10%, 20%, 30%, 40%, 50%, 60%, 70%, 80%, 90%, 95%, 99%, or more from the untreated level.

The present methods can be used for reducing the level of hydrogen sulfide ($H_2S$), hydrosulfuric acid or a salt thereof in a water source from any suitable location. For example, the present methods can be used for reducing the level of hydrogen sulfide ($H_2S$), hydrosulfuric acid or a salt thereof in a water source partially or completely obtained or derived from a subterranean environment, e.g., an oil or a gas well.

In some embodiments, the present methods can further comprise directing the treated water source into a subterranean environment, e.g., an oil or a gas well, or disposing of the treated water source.

G. EXAMPLES

The following examples are included for illustrative purposes only and are not intended to limit the scope of the invention.

Example 1

Stability Comparison of Peracetic Acid Compositions with Various Stabilizers

Peracetic acid (POAA) compositions with various stabilizers as described in Table 1 were made, and on reaching equilibrium, the compositions were stored in 50° C. oven. The level of peracetic acid and hydrogen peroxide were monitored by an iodometric titration method. The results are summarized in Table 4 and FIG. 1.

TABLE 4

Peracetic acid compositions with various stabilizers

| Component | Composition I-A | Composition I-B | Composition I-C |
|---|---|---|---|
| Acetic acid | 83.0% | 83.9% | 82.9% |
| H2O2 (50%) | 16.0% | 16.0% | 16.0% |
| HEDP (60%) | 1.0% | 0.0% | 1.0% |
| Dipicolinic acid (DPA) | 0.0% | 0.1% | 0.1% |
| Total | 100.0% | 100.0% | 100.0% |
| POAA (after equilibrium) | 12.12% | 13.55% | 14.37% |
| H2O2 (after equilibrium) | 1.09% | 1.65% | 1.26% |

As can be seen in Table 4, after reaching equilibrium, the level of peracetic acid formed among compositions are in the order of I-C>I-B>I-A. While not wishing to be bound by any particular theories, it is thought that this difference in level of peracetic acid formed is due to the different efficiency of the stabilizers in the compositions. Once formed, peracetic acid starts to decompose, and the stabilizer in the composition will have a direct impact on the decomposition rate of the peracetic acid. Thus, the more efficient the stabilizer, the less decomposition will occur in the compositions, and more peracetic acid will be formed upon reaching equilibrium. This is important not only in maintaining the shelf life of a peracetic acid composition, but it is also economically beneficial to be able to form higher levels of peracetic acid in compositions from the same level of starting materials (e.g., acetic acid, and hydrogen peroxide).

TABLE 5

Stability of Peracetic Acid Compositions with Various Stabilizers

| Time | Composition I-A | | Composition I-B | | Composition I-C | |
|---|---|---|---|---|---|---|
| (day) | POAA % | $H_2O_2$% | POAA % | $H_2O_2$% | POAA % | $H_2O_2$% |
| 0 | 12.12 | 1.09 | 13.55 | 1.65 | 14.37 | 1.26 |
| 7 | 4.84 | 0.36 | 13.43 | 1.20 | 14.18 | 1.33 |
| 14 | na | na | na | na | 14.11 | 1.26 |
| 21 | 0.13 | 0.0 | 11.93 | 1.06 | 14.00 | 1.30 |
| 28 | 0.0 | 0.0 | 10.97 | 1.01 | 13.95 | 1.25 |
| 35 | 0.0 | 0.0 | 10.23 | 0.88 | 13.74 | 1.28 |
| 42 | 0.0 | 0.0 | 9.44 | 0.90 | 13.65 | 1.23 |

As can be seen from Table 5 and FIG. 1, a synergistic stabilization effect was observed when a combination of HEDP and DPA was used in the peracetic acid formulations. Surprisingly, it was found that for the high ratio peracetic acid to hydrogen peroxide compositions tested, the most commonly used stabilizer, i.e., HEDP, had only marginal effects on the stabilization of the peracetic acid. For example, as shown in Table 2, composition I-A lost more than 60% of the peracetic acid formed after only 1 week under the test conditions. Composition I-B, which used only DPA as a stabilizer, had an improved stabilization effect compared to composition I-A, and lost about 20% peracetic acid in four weeks under the tested conditions. In contrast, the combination of DPA and HEDP proved to be excellent stabilizer for the high ratio peracetic acid to hydrogen peroxide compositions tested. As shown in Table 2, Composition I-C, which had a combination of HEDP and DPA as stabilizers, lost less than 5% peracetic acid in 4 weeks under the same test conditions. The stability effect of the combination of HEDP and DPA is more than the sum of the individual stability effect of HEDP and DPA. This result demonstrates that the stability effect of the combination of HEDP and DPA is a synergistic stabilization effect, and not a merely additive effect of the individual stability effect of HEDP and DPA.

Example 2

Synergistic Stabilization Study of HEDP and DPA in High Ratio Peracetic Acid to Hydrogen Peroxide (POAA/$H_2O_2$) Compositions To systematically study the synergistic stabilization performance of HEDP and DPA, high ratio POAA/$H_2O_2$ peracetic acid compositions with various stabilizers are made as described in Table 6. The compositions, once equilibrium was reached, were stored in a 50° C. oven, and the level of peracetic acid and hydrogen peroxide were monitored by an iodometric titration method. The results are summarized in Table 7.

TABLE 6

Peracetic Acid Compositions with Various Stabilizers

| Component | IIA-1 | IIA-2 | IIA-3 | IIA-4 | IIA-5 |
|---|---|---|---|---|---|
| Acetic acid | 83.0% | 82.0% | 83.0% | 83.0% | 79.0% |
| H2O2 (50%) | 16.01% | 16.01% | 16.01% | 16.01% | 16.02% |
| HEDP (60%) | 1.00% | 2.00% | 3.01% | 4.02% | 5.00% |
| DPA | 0.00% | 0.00% | 0.00% | 0.00% | 0.00% |
| Total | 100% | 100% | 100% | 100% | 100% |
| POAA % (equilibrium) | 11.60 | 11.63 | 11.68 | 11.88 | 11.80 |
| H2O2 (equilibrium) | 0.84 | 0.91 | 0.95 | 0.95 | 1.03 |

| Component | IIB-1 | IIB-2 | IIB-3 | IIB-4 | IIB-5 |
|---|---|---|---|---|---|
| Acetic acid | 83.88% | 83.93% | 83.93% | 83.94% | 83.96% |
| H2O2 (50%) | 16.02% | 16.00% | 16.02% | 16.02% | 16.00% |
| HEDP (60%) | 0.00% | 0.00% | 0.00% | 0.00% | 0.00% |
| DPA | 0.12% | 0.10% | 0.08% | 0.06% | 0.04% |
| Total | 100% | 100% | 100% | 100% | 100% |
| POAA % (equilibrium) | 13.90 | 14.01 | 13.97 | 14.15 | 14.05 |
| H2O2 (equilibrium) | 1.15 | 1.21 | 1.29 | 1.28 | 1.20 |

| Component | IIC-1 | IIC-2 | IIC-3 | IIC-4 | IIC-5 | IIC-6 |
|---|---|---|---|---|---|---|
| Acetic acid | 84.03% | 82.90% | 81.90% | 80.92% | 79.95% | 78.97% |
| H2O2 (50%) | 16.02% | 16.00% | 16.04% | 16.02% | 16.01% | 16.01% |
| HEDP (60%) | 0.00% | 1.00% | 2.01% | 3.01% | 4.01% | 5.00% |
| DPA | 0.00% | 0.12% | 0.10% | 0.08% | 0.06% | 0.04% |
| Total | 100% | 100% | 100% | 100% | 100% | 100% |
| POAA % (equilibrium) | 11.42 | 14.51 | 14.39 | 14.30 | 14.18 | 13.43 |
| H2O2 (equilibrium) | 0.82 | 1.20 | 1.16 | 1.17 | 1.23 | 1.22 |

TABLE 7

Peracetic Acid (POAA) Stability at 50° C.

| | Time | | | | | |
|---|---|---|---|---|---|---|
| Composition | 0 days | 7 days | 14 days | 21 days | 28 days | 42 days |
| IIA-1(POAA %) | 11.60 | 4.45 | 0.44 | 0.03 | 0.00 | 0.00 |
| IIA-2(POAA %) | 11.63 | 5.03 | 0.98 | 0.19 | 0.03 | 0.00 |
| IIA-3(POAA %) | 11.68 | 5.11 | 1.96 | 0.47 | 0.10 | 0.00 |
| IIA-4(POAA %) | 11.88 | 6.24 | 2.58 | 0.83 | 0.24 | 0.00 |
| IIA-5(POAA %) | 11.80 | 6.57 | 3.03 | 1.07 | 0.34 | 0.00 |
| IIB-1(POAA %) | 13.90 | 13.02 | 12.15 | 11.22 | 10.22 | 8.32 |
| IIB-2(POAA %) | 14.01 | 13.16 | 12.16 | 11.12 | 10.21 | 8.06 |
| IIB-3(POAA %) | 13.97 | 13.10 | 12.00 | 10.96 | 10.00 | 7.82 |
| IIB-4(POAA %) | 14.15 | 13.26 | 12.25 | 11.16 | 10.12 | 7.92 |
| IIB-5(POAA %) | 14.05 | 13.04 | 11.96 | 10.88 | 9.63 | 7.36 |
| IIC-1(POAA %) | 11.42 | 2.35 | 0.05 | 0.00 | 0.00 | 0.00 |
| IIC-2(POAA %) | 14.51 | 14.47 | 14.13 | 13.99 | 13.98 | 13.76 |
| IIC-3(POAA %) | 14.39 | 14.28 | 13.99 | 13.83 | 13.81 | 13.54 |
| IIC-4(POAA %) | 14.30 | 14.19 | 14.20 | 13.93 | 13.88 | 13.21 |
| IIC-5(POAA %) | 14.18 | 14.06 | 13.94 | 13.96 | 13.66 | 13.29 |
| IIC-6(POAA %) | 13.43 | 13.96 | 13.97 | 13.81 | 13.63 | 12.94 |

The results shown in Table 7 clearly indicate that when a single stabilizer is used, simply increasing the levels of stabilizer in the composition will not proportionally increase the stability of the peracetic aid. For example, for composition series IIA, increasing HEDP from 1 to 5% resulted in only a marginal increase of stability. For composition series IIB, increasing the level of DPA beyond 0.06% had virtually no impact on the stability. Without wishing to be bound by any particular theory, it is thought that stabilizers in peracid compositions stabilize peracids through the chelating of the trace transitional metal ions in the compositions. Thus, the efficacy of a stabilizer is mainly dependent on its binding constant (Ksp) with the individual ion. Therefore, it is thought that increasing the concentration of a single stabilizer has a very limited effect on the binding capability of that stabilizer.

While not wishing to be bound by any particular theory, on one hand it is thought that the combination of two stabilizers, such as HEDP and DPA may form mixed ligand complexes with transition metals with an increased binding constant (Ksp) compared with that of the individual ligand metal complex formed when a single stabilizer is used. This mixed ligand complex is thought to lead to the significant increase in stabilizing effect seen when using a combination of stabilizers. On the other hand, DPA and the related niacin compounds are known hydroxyl radical scavengers (see for example: *Biosci. Biotechnol. Biochem.*, 2002, 66(3), 641-645.), and by quenching the hydroxyl radicals formed and thus preventing the subsequent chain decomposition reaction involving the peracid species, the stability of the corresponding peracid composition will be further improved.

Figure 2:
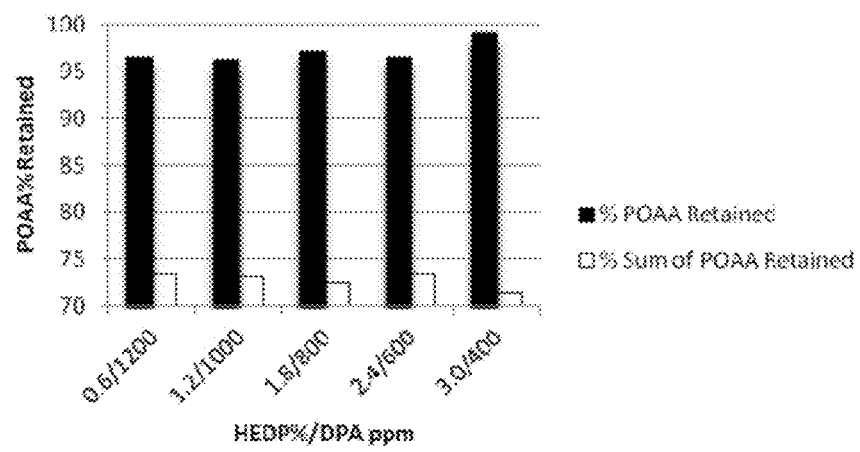
FIG. 2 illustrates synergistic stabilizing performance of HEDP and DPA.

FIG. 2 further illustrates the synergistic stabilizing capability of HEDP and DPA. The percent of POAA retained at the end of 28 days (compared to 0 days) at 50° C. of composition IIC series, which had a mixture of HEDP and DPA, was compared with the sum of percent of POAA retained from the composition IIA (HEDP only as a stabilizer) and IIB series (DPA only as a stabilizer). For example, composition IIC-2, which contains 1.2% HEDP and 1,200 ppm DPA stabilizers, retained 96% POAA; in contrast, composition IIA-2 which contains 1.2% HEDP as single stabilizer, retained 0.26% POAA; and composition IIB-1 which contains 1,200 ppm DPA as single stabilizer, retained 73.5% POAA. Combined, compositions IIA-2 and IIB-1 have the same stabilizer as IIC-2, but the sum of POAA retained from IIA-2 and IIB-1 is only 73.8%, much less than that of IIC-2. While not wishing to be bound by any particular theories, the combination of two different types of ligands, such as HEDP and DPA, may form mixed ligand complexes with the transition metals that catalytically decompose peracids, and the mixed ligand complexes formed have dramatically increased binding constant (Ksp) comparing with that of the individual ligand metal complex. The increased transition metal binding efficiency by the mixture of HEDP and DPA thus contributed to the synergistic stabilization capability of peracids.

Example 3

Self-Accelerating Decomposition Testing of Low Hydrogen Peroxide Peroxyacetic Acid Chemistries The following SADT procedure is a standardized United Nations protocol to help determine the hazard classes of self-heating substances known as the "H4 method" (sect. 28.4.4, p. 314, UN "Recommendations on the Transport of Dangerous Goods, Manual of Tests and Criteria", $5^{th}$ revised edition (2009).) The method is specific to the type of packaging used, and if the SADT temperature is found to be 45 degrees C. or lower, the product must be shipped, stored and used with rigorous refrigerated controls. Such temperature controlled requirements make it impractical to ship, and store the products. The self-heating behavior of chemistries in very large package sizes can be simulated in Dewar flasks which have previously been tested to determine that they closely reflect the heat transfer properties of the packaging to be used with the chemicals. Bulk tanks are the largest potential package sizes and to model their heat transfer properties it is recommended to use spherical Dewar flasks. The UN committee for transport of Dangerous Goods further builds a safety margin into the 300 gallon and larger package sizes by requiring that they have SADT's≥50 deg C. As per UN-H4 guidelines 28.4.1.4.1, if the temperature of the contents within the flasks does not exceed the oven temperature by greater than 6 degrees C. within 7 days, the SADT by definition is greater than the oven temperature. The guidelines further define the zero time as when the sample temperature is within 2 degrees of the oven temperature and require an 80% filled Dewar fitted with temperature monitoring and vented closures.

For this experiment, the above test conditions were used, and three spherical Dewar flasks were filled to 80% of full with chemistries I-A, I-B, and IC (See Table 8).

TABLE 8

| Component | Formula I-A | Formula I-B | Formula I-C |
| --- | --- | --- | --- |
| Acetic acid | 83.00 | 83.96 | 82.96 |
| Hydrogen peroxide (50%) | 16.00 | 16.00 | 16.00 |
| Dequest 2010 (60% HEDP) | 1.00 | 0.00 | 1.00 |
| Dipicolinic acid (DPA) | 0.00 | 0.10 | 0.10 |
| Total | 100.00 | 100.00 | 100.00 |

Figure 3:
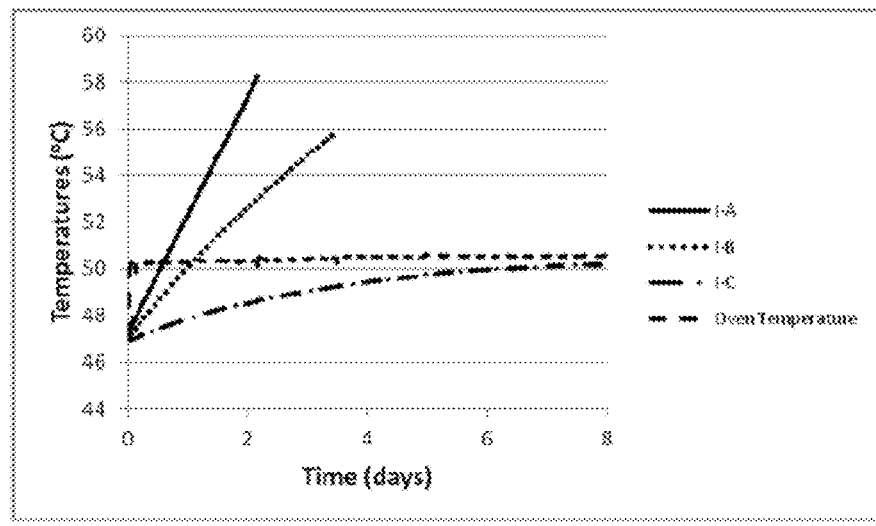
FIG. 3 illustrates SADT test of peracetic acid compositions with various stabilizers.

As can be seen in FIG. 3, chemistry I-A and I-B containing respectively HEDP only, and DPA only, as stabilizers exceeded the 6 degree exotherm limit within 1.5 days and 3 days respectively. The same concentrations of HEDP and DPA when mixed however produced such an increased stabilization such that the self-heating effects were not sufficient to reach the oven temperature within the 7 day period. Thus, this combination of stabilizers used with this peracid composition would allow for the bulk storage and transport of the peracid composition without refrigeration.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Example 4

Use Solution Peracetic Acid (POAA) Stability Comparison

The use solution stability is a very important factor in evaluating the performance of a biocide, especially for water treatment application. It is preferred that the biocide is stable during the time period of treatment, as less biocide will be needed for the application and thus are economically and environmentally beneficial. Peroxycarboxylic acids are less susceptible to decomposition than most oxidative biocides, such as halogen based biocides. However, as strong oxidation agents, the stability of peroxycarboxylic acids in use solution are strongly dependent on the water conditions, such as contaminants and pH of the water. This is especially apparent in the case of impure ground waters related to oil or gas fracking operations. In order to conserve the water used on fracking sites, the water is partially recovered and recycled at each site. While it is uncertain what component of the used fracking water might be responsible for quenching the peracetic acid, it is a critical shortcoming for commercial peracetic acid as it greatly affects the cost and antimicrobial ability of this preferred biocide. This experiment is designed to assess the use solution stability of various peracetic acid compositions in water which contains the reused water from oil and gas fracking applications.

The water used in this test contains 20% (volume) of used water from two oil and gas well fracking sites respectively, and 80% (volume) fresh water. The peracetic acid compositions tested includes a commercial peracetic acid composition (around 15% POAA, 10% $H_2O_2$) currently used as a biocide for oil and gas well water treatment; the stable, high POAA to $H_2O_2$ ratio peracetic acid composition disclosed in this application (composition I-C as shown in Table 1), and a peracetic acid composition generated by adding a catalase enzyme (100 ppm) to the diluted commercial peracid composition (1% POAA) to eliminate $H_2O_2$ to non-detectable level prior to the test. The initial POAA levels are targeted at 30 ppm, and the concentration of POAA was monitored by iodometric titration method during the intended application time of 15 minutes. The results are summarized in Table 9 below.

TABLE 9

POAA Stability of Various Peroxyacetic Acid Compositions in Use Solution Containing Used Water from Oil and Gas Well

| Peracid Composition | Water | POAA (ppm) | | | |
|---|---|---|---|---|---|
| | | 0 min. | 5 min. | 10 min. | 15 min. |
| Commercial POAA Product | Well Site A Blend | 30 | 1.3 | 0 | 0 |
| Catalase Pretreated POAA Product | Well Site A Blend | 30 | 29 | 26 | 26 |
| POAA Composition I-C | Well Site A Blend | 30 | 21 | 22 | 22 |
| Commercial POAA Product | Well Site B Blend | 30 | 0 | 0 | 0 |
| Catalase Pretreated POAA Product | Well Site B Blend | 30 | 24 | 22 | 21 |
| POAA Composition I-C | Well Site B Blend | 30 | 21 | 18 | 16 |

As shown in Table 9, it is surprisingly found that the presence of $H_2O_2$ in the peracetic acid composition has significantly negative impact on the POAA stability. For example, the commercial peracid product which contains around 15% POAA and 10% $H_2O_2$, lost almost all of its peracid content within 5 minutes whereas a hydrogen peroxide depleted version of the same (pretreated with catalase enzyme) lost only 3% of its initial activity in 10 minutes and only about 12% in 15 minutes. For composition I-C, which contains around 15% peracetic acid but only 1% hydrogen peroxide, lost only about 30% POAA in 15 min. This makes the composition I-C particularly useful in fracking water treatment application compared with the commercial peracetic acid compositions, as significantly less amount of POAA was needed for the treatment. The phenomena observed seems to be universal as two different water blend from different well sites have the similar results as shown in Table 6. While not wishing to be bound by any particular theory, the results observed may be explained by the presence of the commonly found sulfur related contaminants in the used well water, which in the presence of $H_2O_2$, will generate radical specie, and these very reactive radical species will then react with POAA to decompose it.

Example 5

Gelling Test of Peracetic Acid (POAA) Compositions with Various Levels of Hydrogen Peroxide Hydrogen peroxide is a known gel breaker in oil and gas gel fracking application. It is expected that $H_2O_2$ presented in a peracid composition will have negative impacts on the gel property. This experiment was designed to assess the levels of $H_2O_2$ in peracid compositions and their impacts on the gel property.

The $H_2O_2$ free peracetic acid was first prepared by treating a commercial peracetic acid product (15% POAA, 10% $H_2O_2$) with catalase, and after the treatment, the catalase was confirmed to be inactivated. Then known amount of $H_2O_2$ was added to the peracetic acid composition for the test. To ~500 g of water was added a guar based gel additives except the cross linker. The mixture was mixed by a blender for ~10 min, then POAA prepared as described and $H_2O_2$ was added to the mixture, and the pH of the mixture was then adjusted to 11.5 with $KOH/K_2CO_3$ (11.5 wt %/22.5%), immediately followed by the addition of the cross linker. The kinetic viscosity of the mixture was then monitored by a viscometer (Kindler) at 275 K during a time period of 2.5 hr. The success criteria is that the viscosity of the mixture maintains 200 cp or higher at the end of the test. For comparison, a gel mixture with the standard glutaraldehyde as the alternative biocide was also tested. The test results are shown in FIG. 4.

Figure 4:
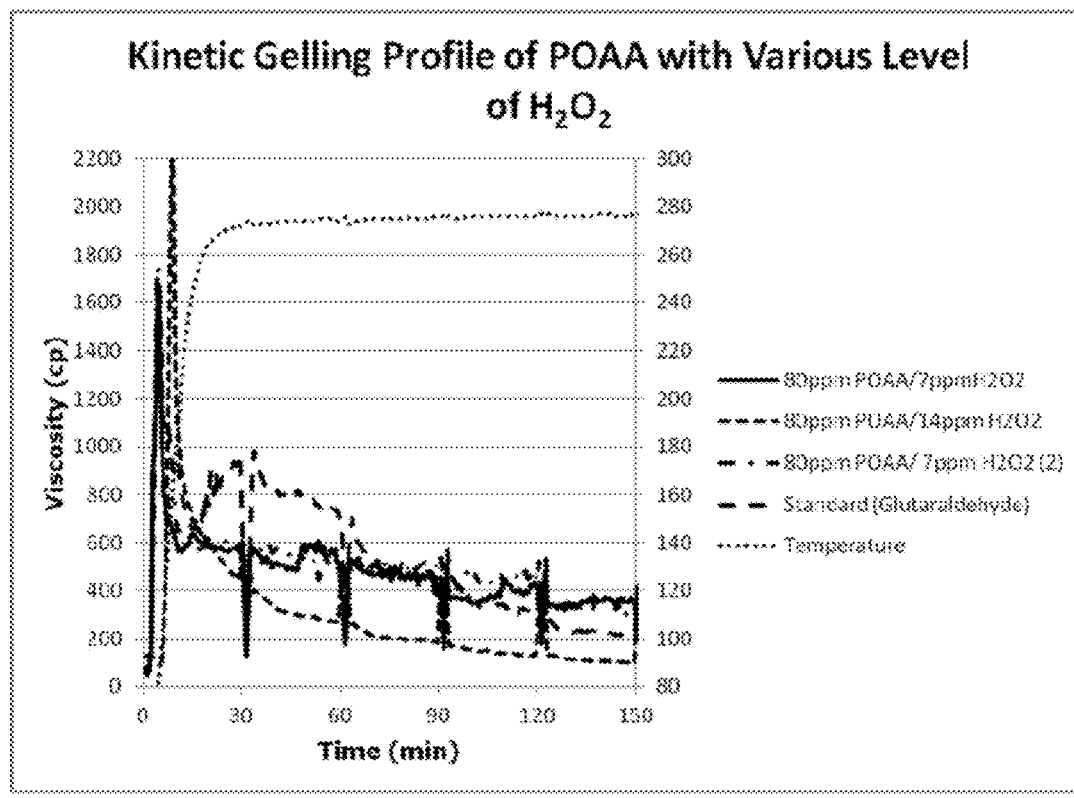
FIG. 4 illustrates kinetic viscosity profile of POAA with various levels of $H_2O_2$ in a gel fluid.

FIG. 4 clearly shows that under the investigated conditions, at the upper use level of POAA (80 ppm) as a biocide in oil and gas fracking applications, the presence of 7 ppm of $H_2O_2$ has no impact on the gel property comparing with the standard control (glutaraldehyde), while the presence of 14 ppm $H_2O_2$ cause the Gel failure.

Example 6

Gelling Test of a High POAA to $H_2O_2$ Ratio Peracetic Acid Composition

The gelling experiment as described in Example 5 was carried out using different levels of a high POAA to $H_2O_2$ ratio of peracetic acid composition (I-C) as disclosed in this application. The results are summarized in Table 10, along with the results of a commercial peracetic acid product.

TABLE 10

Summary of Kinetic Viscosity Test Results of POAA in A Gel Fluid

| Product Use level | Commercial POAA Product (15% POAA/10% $H_2O_2$) | POAA Composition I-C (15% POAA/1.2% $H_2O_2$) |
|---|---|---|
| 100 ppm | 15 ppm POAA/10 ppm $H_2O_2$ | 15 ppm POAA/1 ppm $H_2O_2$ |
| Gelling Test | Pass | Pass |
| 200 ppm | 30 ppm POAA/20 ppm $H_2O_2$ | 30 ppm POAA/2 ppm $H_2O_2$ |
| Gelling Test | Fail | Pass |
| 500 ppm | 75 ppm POAA/50 ppm $H_2O_2$ | 75 ppm POAA/6 ppm $H_2O_2$ |
| Gelling Test | Fail | Pass |
| 1000 ppm | 150 ppm POAA/100 ppm $H_2O_2$ | 150 ppm POAA/12 ppm $H_2O_2$ |
| Gelling Test | Fail | Fail |

The results from Table 10 show the significant advantages of compositions I-C in gel fracking applications compared with the common peracetic acid compositions. For example, at the POAA levels (30 ppm) required for the microorganism kill, the common peracetic acid composition will fail the gel properties of the fluid owing to the high level of $H_2O_2$ coexisted. In contrast, the high POAA to $H_2O_2$ ratio peracetic acid composition I-C has no impact of the gel properties even used at a much higher level, e.g., 75 ppm POAA.

Example 7

Enthalpy Part I—Potential Enthalpy of High and Low Hydrogen Peroxide Peroxyacid Products Peroxyacids and hydrogen peroxide are characterized by a relatively weak O—O bond which typically and especially in the case of peroxyacids is prone to homolytic fission which ultimately produces molecular oxygen, water and the parent carboxylic acids. The property of labile homolytic fission is essential to peroxyacids' utility in bleaching, polymerization and antimicrobial applications but it also can create unwelcome hazardous chemical reactions. The eventual liberation of oxygen is a highly exothermic process (heat producing) and since oxygen is a powerful oxidizing agent, downstream oxidation of organic residues are possible outcomes producing still greater amounts of heat and gas. The worst case scenario is a violent explosion and or eruption of corrosive materials.

For these above reasons peroxyacids fall under the UN category of dangerous goods and as such it is recommended by the UN that they be thoroughly characterized before determining what restrictions should be imposed for shipping, handling and storage of the same. In general these guidelines are followed strictly by local authorities and therefore a restriction requiring refrigerated handling and storage for example would likely limit sales to only a small minority of potential customers. To avoid such restrictions, most peroxyacid producers first formulate their products to be intrinsically stable and then add stabilizers such as HEDP to increase assurance against runaway exothermic decay as well as insuring sufficient shelf-life for efficacy. The unfortunate outcome is that the higher hydrogen peroxide concentrations required for achieving intrinsic stability increase the potential enthalpy and increase the violence of a runaway chemical reaction.

As shown in Table 11, formulae III-A, III-B, and III-C possess approximately twice the potential enthalpy as do formulae I-A, I-B and I-C and yet both deliver 15% peroxyacetic acid. And while the reduction in hydrogen peroxide improves the enthalpic potential for the I-type formula, only in the I-C case does the product possess sufficient shelf stability to allow manufacturing, warehousing and usage before they have lost excessive portions of their initial peroxyacetic acid.

And while the typical chelator usually is sufficient to stabilize formulations made with relatively pure chemicals they cannot practically be high enough to overcome gross contamination events. In fact, accidental contamination of peroxyacid products is not an unknown event and has caused fatal explosions involving peroxides on many occasions. Given that the metal chelator stabilizers added for shipping handling and storage can be overwhelmed by a gross contamination event it is desirable to minimize the potential energy relative to the peroxyacid content of the product. This is especially the case when considering bulk storage scenarios involving for example several thousand gallons of product.

Currently there are several provisions made for contamination accidents, one is the formulated metal chelating agent always present, the other is gas venting arrangements plumbed into bulk tanks as well as water coolant kept on standby. Again, in the case of formulae IA and IB while they halve the potential enthalpy of a typical 15% POAA product their very low hydrogen peroxide levels severely compromise their shelf-stability. In fact, the stability is so poor for IA and IB that 100% decomposition occurs within 1-2 weeks when stored at 40 C for <1 week. In example I-C, however, the unique synergistic stabilizer combination is very successful at providing sufficient shelf-life. The synergistic stabilizer combination found in I-C allows 15% peroxyacetic acid formula with a greatly reduced hydrogen peroxide and thus a reduced potential heat of reaction upon a runaway of 230 joules/g (non-combustion scenario) or 745 joules/g if the combustion scenario predominates. In contrast the more traditional peroxyacid product represented by III-A through III-C possesses a potential enthalpy of −515 joules/g (the non-combustion scenario) to −1661 joules/g if the combustion scenario predominates.

Example 8

Enthalpy Part II—Self-Accelerating Decomposition Testing of Low Hydrogen Peroxide Peroxyacetic Acid Chemistries The following SADT procedure is a standardized United Nations protocol to help determine the hazard classes of self-heating substances known as the "H4 method." The method is package specific and if the SADT temperature is found to be 45 degrees C. or lower the product must be shipped, stored and used with rigorous refrigerated controls. Such controlling requirements would likely render a product to be impractical for commerce as well as dangerous and unwelcome in most facilities.

TABLE 11

| Component | Formula I-A | Formula I-B | Formula IC | Formula III-A | Formula III-B | Formula III-C |
|---|---|---|---|---|---|---|
| Acetic acid | 83.00 | 83.96 | 82.96 | 43.85 | 43.85 | 43.85 |
| Hydrogen peroxide (50%) | 16.00 | 16.00 | 16.00 | 35.60 | 35.60 | 35.60 |
| Dequest 2010 (60% HEDP) | 1.00 | 0.00 | 1.00 | 1.00 | 1.00 | 1.00 |
| Dipicolinic acid (DPA) | 0.00 | 0.10 | 0.10 | 0.10 | 0.10 | 0.10 |
| Total | 100.00 | 100.00 | 100.00 | 100.00 | 100.00 | 100.00 |
| Theoretical scenario 1 (assume no combustion, only peroxide bonds broken and no vaporization of liquids) | | | | | | |
| Heat of Reaction (joule/g) | −230 | −230 | −230 | −515 | −515 | −515 |
| Theoretical scenario 2 (assume that combustion consumes all of the available oxygen and only volatiles evaporate) | | | | | | |
| Heat of Reaction (joule/g) | −745 | −745 | −745 | −1661 | −1661 | −1661 |

Since the O—O bond is intrinsically weak, metal contaminants such as the ubiquitous ferric and ferrous ions (iron), catalyze O—O bond fission and thus require that peroxyacids be formulated to include stabilizers such as metal chelators.

In the interest of safety the self-heating behavior of chemistries in very large package sizes is simulated in Dewar flasks which have previously been tested to determine that they closely reflect the heat transfer properties of the package. Bulk tanks are the largest potential package sizes and to model their heat transfer properties it is recommended to use spherical Dewar flasks. The UN committee for transport of Dangerous Goods further builds a safety margin into the 300 gallon and larger package sizes by requiring that they have SADT's≥50 deg C. As per UN-H4 guidelines 28.4.1.4.1 if the temperature of the content does not exceed the oven temperature by greater than 6 degrees C. within 7 days, the SADT by definition is greater than the oven temperature. The guidelines further define the zero time as when the sample temperature is within 2 degrees of the oven temperature and they require an 80% filled Dewar fitted with temperature monitoring and vented closures. These criteria were fulfilled as 3 spherical Dewar flasks were filled to 80% of full with chemistries I-A, I-B and I-C (see Table 12 below).

TABLE 12

| Component | Formula I-A | Formula I-B | Formula I-C |
|---|---|---|---|
| Acetic acid | 83 | 83.96 | 82.96 |
| Hydrogen peroxide (50%) | 16 | 16 | 16 |
| Dequest 2010 (60% HEDP) | 1 | 0 | 1 |
| Dipicolinic acid (DPA) | 0 | 0.1 | 0.1 |
| Total | 100 | 100 | 100 |
| Theoretical scenario 1 (assume no combustion, only peroxide bonds broken and no vaporization of liquids) | | | |
| Heat of Reaction (joule/g) | −230 | −230 | −230 |
| Observed: Differential Scanning Calorimetry, Heat Flow (between 20 and 140 deg C.) | | | |
| Heat of Reaction (joule/g) | −205 | −147 | 0 |
| Self Accelerating Decomposition Study in Bulk Storage Scenario | | | |
| Time before failure in 50 deg C. Oven (days): | 2 | 3 | >7 |

As can be seen in FIG. 3, formulae I-A and I-B containing respectively HEDP only and DPA only stabilizers exceeded the 6 degree exotherm limit within 1.5 days and 3 days respectively. The same concentrations of HEDP and DPA when mixed however produced such an extreme stabilization that the self-heating effects were not sufficient to reach the oven temperature within the 7 day period. On the basis of the H4 protocol it appears that this synergistic combination uniquely earns the allowance of bulk storage and transport without refrigeration, at least for this exemplary type of percarboxylic acid and hydrogen peroxide compositions (e.g., formula I-C type of formula).

Example 9

Quantitation of Peroxide Gases of Decomposition

The volume of peroxides' gases of decomposition was measured using a water filled U-tube fitted with a minimal volume tubing connected to a non-coring syringe needle. The manometer made of pyrex glass was filled partially with deionized water colored with FD&C blue dye #1 and 1,000 ppm of non-ionic surfactant. The dye allows for increased visibility of the water columns and the surfactant lowers the surface tension allowing for unbroken water columns. The manometer was also fitted with a metric ruler to allow the convenient determination of the column heights difference. Given that 1 atmosphere of pressure corresponds with 1,006 cm of water column height and the limit of resolution on the column and ruler combination is about 1 mm, the signal/noise ratio approximates 10:1.

Procedure. Four head space vials were double rinsed with the sample solution before adding 5 mL of sample solution (via Repeat Pipettor) and sealing the vials with a silicone backed PTFE septum with aluminum cap. Immediately after sealing the vials the temperature and barometric pressure were recorded. A set of water blank replicates of the same volume were also included. The sealed vials were stored for 24-48 hours at ambient temperatures inside a dark cabinet to allow for optimal gas pressure generation.

Calculations. By calibration of the U-tube water column displacement using a precision gas syringe, the water column height to gas volume ratio was calculated. Using the assumption of peroxide decay to molecular oxygen (ignoring $CO_2$ or CO gases etc.), these values were converted to gas volumes and the loss of available oxygen in the sample was thereby calculated using the formulae below:

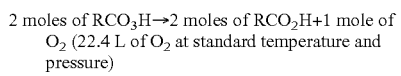

2 moles of $RCO_3H \rightarrow 2$ moles of $RCO_2H + 1$ mole of $O_2$ (22.4 L of $O_2$ at standard temperature and pressure)

And

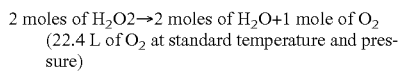

2 moles of $H_2O_2 \rightarrow 2$ moles of $H_2O + 1$ mole of $O_2$ (22.4 L of $O_2$ at standard temperature and pressure)

As shown in Table 13 below, the synergistic combination of DPA and HEDP reduced the "Rel. Loss" rate of $O_2$ for I-C to ⅛ that of 1-A and better than ⅓$^{rd}$ of that of 1-B as measured by the gas volumes of decay. In addition it can be seen that the synergistic combination brings it essentially equal to the rate of loss of the more typical commercial peracids as well as that of a 50% active hydrogen peroxide raw material.

TABLE 13

| Chemistry | Active DPA Conc. (ppm) | Active HEDP Conc. (ppm) | Init. Ht. (mm) | Fin. Ht. (mm) | Net Gas Gen. (mL) | Net $O_2$ Lost (g) | Initial POAA (w/w, %) | Initial $H_2O_2$ (w/w, %) | Initial $O_2$ (w/w, %) | Rel. Loss $O_2$ (w/w, %) |
|---|---|---|---|---|---|---|---|---|---|---|
| I-A | 0 | 6000 | 145 | 415 | 25.0 | 0.036 | 11.48 | 1.00 | 2.89 | 0.27% |
| I-B | 1000 | 0 | 145 | 266 | 10.8 | 0.015 | 13.03 | 1.14 | 3.28 | 0.10% |
| I-C | 1000 | 6000 | 143 | 181 | 3.0 | 0.004 | 14.16 | 1.27 | 3.58 | 0.03% |
| D: Commercial Peracid 15% PAA/10% Hydrogen peroxide | 0 | 9000 | 143 | 227 | 7.4 | 0.011 | 14.60 | 10.60 | 8.06 | 0.03% |
| E: Commercial Peracid 5% PAA/27% Hydrogen peroxide | 0 | 9600 | 143 | 238 | 8.4 | 0.012 | 5.10 | 27.00 | 13.78 | 0.02% |

TABLE 13-continued

| Chemistry | Active DPA Conc. (ppm) | Active HEDP Conc. (ppm) | Init. Ht. (mm) | Fin. Ht. (mm) | Net Gas Gen. (mL) | Net $O_2$ Lost (g) | Initial POAA (w/w, %) | Initial $H_2O_2$ (w/w, %) | Initial $O_2$ (w/w, %) | Rel. Loss $O_2$ (w/w, %) |
|---|---|---|---|---|---|---|---|---|---|---|
| F: Hydrogen peroxide, 50% active | 0 | 0 | 143 | 275 | 11.9 | 0.017 | 0.00 | 50.00 | 23.53 | 0.02% |

Example 10

Hydrogen Sulfide Reduction

Several test were conducted using exemplary formulations of the present invention to reduce hydrogen sulfide ($H_2S$) spiked in distilled water. The ingredients of the exemplary formulations (13523-37-1 and 123523-37-2) and a control formulation (Tsunami 100 (EC6734A)) are listed in the following Table 14.

TABLE 14

| Composition | 13523-37-1 Wt(g) | 13523-37-1 % | 123523-37-2 Wt(g) | 123523-37-2 % | EC6734A Wt(g) | EC6734A % |
|---|---|---|---|---|---|---|
| Acetic acid | 719 | 71.9 | 769 | 76.9 | 438.5 | 43.85 |
| $H_2O_2$ (50%) | 270 | 27 | 220 | 22 | 0 | 0 |
| $H_2O_2$ (35%) | 0 | 0 | 0 | 0 | 508.5 | 50.85 |
| Dequest 2010 (60%) | 10 | 1 | 10 | 1 | 15 | 1.5 |
| DPA | 1 | 0.1 | 1 | 0.1 | 0 | 0 |
| DI Water | 0 | 0 | 0 | 0 | 38 | 3.8 |
| Total | 1,000 | 100 | 1,000 | 100 | 1,000 | 100 |
| *POAA % | | 22.3 | | 17.34 | | 14.46 |
| $H_2O_2$% | | 3.78 | | 2.20 | | 10.65 |
| POAA/$H_2O_2$ | | 5.90 | | 7.88 | | 1.36 |

Figure 5A:
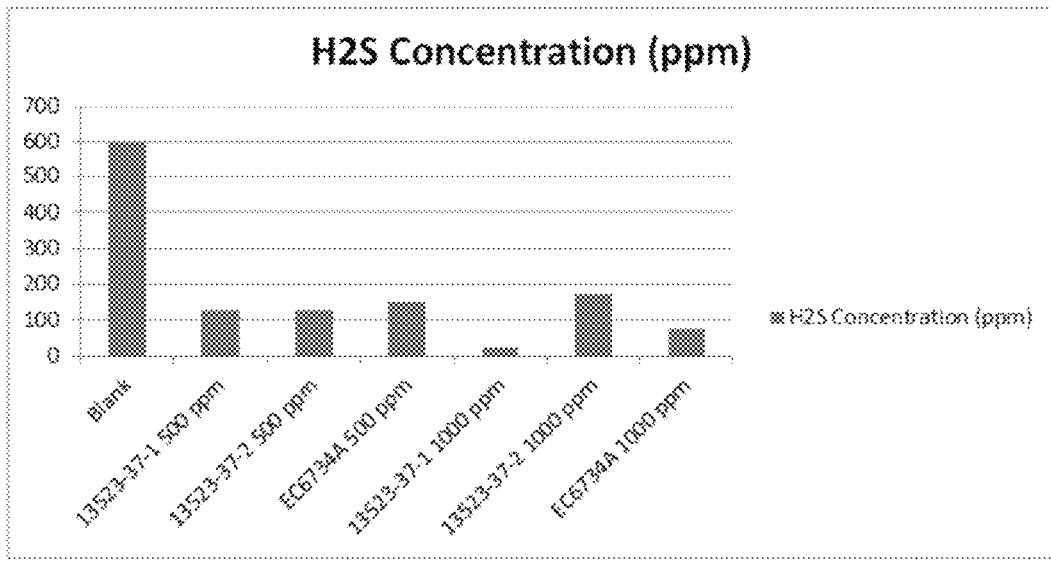
FIGS. 5A and 5B illustrate an example of $H_{2S}$ reduction using various levels of formulations 13523-37-1 and 13523-37-2.
Figure 5B:
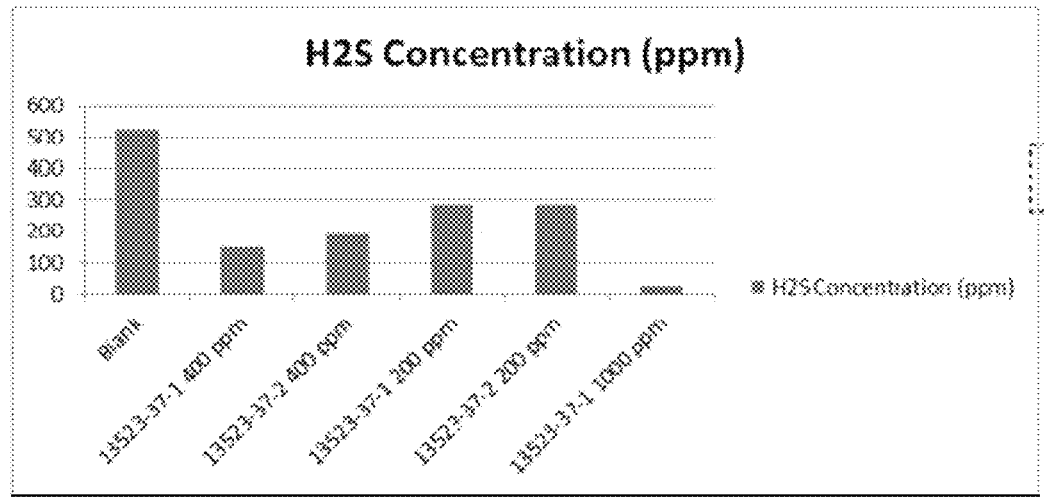
Figure 6A:
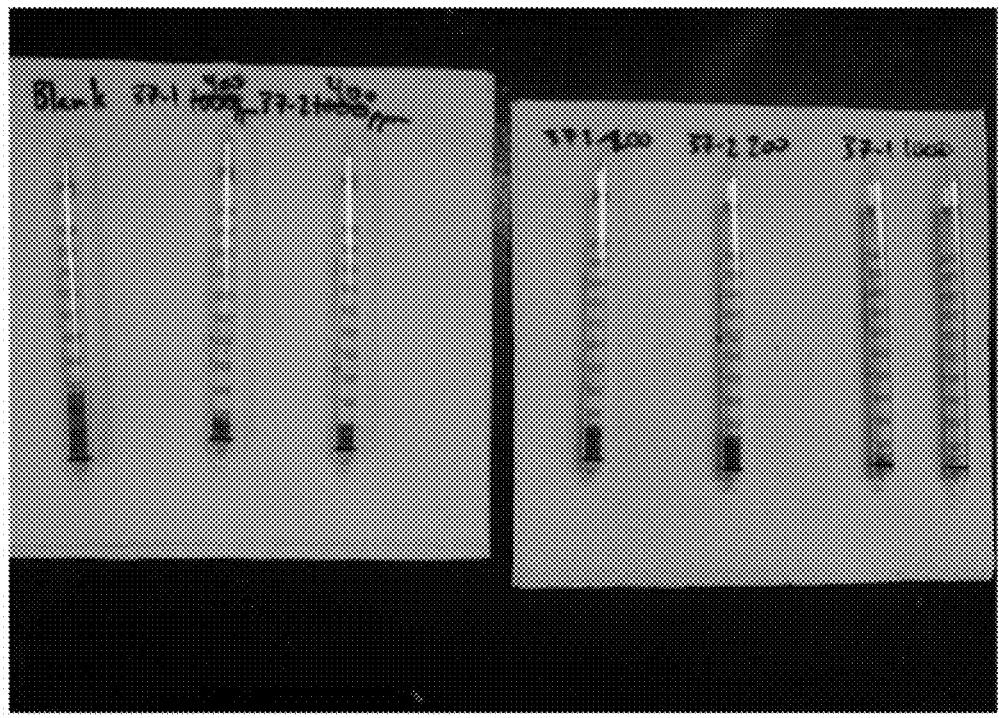
FIGS. 6A and 6B illustrate another example of $H_{2S}$ reduction using various levels of formulations 13523-37-1 and 13523-37-2.
Figure 6B:
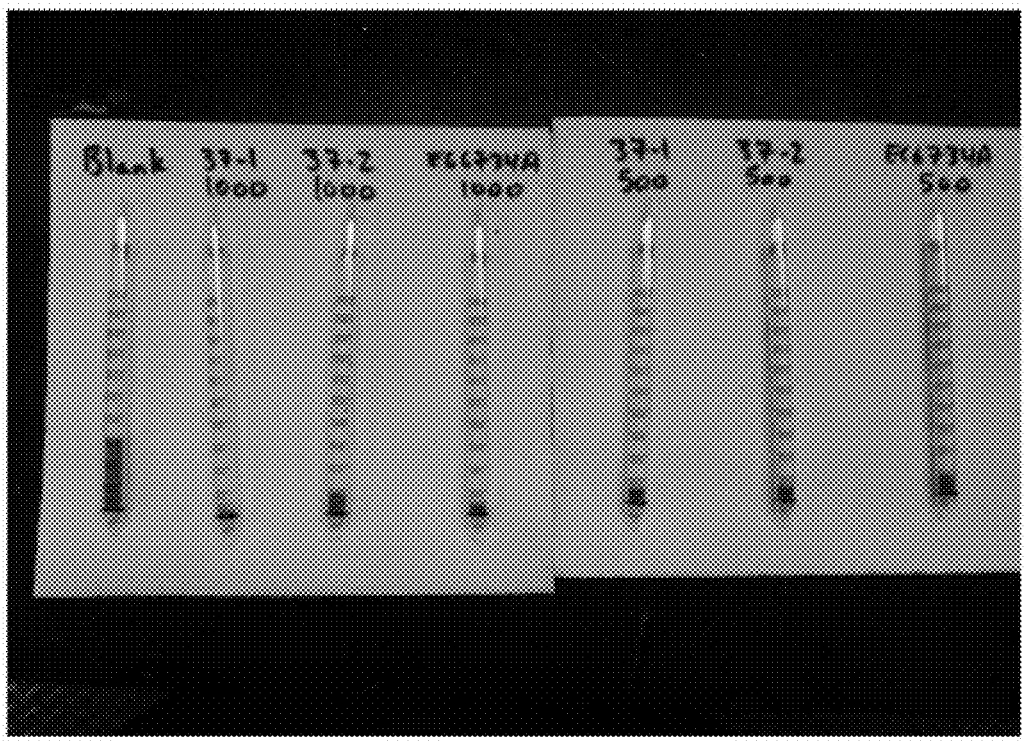

The test results are shown in the following Table 15, and in FIGS. 5A, 5B, 6A and 6B. As shown in Table 15, formulation 13523-37-1 at 1,000 ppm reduced $H_2S$ about 95%, while formulation 13523-37-1 at 500 ppm reduced $H_2S$ about 80%. Interestingly, a low dosage seems to reduce the $H_2S$ to close to 50%. When formulation 13523-37-2 was used at 1,000 ppm, $H_2S$ level was reduced to 175 ppm. When formulation 13523-37-2 was used at 500 pm, $H_2S$ level was reduced to 125 ppm. FIG. 5a shows an example of hydrogen sulfide ($H_2S$) reaction in deionized water solution with different relative concentrations of peracetic acid and hydrogen peroxide (see Table 15 for concentrations). Increased concentrations are shown to result in increased destruction of hydrogen sulfide. FIG. 5b shows another example of hydrogen sulfide ($H_2S$) reaction in deionized water solution with different relative concentrations of peracetic acid and hydrogen peroxide (see Table 15 for concentrations). Increased concentrations are shown to result in increased destruction of hydrogen sulfide.

TABLE 15

| Lease Name & Number | Sample Description | $H_2S$ Concentration (ppm) |
|---|---|---|
| d $H_2O$ spiked with $H_2S$ | Blank | 525 |
| d $H_2O$ spiked with $H_2S$ | 13523-37-1 400 ppm | 150 |
| d $H_2O$ spiked with $H_2S$ | 123523-37-2 400 ppm | 190 |
| d $H_2O$ spiked with $H_2S$ | 13523-37-1 200 ppm | 285 |
| d $H_2O$ spiked with $H_2S$ | 123523-37-2 200 ppm | 285 |
| d $H_2O$ spiked with $H_2S$ | 13523-37-1 1,000 ppm | 25 |
| d $H_2O$ spiked with $H_2S$ | Blank | 600 |
| d $H_2O$ spiked with $H_2S$ | 13523-37-1 500 ppm | 125 |
| d $H_2O$ spiked with $H_2S$ | 123523-37-2 500 ppm | 125 |
| d $H_2O$ spiked with $H_2S$ | EC6734A 500 ppm | 150 |
| d $H_2O$ spiked with $H_2S$ | 13523-37-1 1,000 ppm | 25 |
| d $H_2O$ spiked with $H_2S$ | 123523-37-2 1,000 ppm | 175 |
| d $H_2O$ spiked with $H_2S$ | EC6734A 1,000 ppm | 75 |

H. EXEMPLARY EMBODIMENTS

The present invention is further illustrated by the following exemplary embodiments:

1. A composition, which composition comprises:
   1) a $C_1$-$C_{22}$ carboxylic acid;
   2) a $C_1$-$C_{22}$ percarboxylic acid;
   3) hydrogen peroxide;
   4) a first stabilizing agent, which is a picolinic acid or a compound having the following Formula (IA):

(IA)

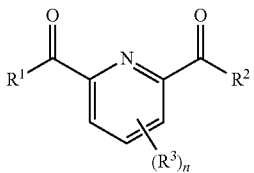

wherein

R¹ is OH or —NR$^{1a}$R$^{1b}$, wherein R$^{1a}$ and R$^{1b}$ are independently hydrogen or (C$_1$-C$_6$)alkyl;

R² is OH or —NR$^{2a}$R$^{2b}$, wherein R$^{2a}$ and R$^{2b}$ are independently hydrogen or (C$_1$-C$_6$)alkyl;

each R³ is independently (C$_1$-C$_6$)alkyl, (C$_2$-C$_6$)alkenyl or (C$_2$-C$_6$)alkynyl; and n is a number from zero to 3;

or a salt thereof;

or a compound having the following Formula (IB):

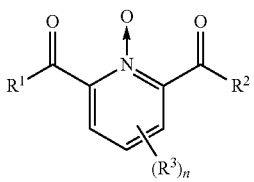

(IB)

wherein

R¹ is OH or —NR$^{1a}$R$^{1b}$, wherein R$^{1a}$ and R$^{1b}$ are independently hydrogen or (C$_1$-C$_6$)alkyl;

R² is OH or —NR$^{2a}$R$^{2b}$, wherein R$^{2a}$ and R$^{2b}$ are independently hydrogen or (C$_1$-C$_6$)alkyl;

each R³ is independently (C$_1$-C$_6$)alkyl, (C$_2$-C$_6$)alkenyl or (C$_2$-C$_6$)alkynyl; and n is a number from zero to 3;

or a salt thereof;

5) a second stabilizing agent, which is a compound having the following Formula (IIA):

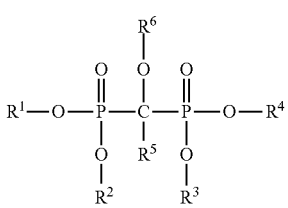

(IIA)

wherein

R¹, R², R³, and R⁴ are independently hydrogen, (C$_1$-C$_6$) alkyl, (C$_2$-C$_6$)alkenyl or (C$_2$-C$_6$)alkynyl, or C$_{6-20}$ aryl;

R⁵ is (C$_1$-C$_6$)alkyl, (C$_2$-C$_6$)alkenyl or (C$_2$-C$_6$)alkynyl; and

R⁶ is hydrogen, (C$_1$-C$_6$)alkyl, (C$_2$-C$_6$)alkenyl or (C$_2$-C$_6$) alkynyl;

or a compound having the following Formula (IIB):

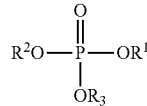

(IIB)

wherein

R¹, R², and R³ are independently hydrogen, (C$_1$-C$_6$)alkyl, (C$_2$-C$_6$)alkenyl or (C$_2$-C$_6$)alkynyl, or C$_{6-20}$ aryl;

or a salt thereof; and wherein said hydrogen peroxide has a concentration of at least about 0.1 wt-%, the C$_1$-C$_{22}$ percarboxylic acid has a concentration of at least about 2 times of the concentration of said hydrogen peroxide, and said composition has a pH at about 4 or less.

2. The composition of embodiment 1, wherein the C$_1$-C$_{22}$ percarboxylic acid has a concentration of at least about 6 times of the concentration of the hydrogen peroxide.

3. The composition of embodiment 1, wherein the C$_1$-C$_{22}$ percarboxylic acid has a concentration of at least about 10 times of the concentration of the hydrogen peroxide.

4. The composition of any of embodiments 1-3, wherein the C$_1$-C$_{22}$ carboxylic acid is a C$_2$-C$_{20}$ carboxylic acid.

5. The composition of any of embodiments 1-4, wherein the C$_1$-C$_{22}$ carboxylic acid comprises acetic acid, octanoic acid and/or sulfonated oleic acid.

6. The composition of any of embodiments 1-5, wherein the C$_1$-C$_{22}$ carboxylic acid has a concentration from about 10 wt-% to about 90 wt-%.

7. The composition of any of embodiments 1-5, wherein the C$_1$-C$_{22}$ carboxylic acid has a concentration from about 20 wt-% to about 80 wt-%.

8. The composition of any of embodiments 1-7, wherein the C$_1$-C$_{22}$ percarboxylic acid is a C$_2$-C$_{20}$ percarboxylic acid.

9. The composition of any of embodiments 1-8, wherein the C$_1$-C$_{22}$ percarboxylic acid comprises peroxyacetic acid, peroxyoctanoic acid and/or peroxysulfonated oleic acid.

10. The composition of any of embodiments 1-9, wherein the C$_1$-C$_{22}$ percarboxylic acid has a concentration from about 1 wt-% to about 40 wt-%.

11. The composition of any of embodiments 1-9, wherein the C$_1$-C$_{22}$ percarboxylic acid has a concentration from about 1 wt-% to about 20 wt-%.

12. The composition of any of embodiments 1-11, wherein the hydrogen peroxide has a concentration from about 0.5 wt-% to about 10 wt-%.

13. The composition of any of embodiments 1-11, wherein the hydrogen peroxide has a concentration from about 1 wt-% to about 2 wt-%.

14. The composition of any of embodiments 1-13, wherein the C$_1$-C$_{22}$ carboxylic acid is acetic acid and the C$_1$-C$_{22}$ percarboxylic acid is peracetic acid.

15. The composition of any of embodiments 1-14, wherein the C$_1$-C$_{22}$ carboxylic acid has a concentration of about 70 wt-%, the C$_1$-C$_{22}$ percarboxylic acid has a concentration of about 15 wt-%, and the hydrogen peroxide has a concentration of at least about 1 wt-%.

16. The composition of any of embodiments 1-15, wherein the first stabilizing agent is a picolinic acid, or a salt thereof.

17. The composition of any of embodiments 1-15, wherein the first stabilizing agent is 2,6-pyridinedicarboxylic acid, or a salt thereof.

18. The composition of any of embodiments 1-17, wherein the first stabilizing agent has a concentration from about 0.005 wt-% to about 5 wt-%.

19. The composition of any of embodiments 1-17, wherein the first stabilizing agent has a concentration from about 0.05 wt-% to about 0.15 wt-%.

20. The composition of any of embodiments 1-19, wherein the second stabilizing agent is 1-hydroxy ethylidene-1,1-diphosphonic acid (HEDP), or a salt thereof.

21. The composition of any of embodiments 1-20, wherein the second stabilizing agent has a concentration from about 0.1 wt-% to about 10 wt-%.

22. The composition of any of embodiments 1-20, wherein the second stabilizing agent has a concentration from about 0.5 wt-% to about 5 wt-%.

23. The composition of any of embodiments 1-20, wherein the second stabilizing agent has a concentration from about 0.6 wt-% to about 1.8 wt-%.

24. The composition of any of embodiments 1-23, which further comprises a substance that aids solubilization of the first and/or second stabilizing agent(s).

25. The composition of any of embodiments 1-24, wherein the first stabilizing agent is a 2,6-pyridinedicarboxylic acid, or a salt thereof, and the second stabilizing agent is HEDP, or a salt thereof.

26. The composition of any of embodiments 1-25, wherein the first and second stabilizing agents delay or prevent the composition from exceeding its self-accelerating decomposition temperature (SADT).

27. The composition of any of embodiments 1-26, which retains at least about 80% of the $C_1$-$C_{22}$ percarboxylic acid activity after storage of about 30 days at about 50° C.

28. A method for storing a percarboxylic acid containing composition, which method comprises storing a composition of any of embodiments 1-27, wherein said composition retains at least about 80% of the $C_1$-$C_{22}$ percarboxylic acid activity after storage of about 30 days at about 50° C.

29. A method for transporting a percarboxylic acid containing composition, which method comprises transporting a composition of any of embodiments 1-27, wherein the SADT of said composition is elevated to at least 45° C. during transportation.

30. A method for treating water, which method comprises providing a composition of any of embodiments 1-27 to a water source in need of treatment to form a treated water source, wherein said treated water source comprises from about 1 ppm to about 1,000 ppm of said $C_1$-$C_{22}$ percarboxylic acid.

31. The method of embodiment 30, wherein the water source in need of treatment is selected from the group consisting of fresh water, pond water, sea water, produced water and a combination thereof.

32. The method of embodiment 31, wherein the water source comprises at least about 1 wt-% produced water.

33. The method of any of embodiments 30-32, wherein the treated water source comprises from about 10 ppm to about 200 ppm of the $C_1$-$C_{22}$ percarboxylic acid.

34. The method of any of embodiments 30-33, wherein the $C_1$-$C_{22}$ percarboxylic acid comprises peroxyacetic acid, peroxyoctanoic acid and/or peroxysulfonated oleic acid.

35. The method of any of embodiments 30-34, wherein the treated water source comprises from about 1 ppm to about 15 ppm of the hydrogen peroxide.

36. The method of any of embodiments 30-35, wherein the treated water source retains at least about 60% of the initial $C_1$-$C_{22}$ percarboxylic acid activity in the treated water source for 15 minutes after the treated water source is formed.

37. The method of any of embodiments 30-36, wherein the level of a microorganism, if present in the water source, is stabilized or reduced.

38. The method of any of embodiments 30-37, wherein antimicrobial efficacy of the composition of any of embodiments 1-27 on the treated water source is comparable to antimicrobial effect of a water source that does not contain produced water.

39. The method of any of embodiments 30-38, wherein the treated water source reduces corrosion caused by hydrogen peroxide and reduces microbial-induced corrosion, and the composition of any of embodiments 1-27 does not substantially interfere with a friction reducer, a viscosity enhancer, other functional ingredients present in the treated water source, or a combination thereof.

40. The method of any of embodiments 30-39, which further comprises adding a peroxidase or a catalase to the water source before a composition of any of embodiments 1-27 is provided to the water source, and wherein the peroxidase or a catalase further reduces the hydrogen peroxide level in the treated water source.

41. The method of any of embodiments 30-40, which further comprises directing the treated water source into a subterranean environment or disposing of the treated water source.

42. The method of any of embodiments 30-41, wherein the water source does not comprise reuse water, the treated water source comprises from about 10 ppm to about 20 ppm of the $C_1$-$C_{22}$ percarboxylic acid and from about 1 ppm to about 2 ppm of hydrogen peroxide and the treated water source does not comprise a friction reducer and/or a rheology modifier.

43. The method of any of embodiments 30-42, wherein the water source is a blended water source that comprises about 80 wt-% fresh water or pond water and about 20 wt-% of reuse water, the treated water source comprises from about 25 ppm to about 35 ppm of the $C_1$-$C_{22}$ percarboxylic acid and from about 2 ppm to about 3 ppm of hydrogen peroxide and catalase, the treated water source does not comprise a friction reducer and/or a rheology modifier, and the treated water source is formed before reaching a blending tub.

44. The method of any of embodiments 30-43, wherein the water source is a blended water source that comprises about 80 wt-% fresh water or pond water and about 20 wt-% of reuse water, the treated water source comprises from about 25 ppm to about 35 ppm of the $C_1$-$C_{22}$ percarboxylic acid and from about 2 ppm to about 3 ppm of hydrogen peroxide and catalase, the treated water source comprises a friction reducer and/or a rheology modifier, and the treated water source is formed in a blending tub.

45. The method of any of embodiments 30-44, wherein the treated water source comprises from about 30 ppm or less of the $C_1$-$C_{22}$ percarboxylic acid and about 0.5 ppm or less of the hydrogen peroxide, the treated water source comprises a friction reducer and/or a rheology modifier, and the treated water source is directed into or is at a subterranean environment.

46. A composition, which composition comprises:
1) a $C_1$-$C_{22}$ carboxylic acid;
2) a $C_1$-$C_{22}$ percarboxylic acid;
3) hydrogen peroxide;
4) a first stabilizing agent, which is a picolinic acid or a compound having the following Formula (IA):

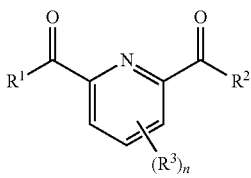

(IA)

wherein $R^1$ is OH or —$NR^{1a}R^{1b}$, wherein $R^{1a}$ and $R^{1b}$ are independently hydrogen or ($C_1$-$C_6$)alkyl;

$R^2$ is OH or —$NR^{2a}R^{2b}$, wherein $R^{2a}$ and $R^{2b}$ are independently hydrogen or ($C_1$-$C_6$)alkyl;

each $R^3$ is independently ($C_1$-$C_6$)alkyl, ($C_2$-$C_6$)alkenyl or ($C_2$-$C_6$)alkynyl; and n is a number from zero to 3;

or a salt thereof;

or a compound having the following Formula (IB):

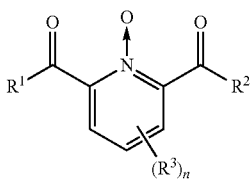

(IB)

wherein $R^1$ is OH or —$NR^{1a}R^{1b}$, wherein $R^{1a}$ and $R^{1b}$ are independently hydrogen or ($C_1$-$C_6$)alkyl;

$R^2$ is OH or —$NR^{2a}R^{2b}$, wherein $R^{2a}$ and $R^{2b}$ are independently hydrogen or ($C_1$-$C_6$)alkyl;

each $R^3$ is independently ($C_1$-$C_6$)alkyl, ($C_2$-$C_6$)alkenyl or ($C_2$-$C_6$)alkynyl; and n is a number from zero to 3;

or a salt thereof;

5) a second stabilizing agent, which is a compound having the following Formula (IIA):

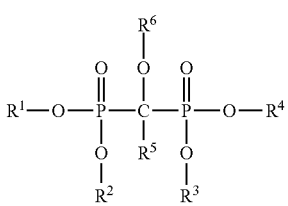

(IIA)

wherein $R^1$, $R^2$, $R^3$, and $R^4$ are independently hydrogen, ($C_1$-$C_6$) alkyl, ($C_2$-$C_6$)alkenyl or ($C_2$-$C_6$)alkynyl, or $C_{6-20}$ aryl;

$R^5$ is ($C_1$-$C_6$)alkyl, ($C_2$-$C_6$)alkenyl or ($C_2$-$C_6$)alkynyl; and $R^6$ is hydrogen, ($C_1$-$C_6$)alkyl, ($C_2$-$C_6$)alkenyl or ($C_2$-$C_6$)alkynyl;

or a salt thereof;

or a compound having the following Formula (IIB):

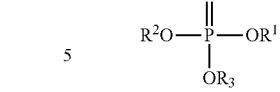

(IIB)

wherein $R^1$, $R^2$, and $R^3$ are independently hydrogen, ($C_1$-$C_6$)alkyl, ($C_2$-$C_6$)alkenyl or ($C_2$-$C_6$)alkynyl, or $C_{6-20}$ aryl;

or a salt thereof;

6) a friction reducer; and wherein said hydrogen peroxide has a concentration of about 1 ppm to about 20 ppm, and the $C_1$-$C_{22}$ percarboxylic acid has a concentration of at least about 2 times of the concentration of said hydrogen peroxide.

47. The composition of embodiment 46, wherein the hydrogen peroxide has a concentration of about 1 ppm to about 10 ppm.

48. The composition of embodiment 46 or 47, wherein the $C_1$-$C_{22}$ percarboxylic acid has a concentration of at least about 6 times of the concentration of the hydrogen peroxide.

49. The composition of any of embodiments 46-48, wherein the $C_1$-$C_{22}$ percarboxylic acid has a concentration of at least about 10 times of the concentration of the hydrogen peroxide.

50. The composition of any of embodiments 46-49, wherein the friction reducer is a polyacrylamide polymer and/or copolymer, or an acrylamide-derived polymer and/or copolymer.

51. The composition of any of embodiments 46-50, wherein the friction reducer has a concentration from about 50 ppm to about 5,000 ppm, preferably from about 100 ppm to about 1,000 ppm.

52. The composition of any of embodiments 46-51, which further comprises a proppant, a surfactant and/or a scale inhibitor.

53. The composition of embodiment 52, wherein the proppant is a sand or a ceramic bead.

54. The composition of embodiment 52, wherein the scale inhibitor is a polymer, a phosphonate or a phosphate ester.

55. The composition of any of embodiments 46-54, wherein the $C_1$-$C_{22}$ percarboxylic acid is a $C_2$-$C_{20}$ percarboxylic acid.

56. The composition of any of embodiments 46-55, wherein the $C_1$-$C_{22}$ percarboxylic acid comprises peroxyacetic acid, peroxyoctanoic acid and/or peroxysulfonated oleic acid.

57. The composition of any of embodiments 46-56, wherein the $C_1$-$C_{22}$ percarboxylic acid has a concentration from about 10 ppm to about 30 ppm and the hydrogen peroxide has a concentration from about 1 ppm to about 3 ppm.

58. The composition of any of embodiments 46-57, wherein the first stabilizing agent is a picolinic acid, or a salt thereof.

59. The composition of any of embodiments 46-57, wherein the first stabilizing agent is 2,6-pyridinedicarboxylic acid, or a salt thereof.

60. The composition of any of embodiments 46-59, wherein the first stabilizing agent has a concentration from about 0.005 wt-% to about 5 wt-%.

61. The composition of any of embodiments 46-59, wherein the first stabilizing agent has a concentration from about 0.05 wt-% to about 0.15 wt-%.

62. The composition of any of embodiments 46-61, wherein the second stabilizing agent is 1-hydroxy ethylidene-1,1-diphosphonic acid (HEDP), or a salt thereof.

63. The composition of any of embodiments 46-62, wherein the second stabilizing agent has a concentration from about 0.1 wt-% to about 10 wt-%.

64. The composition of any of embodiments 46-62, wherein the second stabilizing agent has a concentration from about 0.5 wt-% to about 5 wt-%.

65. The composition of any of embodiments 46-62, wherein the second stabilizing agent has a concentration from about 0.6 wt-% to about 1.8 wt-%.

66. The composition of any of embodiments 46-65, wherein the first stabilizing agent is a 2,6-pyridinedicarboxylic acid, or a salt thereof, and the second stabilizing agent is HEDP, or a salt thereof.

67. The composition of any of embodiments 46-66, which retains at least about 60% of the initial $C_1$-$C_{22}$ percarboxylic acid activity for 15 minutes after the composition is formed.

68. The composition of any of embodiments 46-67, wherein the hydrogen peroxide concentration is further reduced by a peroxidase or a catalase.

69. The composition of any of embodiments 46-68, which further comprises a substance that aids solubilization of the first and/or second stabilizing agent(s).

70. A method for slick water fracturing, which method comprises directing a composition of any of embodiments 46-69 into a subterranean environment.

71. The method of embodiment 70, wherein the composition is directed into a subterranean environment at a speed faster than 30 barrel (bbl)/min 72. The method of embodiment 71, wherein the composition is directed into a subterranean environment at a speed from about 50 bbl/min to about 100 bbl/min 73. The method of any of embodiments 70-72, wherein the subterranean environment comprises a well in a shale gas and/or oil reservoir.

74. The method of any of embodiments 70-73, wherein the composition is pumped down a well-bore.

75. A composition, which composition comprises:
1) a $C_1$-$C_{22}$ carboxylic acid;
2) a $C_1$-$C_{22}$ percarboxylic acid;
3) hydrogen peroxide;
4) a first stabilizing agent, which is a picolinic acid or a compound having the following Formula (IA):

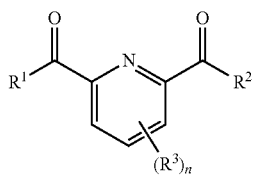

(IA)

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
or a compound having the following Formula (IB):

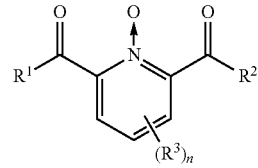

(IB)

wherein
$R^1$ is OH or —$NR^{1a}R^{1b}$, wherein $R^{1a}$ and $R^{1b}$ are independently hydrogen or ($C_1$-$C_6$)alkyl;
$R^2$ is OH or —$NR^{2a}R^{2b}$, wherein $R^{2a}$ and $R^{2b}$ are independently hydrogen or ($C_1$-$C_6$)alkyl;
each $R^3$ is independently ($C_1$-$C_6$)alkyl, ($C_2$-$C_6$)alkenyl or ($C_2$-$C_6$)alkynyl; and
n is a number from zero to 3;
or a salt thereof;
5) a second stabilizing agent, which is a compound having the following Formula (IIA):

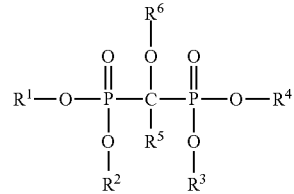

(IIA)

wherein
$R^1$, $R^2$, $R^3$, and $R^4$ are independently hydrogen, ($C_1$-$C_6$) alkyl, ($C_2$-$C_6$)alkenyl or ($C_2$-$C_6$)alkynyl, or $C_{6-20}$ aryl;
$R^5$ is ($C_1$-$C_6$)alkyl, ($C_2$-$C_6$)alkenyl or ($C_2$-$C_6$)alkynyl; and
$R^6$ is hydrogen, ($C_1$-$C_6$)alkyl, ($C_2$-$C_6$)alkenyl or ($C_2$-$C_6$) alkynyl;
or a salt thereof;
or a compound having the following Formula (IIB):

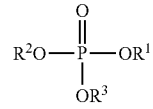

(IIB)

wherein
$R^1$, $R^2$, and $R^3$ are independently hydrogen, ($C_1$-$C_6$)alkyl, ($C_2$-$C_6$)alkenyl or ($C_2$-$C_6$)alkynyl, or $C_{6-20}$ aryl;
or a salt thereof;
6) a viscosity enhancer; and
wherein said hydrogen peroxide has a concentration of about 1 ppm to about 15 ppm, and said $C_1$-$C_{22}$ percarboxylic acid has a concentration of at least about 2 times of the concentration of said hydrogen peroxide.

76. The composition of embodiment 75, wherein the hydrogen peroxide has a concentration of about 1 ppm to about 10 ppm.

77. The composition of embodiment 75 or 76, wherein the $C_1$-$C_{22}$ percarboxylic acid has a concentration of at least about 6 times of the concentration of the hydrogen peroxide.

78. The composition of any of embodiments 75-77, wherein the $C_1$-$C_{22}$ percarboxylic acid has a concentration of at least about 10 times of the concentration of the hydrogen peroxide.

79. The composition of any of embodiments 75-78, wherein the viscosity enhancer is a conventional linear gel, a borate-crosslinked gel, an organometallic-crosslinked gel or an aluminium phosphate-ester oil gel.

80. The composition of any of embodiments 75-79, wherein the viscosity enhancer has a concentration from about 2 to about 100 units of pounds per thousand gallons, preferably from about 5 to about 65 units of pounds per thousand gallons.

81. The composition of any of embodiments 75-80, which further comprises a proppant, a surfactant, a scale inhibitor and/or a breaker.

82. The composition of embodiment 81, wherein the proppant is a sand or a ceramic bead.

83. The composition of embodiment 81, wherein the scale inhibitor is a polymer, a phosphonate or a phosphate ester.

84. The composition of embodiment 81, wherein the breaker is an oxidizer, an enzyme or a pH modifier.

85. The composition of any of embodiments 75-84, wherein the $C_1$-$C_{22}$ percarboxylic acid is a $C_2$-$C_{20}$ percarboxylic acid.

86. The composition of any of embodiments 75-85, wherein the $C_1$-$C_{22}$ percarboxylic acid comprises peroxyacetic acid, peroxyoctanoic acid and/or peroxysulfonated oleic acid.

87. The composition of any of embodiments 75-86, wherein the $C_1$-$C_{22}$ percarboxylic acid has a concentration that is effective for its anti-microbial function and the hydrogen peroxide has a concentration that will not cause gel failure.

88. The composition of embodiment 87, wherein the hydrogen peroxide has a concentration that is about 14 ppm or less.

89. The composition of any of embodiments 75-88, wherein the $C_1$-$C_{22}$ percarboxylic acid has a concentration from about 10 ppm to about 30 ppm and the hydrogen peroxide has a concentration from about 1 ppm to about 3 ppm.

90. The composition of any of embodiments 75-89, wherein the first stabilizing agent is a picolinic acid, or a salt thereof.

91. The composition of any of embodiments 75-90, wherein the first stabilizing agent is 2,6-pyridinedicarboxylic acid, or a salt thereof.

92. The composition of any of embodiments 75-91, wherein the first stabilizing agent has a concentration from about 0.005 wt-% to about 5 wt-%.

93. The composition of any of embodiments 75-92, wherein the first stabilizing agent has a concentration from about 0.05 wt-% to about 0.15 wt-%.

94. The composition of any of embodiments 75-93, wherein the second stabilizing agent is 1-hydroxy ethylidene-1,1-diphosphonic acid (HEDP), or a salt thereof.

95. The composition of any of embodiments 75-94, wherein the second stabilizing agent has a concentration from about 0.1 wt-% to about 10 wt-%.

96. The composition of any of embodiments 75-94, wherein the second stabilizing agent has a concentration from about 0.5 wt-% to about 5 wt-%.

97. The composition of any of embodiments 75-94, wherein the second stabilizing agent has a concentration from about 0.6 wt-% to about 1.8 wt-%.

98. The composition of any of embodiments 75-97, wherein the first stabilizing agent is a 2,6-pyridinedicarboxylic acid, or a salt thereof, and the second stabilizing agent is HEDP, or a salt thereof.

99. The composition of any of embodiments 75-98, which retains at least about 60% of the initial $C_1$-$C_{22}$ percarboxylic acid activity for 15 minutes after the composition is formed.

100. The composition of any of embodiments 75-99, wherein the hydrogen peroxide concentration is further reduced by a peroxidase or a catalase.

101. The composition of any of embodiments 75-100, which further comprises a substance that aids solubilization of the first and/or second stabilizing agent(s).

102. A method for high-viscosity fracturing, which method comprises directing a composition of any of embodiments 75-101 into a subterranean environment.

103. The method of embodiment 102, wherein the subterranean environment comprises a well in a gas and/or oil.

104. A method for treating a target, which method comprises a step of contacting a target with a diluted composition of any of embodiments 1-27 to form a treated target composition, wherein said treated target composition comprises from about 1 ppm to about 10,000 ppm of said $C_1$-$C_{22}$ percarboxylic acid, and said contacting step lasts for sufficient time to stabilize or reduce microbial population in and/or on said target or said treated target composition.

105. The method of embodiment 104, wherein the target is a food item or a plant item and/or at least a portion of a medium, a container, an equipment, a system or a facility for growing, holding, processing, packaging, storing, transporting, preparing, cooking or serving the food item or the plant item 106. The method of embodiment 105, wherein the plant item is a grain, fruit, vegetable or flower plant item.

107. The method of embodiment 105, wherein the plant item is a living plant item or a harvested plant item 108. The method of embodiment 105, wherein the plant item comprises a seed, a tuber, a growing plant, a cutting, or a root stock 109. The method of embodiment 105, which is used for treating a living plant tissue comprising treating the plant tissue with a diluted composition of any of embodiments 1-27 to stabilize or reduce microbial population in and/or on the plant tissue.

110. The method of embodiment 105, which is used for growing a plant on a hydroponic substrate in a hydroponic liquid supply medium, comprising:

(a) establishing a growing and living plant tissue in the hydroponic substrate;

(b) contacting the living plant tissue, the hydroponic substrate and the hydroponic liquid with a diluted composition of any of embodiments 1-27 to stabilize or reduce microbial population in and/or on the living plant tissue; and (c) harvesting a usable plant product with reduced microbial contamination.

111. The method of embodiment 105, wherein the food item is selected from the group consisting of an animal product, e.g., an animal carcass or an egg, a fruit item, a vegetable item, and a grain item.

112. The method of embodiment 111, wherein the animal carcass is selected from the group consisting of a beef, pork, veal, buffalo, lamb, fish, sea food and poultry carcass.

113. The method of embodiment 112, wherein the sea food carcass is selected from the group consisting of scallop, shrimp, crab, octopus, mussel, squid and lobster.

114. The method of embodiment 111, wherein the fruit item is selected from the group consisting of a botanic fruit, a culinary fruit, a simple fruit, an aggregate fruit, a multiple fruit, a berry, an accessory fruit and a seedless fruit.

115. The method of embodiment 111, wherein the vegetable item is selected from the group consisting of a flower bud, a seed, a leaf, a leaf sheath, a bud, a stem, a stem of leaves, a stem shoot, a tuber, a whole-plant sprout, a root and a bulb.

116. The method of embodiment 111, wherein the grain item is selected from the group consisting of maize, rice, wheat, barley, sorghum, millet, oat, triticale, rye, buckwheat, fonio and quinoa.

117. The method of embodiment 105, wherein the target is at least a portion of a container, an equipment, a system or a facility for holding, processing, packaging, storing, transporting, preparing, cooking or serving the food item or the plant item.

118. The method of embodiment 105, wherein the target is at least a portion of a container, an equipment, a system or a facility for holding, processing, packaging, storing, transporting, preparing, cooking or serving a meat item, a fruit item, a vegetable item, or a grain item.

119. The method of embodiment 105, wherein the target is at least a portion of a container, an equipment, a system or a facility for holding, processing, packaging, storing, or transporting an animal carcass.

120. The method of embodiment 104, wherein the target is at least a portion of a container, an equipment, a system or a facility used in food processing, food service or health care industry.

121. The method of embodiment 104, wherein the target is at least a portion of a fixed in-place process facility.

122. The method of embodiment 121, wherein the fixed in-place process facility comprises a milk line dairy, a continuous brewing system, a pumpable food system or a beverage processing line.

123. The method of embodiment 104, wherein the target is at least a portion of a solid surface or liquid media.

124. The method of embodiment 123, wherein the solid surface is an inanimate solid surface contaminated by a biological fluid comprising blood, other hazardous body fluid, or a mixture thereof.

125. The method of embodiment 123, wherein the solid surface is a contaminated surface.

126. The method of embodiment 125, wherein the contaminated surface comprises the surface of food service wares or equipment, or the surface of a fabric.

127. The method of any of embodiments 104-126, wherein the treated target composition comprises from about 10 ppm to about 200 ppm of the $C_1$-$C_{22}$ percarboxylic acid.

128. The method of any of embodiments 104-127, wherein the $C_1$-$C_{22}$ percarboxylic acid comprises peroxyacetic acid, peroxyoctanoic acid and/or peroxysulfonated oleic acid.

129. The method of any of embodiments 104-128, wherein the treated target composition comprises from about 1 ppm to about 15 ppm of the hydrogen peroxide.

130. The method of any of embodiments 104-129, wherein the $C_1$-$C_{22}$ percarboxylic acid has a concentration of at least about 3 times of the concentration of the hydrogen peroxide.

131. The method of any of embodiments 104-130, wherein the first stabilizing agent is a 2,6-pyridinedicarboxylic acid, or a salt thereof, and the second stabilizing agent is HEDP, or a salt thereof.

132. The method of any of embodiments 104-131, wherein the treated target composition retains at least about 60% of the initial $C_1$-$C_{22}$ percarboxylic acid activity in the treated target composition for 15 minutes after the treated target composition is formed.

133. The method of any of embodiments 104-132, wherein the contacting step lasts for at least 10 seconds.

134. The method of any of embodiments 104-133, wherein the diluted composition of any of embodiments 1-27 is applied to the target by means of a spray, a fog, or a foam.

135. The method of any of embodiments 104-134, wherein the diluted composition of any of embodiments 1-27 is applied to the target by applying in the form of a thickened or gelled solution.

136. The method of any of embodiments 104-134, wherein all or part of the target is dipped in the diluted composition of any of embodiments 1-27.

137. The method of embodiment 136, wherein the diluted composition of any of embodiments 1-27 is agitated.

138. The method of any of embodiments 104-134, wherein the diluted composition of any of embodiments 1-27 is sprayed onto the carcass at a pressure of at least 50 psi at a temperature of up to about 60° C., resulting in a contact time of at least 30 seconds.

139. The method of any of embodiments 104-138, which further comprises a vacuum treatment step.

140. The method of any of embodiments 104-139, which further comprises a step of applying an activated light source to the target.

141. The method of any of embodiments 104-140, wherein the microbial population in and/or on the target or the treated target composition is reduced by at least one $\log_{10}$.

142. The method of any of embodiments 104-140, wherein the microbial population in and/or on the target or the treated target composition is reduced by at least two $\log_{10}$.

143. The method of any of embodiments 104-140, wherein the microbial population in and/or on the target or the treated target composition is reduced by at least three $\log_{10}$.

144. The method of any of embodiments 104-143, wherein the microbial population comprises a prokaryotic microbial population.

145. The method of embodiment 144, wherein the prokaryotic microbial population comprises a bacterial or an archaeal population.

146. The method of any of embodiments 104-143, wherein the microbial population comprises an eukaryotic microbial population.

147. The method of embodiment 146, wherein the eukaryotic microbial population comprises a protozoal or fungal population.

148. The method of any of embodiments 104-143, wherein the microbial population comprises a viral population.

149. The method of any of embodiments 104-148, wherein the target is a food item or a plant item and the contacting step minimizes or does not induce an organoleptic effect in and/or on the food item or a plant item.

150. The method of any of embodiments 104-149, which is conducted at a temperature ranging from about 0° C. to about 70° C.

151. A method for reducing the level of hydrogen sulfide ($H_2S$), hydrosulfuric acid or a salt thereof in a water source, which method comprises a step of contacting a water source with a diluted composition of any of embodiments 1-27 to form a treated water source, wherein said treated water source comprises from about 1 ppm to about 10,000 ppm of said $C_1$-$C_{22}$ percarboxylic acid, and said contacting step lasts for sufficient time to stabilize or reduce the level of $H_2S$, hydrosulfuric acid or a salt thereof in said treated water source.

152. The method of embodiment 151, wherein the water source is selected from the group consisting of fresh water, pond water, sea water, produced water and a combination thereof.

153. The method of embodiment 152, wherein the water source comprises at least about 1 wt-% produced water.

154. The method of any of embodiments 151-153, wherein the treated target composition comprises from about 10 ppm to about 1,000 ppm of the $C_1$-$C_{22}$ percarboxylic acid.

155. The method of any of embodiments 151-154, wherein the $C_1$-$C_{22}$ percarboxylic acid comprises peroxyacetic acid, peroxyoctanoic acid and/or peroxysulfonated oleic acid.

156. The method of any of embodiments 151-155, wherein the treated target composition comprises from about 1 ppm to about 15 ppm of the hydrogen peroxide.

157. The method of any of embodiments 151-156, wherein the $C_1$-$C_{22}$ percarboxylic acid has a concentration of at least about 3 times of the concentration of the hydrogen peroxide.

158. The method of any of embodiments 151-157, wherein the first stabilizing agent is a 2,6-pyridinedicarboxylic acid, or a salt thereof, and the second stabilizing agent is HEDP, or a salt thereof.

159. The method of any of embodiments 151-158, wherein the level of $H_2S$, hydrosulfuric acid or a salt thereof in the treated water source is reduced by at least 10% from the untreated level.

160. The method of any of embodiments 151-159, wherein at least a portion of the water source is obtained or derived from a subterranean environment.

161. The method of any of embodiments 151-160, which further comprises directing the treated water source into a subterranean environment or disposing of the treated water source.

The claimed invention is:

1. A composition, which composition comprises:
  1) a $C_1$-$C_{22}$ carboxylic acid;
  2) a $C_1$-$C_{22}$ percarboxylic acid;
  3) hydrogen peroxide;
  4) a first stabilizing agent, which is a picolinic acid or a compound having the following Formula (IA):

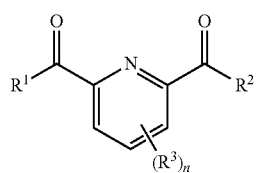

(IA)

wherein
  $R^1$ is OH;
  $R^2$ is OH;
  each $R^3$ is independently $(C_1$-$C_6)$alkyl, $(C_2$-$C_6)$alkenyl or $(C_2$-$C_6)$alkynyl; and
  n is a number from zero to 3;
  or a salt thereof, and
wherein said first stabilizing agent has a concentration of at least about 0.005 wt-%;
or a compound having the following Formula (IB):

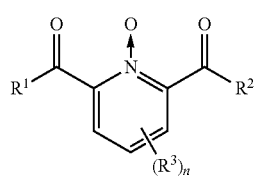

(IB)

wherein
  $R^1$ is OH;
  $R^2$ is OH;
  each $R^3$ is independently $(C_1$-$C_6)$alkyl, $(C_2$-$C_6)$alkenyl or $(C_2$-$C_6)$alkynyl; and
  n is a number from zero to 3;
  or a salt thereof;
5) a second stabilizing agent, which is a compound having the following Formula (IIA):

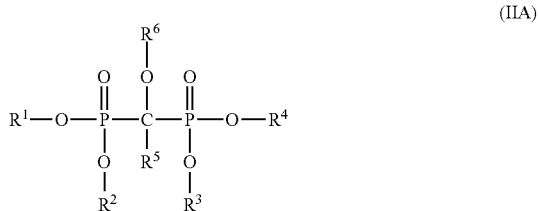

(IIA)

wherein
  $R^1$, $R^2$, $R^3$, and $R^4$ are independently hydrogen;
  $R^5$ is $(C_1$-$C_6)$alkyl, $(C_2$-$C_6)$alkenyl or $(C_2$-$C_6)$alkynyl; and
  $R^6$ is hydrogen, $(C_1$-$C_6)$alkyl, $(C_2$-$C_6)$alkenyl or $(C_2$-$C_6)$alkynyl;
  or a salt thereof, and
wherein said second stabilizing agent has a concentration of at least about 0.1 wt-%; and
wherein said $C_1$-$C_{22}$ percarboxylic acid has a concentration of about 10 wt-% to about 30 wt-%, said hydrogen peroxide has a concentration of at least about 0.1 wt-%, said $C_1$-$C_{22}$ percarboxylic acid has a concentration of at least about 3 times of the concentration of said hydrogen peroxide, and said composition has a pH at about 4 or less, and said composition retains at least about 80% of the $C_1$-$C_{22}$ percarboxylic acid activity after storage of about 30 days at about 50° C.

2. The composition of claim 1, wherein the $C_1$-$C_{22}$ percarboxylic acid has a concentration of at least about 5 times of the concentration of the hydrogen peroxide.

3. The composition of claim 1, wherein the $C_1$-$C_{22}$ carboxylic acid comprises acetic acid, octanoic acid and/or sulfonated oleic acid.

4. The composition of claim 1, wherein the $C_1$-$C_{22}$ carboxylic acid has a concentration of about 50 wt-%, the $C_1$-$C_{22}$ percarboxylic acid has a concentration of about 20 wt-%, and the hydrogen peroxide has a concentration of at least about 3 wt-%.

5. The composition of claim 1, wherein the first stabilizing agent is a 2,6-pyridinedicarboxylic acid, or a salt thereof, and the second stabilizing agent is HEDP, or a salt thereof.

6. The composition of claim 1, wherein the first and second stabilizing agents delay or prevent the composition from exceeding its self-accelerating decomposition temperature (SADT).

7. The composition of claim 1, which retains at least about 90% of the $C_1$-$C_{22}$ percarboxylic acid activity after storage of about 30 days at about 50° C.

8. A method for treating water, which method comprises providing a composition of claim 1 to a water source in need of treatment to form a treated water source, wherein said treated water source comprises from about 1 ppm to about 1,000 ppm of said $C_1$-$C_{22}$ percarboxylic acid.

9. The method of claim 8, wherein the water source in need of treatment is selected from the group consisting of fresh water, pond water, sea water, produced water and a combination thereof.

10. The method of claim 8, wherein the $C_1$-$C_{22}$ percarboxylic acid comprises peroxyacetic acid, peroxyoctanoic acid and/or peroxysulfonated oleic acid.

11. The method of claim 8, wherein the treated water source retains at least about 60% of the initial $C_1$-$C_{22}$ percarboxylic acid activity in the treated water source for 15 minutes after the treated water source is formed.

12. The method of claim 8, which further comprises directing the treated water source into a subterranean environment or disposing of the treated water source.

13. The method of claim 8, wherein the water source does not comprise reuse water, the treated water source comprises from about 10 ppm to about 20 ppm of the $C_1$-$C_{22}$ percarboxylic acid and from about 1 ppm to about 2 ppm of hydrogen peroxide and the treated water source does not comprise a friction reducer and/or a rheology modifier.

14. The method of claim 8, wherein the water source is a blended water source that comprises about 80 wt-% fresh water or pond water and about 20 wt-% of reuse water, the treated water source comprises from about 25 ppm to about 35 ppm of the $C_1$-$C_{22}$ percarboxylic acid and from about 2 ppm to about 3 ppm of hydrogen peroxide and catalase, the treated water source does not comprise a friction reducer and/or a rheology modifier, and the treated water source is formed before reaching a blending tub.

15. The method of claim 8, wherein the water source is a blended water source that comprises about 80 wt-% fresh water or pond water and about 20 wt-% of reuse water, the treated water source comprises from about 25 ppm to about 35 ppm of the $C_1$-$C_{22}$ percarboxylic acid and from about 2 ppm to about 3 ppm of hydrogen peroxide and catalase, the treated water source comprises a friction reducer and/or a rheology modifier, and the treated water source is formed in a blending tub.

16. The method of claim 8, wherein the treated water source comprises from about 30 ppm or less of the $C_1$-$C_{22}$ percarboxylic acid and about 0.5 ppm or less of the hydrogen peroxide, the treated water source comprises a friction reducer and/or a rheology modifier, and the treated water source is directed into or is at a subterranean environment.

17. The composition of claim 1, which does not comprise a mineral acid.

18. The composition of claim 6, which does not comprise a mineral acid.

19. The composition of claim 7, which does not comprise a mineral acid.

20. The composition of claim 1, wherein the first stabilizing agent has a concentration from about 0.005 wt-% to about 5 wt-%.

21. The composition of claim 1, wherein the second stabilizing agent has a concentration from about 0.1 wt-% to about 10 wt-%.

* * * * *